(12) United States Patent
Rewolinski et al.

(10) Patent No.: US 8,697,730 B2
(45) Date of Patent: Apr. 15, 2014

(54) 5-LIPOXYGENASE ACTIVATING PROTEIN (FLAP) INHIBITOR

(75) Inventors: Melissa Virginia Rewolinski, San Diego, CA (US); Kevin Murray Schaab, Spring Valley, CA (US); Christopher David King, Carlsbad, CA (US); Nicholas Simon Stock, San Diego, CA (US)

(73) Assignee: Panmira Pharmaceuticals, LLC, San Diego, CA (US)

(*) Notice: Subject to any disclaimer, the term of this patent is extended or adjusted under 35 U.S.C. 154(b) by 694 days.

(21) Appl. No.: 12/257,876

(22) Filed: Oct. 24, 2008

(65) Prior Publication Data

US 2010/0075934 A1    Mar. 25, 2010

Related U.S. Application Data

(60) Provisional application No. 60/983,119, filed on Oct. 26, 2007, provisional application No. 60/983,124, filed on Oct. 26, 2007.

(51) Int. Cl.
| | | |
|---|---|---|
| *A61K 31/44* | (2006.01) | |
| *A61K 31/405* | (2006.01) | |
| *C07D 401/00* | (2006.01) | |
| *C07D 209/02* | (2006.01) | |

(52) U.S. Cl.
USPC ............ 514/333; 514/415; 546/256; 548/469

(58) Field of Classification Search
USPC .................... 514/333, 415; 546/256; 548/469
See application file for complete search history.

(56) References Cited

U.S. PATENT DOCUMENTS

| | | | |
|---|---|---|---|
| 4,273,782 A | 6/1981 | Cross et al. | |
| 4,616,009 A | 10/1986 | Tahara et al. | |
| 4,826,987 A | 5/1989 | Nielsen et al. | |
| 5,081,138 A | 1/1992 | Gillard et al. | |
| 5,081,145 A | 1/1992 | Guindon et al. | |
| 5,093,356 A | 3/1992 | Girard et al. | |
| 5,095,031 A | 3/1992 | Brooks et al. | |
| 5,109,009 A | 4/1992 | Nielsen et al. | |
| 5,157,039 A | 10/1992 | Nielsen et al. | |
| 5,182,367 A | 1/1993 | Gillard et al. | |
| 5,190,968 A | 3/1993 | Gillard et al. | |
| 5,202,321 A | 4/1993 | Hutchinson et al. | |
| 5,204,344 A | 4/1993 | Prasit et al. | |
| 5,225,421 A | 7/1993 | Gillard et al. | |
| 5,229,516 A | 7/1993 | Musser et al. | |
| 5,232,916 A | 8/1993 | Zamboni et al. | |
| 5,252,585 A | 10/1993 | Frenette et al. | |
| 5,254,567 A | 10/1993 | Down et al. | |
| 5,272,145 A | 12/1993 | Prasit et al. | |
| 5,273,980 A | 12/1993 | Frenette et al. | |
| 5,288,743 A | 2/1994 | Brooks et al. | |
| 5,290,788 A | 3/1994 | Stevens et al. | |
| 5,290,798 A | 3/1994 | Gillard et al. | |
| 5,308,850 A | 5/1994 | Gillard et al. | |
| 5,314,898 A | 5/1994 | Chung et al. | |
| 5,334,719 A | 8/1994 | Frenette | |
| 5,374,635 A | 12/1994 | Leger et al. | |
| 5,380,850 A | 1/1995 | Prasit et al. | |
| 5,389,650 A | 2/1995 | Frenette et al. | |
| 5,399,699 A | 3/1995 | Kolasa et al. | |
| 5,420,282 A | 5/1995 | Brooks et al. | |
| 5,420,289 A | 5/1995 | Musser et al. | |
| 5,459,150 A | 10/1995 | Brooks et al. | |
| 5,552,438 A | 9/1996 | Christensen | |
| 5,635,516 A | 6/1997 | Caubere et al. | |
| 5,750,558 A | 5/1998 | Brooks et al. | |
| 5,877,329 A | 3/1999 | Chen et al. | |
| 5,972,241 A | 10/1999 | Johnson et al. | |
| 6,246,452 B1 | 6/2001 | Sekine et al. | |
| 6,500,853 B1 | 12/2002 | Seehra et al. | |
| 6,627,646 B2 | 9/2003 | Bakale et al. | |
| 6,699,883 B1 | 3/2004 | Doemling et al. | |
| 6,867,209 B1 | 3/2005 | Mavunkel et al. | |
| 7,118,869 B2 | 10/2006 | Blumenfeld et al. | |
| 7,405,302 B2 | 7/2008 | Hutchinson et al. | |
| 7,795,274 B2 | 9/2010 | Hutchinson et al. | |
| 7,834,037 B2 | 11/2010 | Hutchinson et al. | |

(Continued)

FOREIGN PATENT DOCUMENTS

| | | |
|---|---|---|
| CA | 2032253 | 6/1991 |
| CA | 1337427 | 10/1995 |

(Continued)

OTHER PUBLICATIONS

Lu P, Schrag ML, Slaughter DE, Raab CE, Shou M, and Rodrigues AD, "Mechanism-based inhibition of human liver microsomal cytochrome P450 1A2 by zileuton, a 5-lipoxygenase inhibitor," Drug Metabolism and Disposition, Nov. 2003, 31(11), 1352-1360.*

Vippagunta SR, Brittain HG, and Grant D J, "Crystalline solids," Advanced Drug Delivery Reviews, May 2001,48(1), 3-26.*

Brideau, C., et al., (1992) "Pharmacology of MK-0591 (3-[1-(4-chlorobenzyl)-3-(t-butylthio)-5-(quinolin-2-ylmethoxy)-indol-2-yl]-2,2-dimethylpropanoic acid), a Potent, Orally Active Leukotriene Biosynthesis Inhibito,". Can. J. Physiol. Pharmacol., 70, 799-807.

Chapman, K. R., et al., (1994) "The efficacy of an oral inhibitor of leukotriene synthesis (MK-0591) in asthmatics treated with inhaled steroids," Am. J. Respir. Crit. Care Med., 149, A215.

Depre, M., et al., (1994) "Pharmakokinetics and pharmacodynamics of multiple oral doses of MK-0591, a 5-lipoxygenase-activating protein inhibitor," Clin. Pharmacol. Ther., 56, 22-30.

Diamant, Z., et al., (1995) "The effect of MK-0591, a novel 5-lipoxygenase activating protein inhibitor, on leukotriene biosynthesis and allegen-induced airway response in asthmatic subjects in vivo," J Allergy Clin Immunol., 95, 42-51.

(Continued)

Primary Examiner — Paul Zarek

(74) Attorney, Agent, or Firm — Wilson, Sonsini, Goodrich & Rosati

(57) ABSTRACT

Described herein are methods for the synthesis of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, pharmaceutically acceptable salts, pharmaceutically acceptable solvates thereof. Also described are pharmaceutical compositions suitable for oral administration to a mammal that include, as well as methods of using such oral pharmaceutical compositions for treating respiratory conditions or diseases, as well as other leukotriene-dependent or leukotriene mediated conditions or diseases.

15 Claims, 8 Drawing Sheets

(56) References Cited

U.S. PATENT DOCUMENTS

| | | |
|---|---|---|
| 7,977,359 B2 | 7/2011 | Hutchinson et al. |
| 8,399,666 B2 | 3/2013 | Hutchinson et al. |
| 8,546,431 B2 | 10/2013 | Hutchinson et al. |
| 2001/0039037 A1 | 11/2001 | Harland |
| 2003/0203833 A1 | 10/2003 | Ignar et al. |
| 2004/0014759 A1 | 1/2004 | Picard et al. |
| 2004/0086952 A1 | 5/2004 | Gentz et al. |
| 2004/0198800 A1 | 10/2004 | Allan et al. |
| 2005/0245515 A1 | 11/2005 | Dehmlow et al. |
| 2006/0211677 A1 | 9/2006 | Chu et al. |
| 2007/0003971 A1 | 1/2007 | Blumenfeld et al. |
| 2007/0105866 A1 | 5/2007 | Hutchinson et al. |
| 2007/0123522 A1 | 5/2007 | Hutchinson et al. |
| 2007/0219206 A1 | 9/2007 | Hutchinson et al. |
| 2007/0225285 A1 | 9/2007 | Hutchinson et al. |
| 2007/0244128 A1 | 10/2007 | Hutchinson et al. |
| 2008/0227807 A1 | 9/2008 | Hutchinson et al. |
| 2008/0293739 A1 | 11/2008 | Trede |
| 2009/0018170 A1 | 1/2009 | Hutchinson et al. |
| 2009/0221574 A1 | 9/2009 | Hutchinson et al. |
| 2009/0291981 A1 | 11/2009 | Schaab et al. |
| 2011/0160249 A1 | 6/2011 | Schaab et al. |
| 2012/0220779 A1 | 8/2012 | Crawford et al. |
| 2013/0102636 A1 | 4/2013 | Hutchinson et al. |

FOREIGN PATENT DOCUMENTS

| | | |
|---|---|---|
| DE | 4338770 A1 | 5/1995 |
| EP | 419049 | 3/1991 |
| EP | 510398 | 10/1992 |
| EP | 0535924 A1 | 4/1993 |
| EP | 540051 | 5/1993 |
| EP | 0597112 A1 | 5/1994 |
| EP | 937459 | 8/1999 |
| EP | 1749829 | 2/2007 |
| FR | 2431491 | 2/1980 |
| GB | 2280181 | 1/1995 |
| JP | 6058881 | 3/1994 |
| JP | 6100551 | 4/1994 |
| JP | 3457694 | 8/1994 |
| JP | 7005651 | 1/1995 |
| JP | 8020532 | 1/1996 |
| JP | 9002977 | 1/1997 |
| JP | 11080032 | 3/1999 |
| JP | 11189531 | 7/1999 |
| JP | 11193265 | 7/1999 |
| JP | 2000007590 | 1/2000 |
| JP | 2000302671 | 10/2000 |
| JP | 2001139462 | 5/2001 |
| JP | 2002226429 | 8/2002 |
| JP | 2004262933 | 9/2004 |
| JP | 2005002346 | 1/2005 |
| JP | 2005082701 | 3/2005 |
| JP | 2005170939 | 6/2005 |
| JP | 2005194250 | 7/2005 |
| JP | 2009023986 | 2/2009 |
| WO | WO-88/02364 | 4/1988 |
| WO | WO-91-06537 A2 | 5/1991 |
| WO | WO-92/03132 | 3/1992 |
| WO | WO-93-16069 | 8/1993 |
| WO | WO-93-20065 A1 | 10/1993 |
| WO | WO-93/23391 | 11/1993 |
| WO | WO-93-25546 | 12/1993 |
| WO | WO-94/00446 | 1/1994 |
| WO | WO-94/11378 | 5/1994 |
| WO | WO-94/12179 | 6/1994 |
| WO | WO-94/13293 | 6/1994 |
| WO | WO-94/13662 | 6/1994 |
| WO | WO-94/14434 | 7/1994 |
| WO | WO-94/29290 | 12/1994 |
| WO | WO-95/06637 | 3/1995 |
| WO | WO-95/35372 | 12/1995 |
| WO | WO-96/03377 | 2/1996 |
| WO | WO-96/15118 | 5/1996 |
| WO | WO-96-18393 A1 | 6/1996 |
| WO | WO-96-32379 A1 | 10/1996 |
| WO | WO-96/35670 | 11/1996 |
| WO | WO-97/28105 | 8/1997 |
| WO | WO-97-41100 A1 | 11/1997 |
| WO | WO-97/49703 | 12/1997 |
| WO | WO-98/03202 | 1/1998 |
| WO | WO-98/21184 | 5/1998 |
| WO | WO-98/52943 | 11/1998 |
| WO | WO-98/56757 | 12/1998 |
| WO | WO-99/33458 | 7/1999 |
| WO | WO-99-33800 A1 | 7/1999 |
| WO | WO-99/43651 | 9/1999 |
| WO | WO-99/43672 | 9/1999 |
| WO | WO-00/29574 | 5/2000 |
| WO | WO-00/43384 | 7/2000 |
| WO | WO-01/32621 | 7/2000 |
| WO | WO-01/21594 | 3/2001 |
| WO | WO-01/36403 | 5/2001 |
| WO | WO-01/44184 | 5/2001 |
| WO | WO-01/41807 | 6/2001 |
| WO | WO-01-58869 A3 | 8/2001 |
| WO | WO-01/59105 | 8/2001 |
| WO | WO-01/64639 | 9/2001 |
| WO | WO-01/66520 | 9/2001 |
| WO | WO-01/70211 | 9/2001 |
| WO | WO-01/77149 | 10/2001 |
| WO | WO-02/00621 | 1/2002 |
| WO | WO-02/10152 | 2/2002 |
| WO | WO-02/28835 | 4/2002 |
| WO | WO-02/051397 | 7/2002 |
| WO | WO-02/051837 | 7/2002 |
| WO | WO-03/022813 | 3/2003 |
| WO | WO-03/022814 | 3/2003 |
| WO | WO-03/028719 | 4/2003 |
| WO | WO-03/035625 | 5/2003 |
| WO | WO 03-044014 A1 | 5/2003 |
| WO | WO-03/050174 | 6/2003 |
| WO | WO-03/094889 | 11/2003 |
| WO | WO-03/099771 | 12/2003 |
| WO | WO-04-000831 A1 | 12/2003 |
| WO | WO-2004/000795 | 12/2003 |
| WO | WO-2004/017917 | 3/2004 |
| WO | WO-2004/017920 | 3/2004 |
| WO | WO-2004/020409 | 3/2004 |
| WO | WO-2004/043392 | 5/2004 |
| WO | WO-2004/048331 | 6/2004 |
| WO | WO-2004/050643 | 6/2004 |
| WO | WO-2004/065388 | 8/2004 |
| WO | WO-2004/078719 | 9/2004 |
| WO | WO-2004/101554 | 11/2004 |
| WO | WO-2004/108671 | 12/2004 |
| WO | WO-2005/009951 | 2/2005 |
| WO | WO-2005/019381 | 3/2005 |
| WO | WO-2005/023246 | 3/2005 |
| WO | WO-2005/023806 | 3/2005 |
| WO | WO-2005-030717 A1 | 4/2005 |
| WO | WO-2005/054176 | 6/2005 |
| WO | WO-2005/054193 | 6/2005 |
| WO | WO-2005/054213 | 6/2005 |
| WO | WO-2005/065266 | 7/2005 |
| WO | WO-2005/066151 | 7/2005 |
| WO | WO-2005/066157 | 7/2005 |
| WO | WO-2005/082346 | 9/2005 |
| WO | WO-2005/097203 | 10/2005 |
| WO | WO-2005/112921 | 12/2005 |
| WO | WO-2005/123674 | 12/2005 |
| WO | WO-2006-014262 A3 | 2/2006 |
| WO | WO-2006/023843 | 3/2006 |
| WO | WO-2006/030031 | 3/2006 |
| WO | WO-2006/041961 | 4/2006 |
| WO | WO-2006/044602 | 4/2006 |
| WO | WO-2006/074984 | 7/2006 |
| WO | WO-2006/077364 | 7/2006 |
| WO | WO-2006/077365 | 7/2006 |
| WO | WO-2006/077366 | 7/2006 |
| WO | WO-2006/077367 | 7/2006 |
| WO | WO-2006/098912 | 9/2006 |
| WO | WO-2006/105439 | 10/2006 |

(56) References Cited

FOREIGN PATENT DOCUMENTS

| | | |
|---|---|---|
| WO | WO-2006-111560 A2 | 10/2006 |
| WO | WO-2006/131737 | 12/2006 |
| WO | WO-2007/022427 | 2/2007 |
| WO | WO-2007-047204 | 4/2007 |
| WO | WO-2007-047207 A2 | 4/2007 |
| WO | WO-2007/048042 | 4/2007 |
| WO | WO-2007/052123 | 5/2007 |
| WO | WO-2007/053094 | 5/2007 |
| WO | WO-2007/053095 | 5/2007 |
| WO | WO-2007-056021 A2 | 5/2007 |
| WO | WO-2007-056220 A2 | 5/2007 |
| WO | WO-2007-056228 A2 | 5/2007 |
| WO | WO-2007-064719 | 9/2007 |
| WO | WO-2007/109279 | 9/2007 |
| WO | WO-2007/123225 | 11/2007 |
| WO | WO-2008/058341 | 5/2008 |
| WO | WO-2008/067566 | 6/2008 |
| WO | WO-2008/097930 | 8/2008 |
| WO | WO-2008/127728 | 10/2008 |
| WO | WO-2008-137609 | 11/2008 |
| WO | WO-2008-137805 | 11/2008 |
| WO | WO-2008-141011 | 11/2008 |
| WO | WO-2009/002746 | 12/2008 |
| WO | WO-2009/009041 | 1/2009 |
| WO | WO-2009/045700 | 4/2009 |
| WO | WO-2009/055721 | 4/2009 |
| WO | WO-2009/114865 | 9/2009 |
| WO | WO-2010/068311 | 6/2010 |

OTHER PUBLICATIONS

Drazen, J. (1998) "Clinical pharmacology of leukotriene receptor antagonists and 5-lipoxygenase inhibitors," *Am. J. Respire. Crit. Care Med.*, 157, S233-S237.

Friedman et al., "Oral Leukotriene Inhibitor (MK-886) Blocks Allergen-Induced Airway Responses," ARRD 147:839 (1994).

Hakonarson H., et al., (2005) "Effects of a 5-lipoxygenase-activating protein inhibitor on biomarkers associated with risk of myocardial infarction: a randomized trial," J.A.M.A, 293, 2277-2279.

Hamilton et al., "Attenuation of early and late phase allergen-induced bronchoconstriction in asthmatic subjects by a 5-lipoxygenase activating protein antagonist, BAYx 1005," Thorax 52:348-354 (1997).

Hui et al., "Effect if a 5-lipoxygenase inhibitor on leukotriene generation and airway responses after allergen challenge in asthmatic patients," Thorax 46:184-189 (1991).

Jawien, J. et al., (2006) "Inhibition of five lipoxygenase activating protein (FLAP) by MK-886 decreases atherosclerosis in apoE/LDLR-double knockout mice," European Journal of Clinical Investigation 36 (3), 141-146.

Kemp JP., "Leukotriene receptor antagonists for the treatment of asthma", *IDrugs*. Apr. 2000;3(4):430-441.

Leff, A.R. et al., "Discovery of leukotrienes and development of antileukotriene agents,"Ann. Allergy Asthma Immunol. 86 (Suppl. 1):4-8 (2001).

Nasser et al., "Effect of the 5-lipoxygenase inhibitor ZD2138 on allergen-induced early and late asthmatic responses,"Thorax 49:743-748 (1994).

O'Byrne, P.M., "Leukotrines in the Pathogenesis of Asthma," Chest 111 (Supp.2):27S-34S (1997).

Riccioni, G. et al., "Brief Review. Advances in Therapy with Antileukotriene Drugs," Ann. Clin. Lab Sci. 34(4):379-387 (2004).

ScienceIP Search Report Jun. 2, 2006.

Science IP Search Report Jun. 15, 2007.

Uematsu, et al., (1995) "Pharmacokinetics and pharmacodynamic analysis of a novel leukotriene biosynthesis inhibitor," MK-0591, in healthy volunteers. *Br. J. Clin. Pharmacol.*, 40, 59-66.

Brooks,C.D.W. and Summers, J.B., "Modulators of Leukotriene Biosynthesis and Receptor Activation," J. Med. Chem. 39(14): 2629-2654 (1996).

Ford-Hutchinson, A.W. et al., "5-Lipoxygenase," Annu. Rev. Biochem. 63:383-417 (1994).

Frenett, R. et al., "Substituted Indoles as Potent and Orally Active 5-Lipoxygenase Activating Protein (FLAP) Inhibitors," Biorg. & Medicinal Chem. Ltrs. 9:2391-2396 (1996).

Miller, D.K. et al., "Identification and isolation of a membrane protein necessary for leukotriene production," Nature 343:278-281 (1990).

Rouzert, C.A. et al., "MK886, a Potent and Specific Leukotriene Biosynthesis Inhibitor Blocks and Reverses the Membrane Association of 5-Lipoxygenase in Ionophore-challenged Leukocytes," J. Biol. Chem. 265(1):1436-1442 (1990).

Woods, K.W. et al., "O-Alkylcarboxylate Oxime and N-Hydroxyurea Analogs of Substituted Indole Leukotriene Biosynthesis Inhibitors," Biorg. & Medicinal Chem. Ltrs. 6(13):1547-1552 (1996).

Young, R.N., "Inhibitors of 5-lipoxygenase: a therapeutic potential yet to be fully realized?" Eur. J. Med. Chem. 34:671-685 (1999).

U.S. Appl. No. 12/089,706, filed Apr. 9, 2008.

U.S. Appl. No. 12/092,570, filed May 2, 2008.

U.S. Appl. No. 11/925,841, filed Oct. 27, 2007.

U.S. Appl. No. 12/089,707, filed Oct. 1, 2008.

Bain, et al., "Pharmacodynamics and Pharmacokinetics of AM103, a Novel Inhibitor of 5-Lipoxygenase-Activating Protein (FLAP)." Clinical Pharmacology & Therapeutics 87, (Apr. 2010), p. 437-444.

Battersby, et al., "Biosynthesis of Porphyrins and Related Macrocycles. Part I. Synthesis of 14C-Labelled Pyrromethanes" Journal of the Chemical Society, Perkins Trans I; 1973; pp. 1546-1556.

Bernstein et al., "Polymorphism in Moleular Crystals", Oxford: Clarendon Press, 2002, p. 117, 118, 272 and 273.

Bhovi, et al., "Synthesis and Antimicrobial Activity of Some 1,5-Dioxadiazolyl/Ditriazolyland Dipyrrolylindole Derivatives" Asian Journal of Chemistry; 2005; vol. 17(1); p. 518-524.

Brinberg, et al "The Synthesis of 5-Aryl-pyrrolo[3, 2-b]pyridines and 7-Aryl-pyrrolo[3, 2-b] pyridines: Addition of 3- Aminopyrroles to Aryl Enaminones" Journal of Heterocyclic Chemistry; 1995; 32(4); p. 1293-1298.

Chemical & Engineering News, Feb. 2003, p. 32-35.

CMU Pharmaceutical polymorphism, internet, p. 1-3 (2002) (print out Apr. 3, 2008).

Concise Encyclopedia Chemistry, NY: Walter de Gruyter, 1993, p. 872-873.

Davidovich et al., "Detection of Polymorphism, etc.," American Pharmaceutical Review, IN: Russell Pub., 2004, 7(1), p. 10, 12, 14, 16 and 100.

Dunitz, "Are crystal structures predictable?" 2003; The Royal Society of Chemistry; Chem. Comm. ; p. 545-548.

EP 08842178.9 Extended European Search Report dated Sep. 6, 2011.

EP 08842178.9 Office action dated Sep. 12, 2012.

Evans, et al., "What's all the FLAP about?: 5-lipoxygenase-activating protein inhibitors for inflammatory diseases" Trends in Pharmaceutical Science; 2008; 29(2); p. 72-78.

Frydman, et al., "Synthesis of Substituted 4- and 6- Azaindoles" Journal of Organic Chemistry; 1968; 33(10); p. 3762-3766.

Gadaginamath, et al., "Chemoselective reaction of bisheterocycle dicarboxylate towards hydrazine hydrate: Synthesis and antimicrobial activity of some new trisheterocycles: 5-Pyrrolylaminocarbonylioxadiazolyl1 mercaptooxadiazolymethoxy-1-furfuryl-2-methylindoles"; 2003; Indian Journal of Chemistry; vol. 42B; p. 3108-3112.

Gardiner, et al , Inhibition of antigen-included contraction of guinea pig airways by a leukotriene synthesis inhibitor, BAY x1005; European Journal of Pharmacology; 1994; 258(1/2); p. 95-102.

Gillard, et al., "L-663,536 (MK-886) (341-(4-chlorobenzy1)-3-t-butyl-thio-5- isopropylindo1-2-y1]-2,2-dimethylpropanoic acid), a novel, orally active leukotriene biosynthesis inhibitor"; Canadian Journal of Physiol. Pharmac.; 1989; 67; p. 456-464.

Guasch, et al., "MK-591 acutely restores glomerular size selectivity and reduces proteinuria in human glomerulonephritis" Kidney International; 1999; 56; p. 261-267.

Guillard, et al., "Synthesis of New Melatonin Analogues from dimers of Azaindole and indole by use of Suzuki Homocoupling"Heterocycles; 2003; 60(4); p. 865-877.

(56) References Cited

OTHER PUBLICATIONS

Hutchinson, et al., "5-Lipoxygenase-Activating Protein Inhibitors: Development of 3-[3-tert-Butylsulfanyl-1-[4-(6-methoxy-pyridin-3-yl)-benzyl]-5-(pyridin-2-ylmethoxy)-1H-indol-2-yl]-2,2-dimethyl-propionic Acid (AM103)" J. Med. Chem; 2009; 52; p. 5803-5815.

Hutchinson, et al., "Development of L-689,065: The Prototype of a New Class of Potent 5-Lipoxygenase Inhibitors" Bioorganic & Medicinal Chemistry Letters; 1992 2(12); p. 1699-1702.

Hutchinson, et al., "Substituted Thiopyranol [2,3,4-c,d] indoles as Potent, Selective, and Orally Active Inhibitors of 5-Lipoxygenase. Synthesis and Biological Evaluation of L-691, 816" J. Med. Chem; 1993; 36; p. 2771-2787.

Jain et al., "Polymorphism in Pharmacy", Indian Drugs, 1986, 23(6), p. 315-329.

Larraya, et al., "Preparation of 4-Azaindoel and 7-Azaindole Dimers with a Bisalkoxyalkyl Spacer in order to Preferentially Target Melatonin MT1 Receptors over Melatonin MT2 receptors" European Journal of Medicinal Chemistry; 2004; 39(6); p. 515-526.

Lorrain, et al., "Pharmacological Characterization of 3-tert-Butylsulfanyl-144-(6- methoxy-pyridin-3-yl)-benzyl]-5-(pyridin-2-ylmethoxy)-1H-indol-2-yl]-2,2-dimethylpropionic Acid (AM103), a Novel Selective 5-Lipoxygenase-Activating Protein Inhibitor That Reduces Acute and Chronic Inflammation" The Journal of Pharmacology and Experimental Therapeutics; 2009; 331(3); p. 1042-1050.

Lorrain, et al., "Pharmacology of AM803, a novel selective five-lipoxygenase-activating protein (FLAP) inhibitor in rodent models of acute inflammation." European Journal of Pharmacology, 640 (2010), p. 211-218.

Musiyenko, et al. " A Novel 5-Lipoxygenase—Activating Protein Inhibitor, AM679, Reduces Inflammation in the Respiratory Syncytial Virus-Infected Mouse Eye." Clinical and Vaccine Immunology, Nov. 2009, p. 1654-1659.

Muzaffar et al., "Polymorphism and Drug Availability, etc.," J of Pharm. (Lahore), 1979, 1(1), p. 59-66.

OTUSKAet al., "Effect of Polymorphic, etc.," Chem. Pharm. Bull., 1999, 47(6) 852-856.

PCT/US2008/081190 Search Report mailed Jun. 26, 2009.

PCT/US2008/081190 International Preliminary Report on Patentability mailed Apr. 27, 2010.

Prasit, et al., "A New Class of Leukotriene Biosynthesis Inhibitors: The Discovery of MK0591"; Bioorganic & Medicinal Chemistry Letters; Nov 1, 1992; 2(11)); p. 1395-1398.

Rowland & Tozer, "Clinical Pharmacokinetics, etc.," 1995, p. 123.

Silverman, The Organic Chemistry of Drug Design and Drug Action, NY: Academic Press, 1993, p. 72-76.

Singhal et al., "Drug Polymorphism, etc.," Advanced Drug Delivery reviews 56 (2004) , p. 335-347.

Stock, et al. "5-Lipoxygenase-Activating Protein (FLAP) Inhibitors. Part 4: Development of 3-[3-tert-Butylsulfanyl-1{4-(6-ethoxypyridin-3-yl)benzyl]-5-(5-methylpyridin-2-ylmethoxy)-1H-indol-2-yl]-2,2-dimethylpropionic Acid (AM803), a Potent, Oral, Once Daily FLAP Inhibitor." J. Med. Chem., 2011, 54 (23), p. 8013-8029 (supplemental attachment—57 pages).

Stock, et al. , "5-Lipoxygenase-activating protein inhibitors. Part 2: 3-{5-((S)-1-Acetyl-2,3-dihydro-1H-indol-2-ylmethoxy)-3-tert-butylsulfanyl-1[4-(5-methoxy-pyrimidin-2-yl)-benzyl]-1H-indol-2-yl}-2,2-dimethyl-propionic acid (AM679)—A potent FLAP inhibitor." Bioorganic & Medicinal Chemistry Letters, vol. 20, Issue 1, Jan. 1, 2010, p. 213-217.

Stock, et al. " 5-Lipoxygenase-activating protein inhibitors. Part 3: 3-{3-tert-Butylsulfany-1-[4-(5-methoxy-pyrimidin-2-yl)-benzyl]-5-(5-methyl-pyridin-2-ylmethoxy)-1H-indol-2-yl]-2,2-dimethyl-propionic acid (AM643)—A potent FLAP inhibitor suitabe for topical adminsistration." Bioorganic & medicinal Chemistry Letter, vol. 20, Issue 15, Aug. 1, 2010, p. 4598-4601.

Suzuki, et al., "Sodium Telluride in N-Methyl-2-pyrrolidone. Reduction of Aromatic carbonyl Compounds to Alcohols and Formation of Pyrrolo[2, 3-d] pyrimidines (7-deaza-9H-purines) from Aromatic Nitriles" Journal of Organic Chemistry; 1993; 58(1); pp. 241-244.

Taday et al., "Using Terahertz, etc.," J of Pharm. Sci., 92(4), 2003, p. 831-838.

U.S. Pharmacopia #23, National Formulary #18, 1995, p. 1843-1844.

Ulicky. Comprehensive Dictionary of Physical Chemistry, NY: Prentice Hall, 1992, p. 21.

Vaananen, et al., "Pharmacological Investigation of the Role of Leukotrienes in the Pathogenesis of Experimental NSAID Gastropathy"; Inflammation; 1992; 16(3); pp. 227-240.

Valasinas, et al., "Synthesis of Porphobilinogen-9-14C" Journal of Labeled Compounds and Radiopharmaceuticals; 1978; 15(Suppl. vol.) pp. 549-554.

Whittle, et al., "Gastrointestinal Effects of Non-steroidal Anti-inflammatory Drugs'" Fundamental and Clinical Pharmacology; 2003; 17(3); p. 301-313.

* cited by examiner

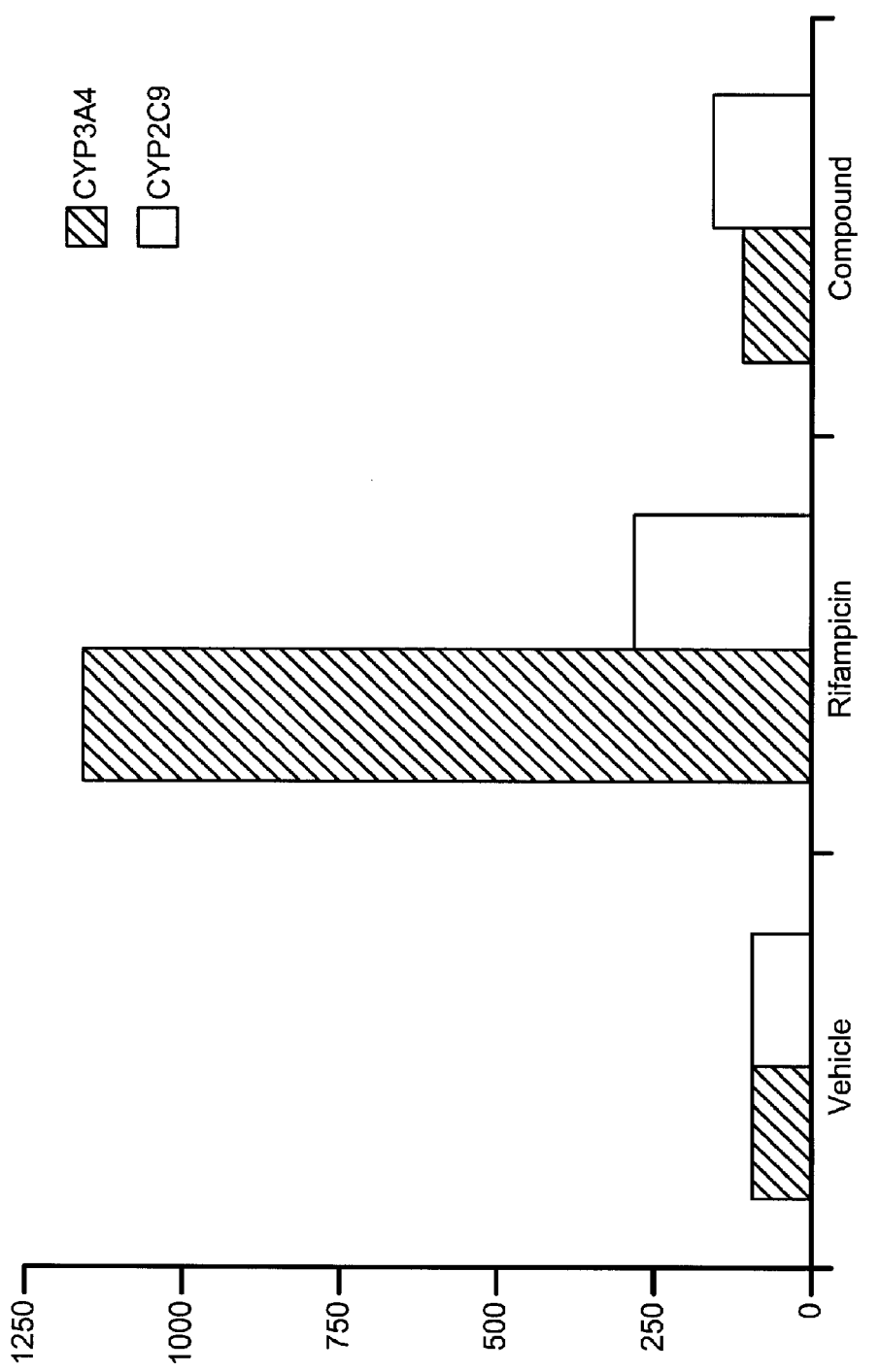

5-LIPOXYGENASE ACTIVATING PROTEIN (FLAP) INHIBITOR

RELATED APPLICATIONS

This application claims benefit of U.S. Provisional Application No. 60/983,119, entitled "ORAL FORMULATIONS FOR RESPIRATORY DISEASE" filed on Oct. 26, 2007; and U.S. Provisional Application No. 60/983,124, entitled "MANUFACTURING PROCESS AND POLYMORPHS OF 5-LIPOXYGENASE ACTIVATING PROTEIN INHIBITORS" filed on Oct. 26, 2007; each of which is herein incorporated by reference in their entirety.

FIELD OF THE INVENTION

Described herein is 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, and pharmaceutically acceptable salts, including pharmaceutically acceptable solvates thereof, as well as pharmaceutical compositions and methods of use thereof in the treatment or prevention of diseases or conditions associated with 5-lipoxygenase-activating protein (FLAP) activity.

BACKGROUND OF THE INVENTION

Leukotrienes are biological compounds formed from arachidonic acid in the leukotriene synthesis pathway. Leukotrienes are synthesized primarily by eosinophils, neutrophils, mast cells, basophils, dendritic cells, macrophages and monocytes. Leukotrienes have been implicated in biological actions including, by way of example only, smooth muscle contraction, leukocyte activation, cytokine secretion, mucous secretion, and vascular function.

FLAP is a member of the MAPEG (membrane associated proteins involved in eicosanoid and glutathione metabolism) family of proteins. FLAP is responsible for binding arachidonic acid and transferring it to 5-lipoxygenase. 5-Lipoxygenase can then catalyze the two-step oxygenation and dehydration of arachidonic acid, converting it into the intermediate compound 5-HPETE (5-hydroperoxyeicosatetraenoic acid), and in the presence of FLAP convert the 5-HPETE to Leukotriene $A_4$ ($LTA_4$).

$LTA_4$ is acted on by $LTC_4$ synthase, which conjugates $LTA_4$ with reduced glutathione (GSH) to form the intracellular product leukotriene $C_4$ ($LTC_4$). $LTC_4$ is transformed to leukotriene $D_4$ ($LTD_4$) and leukotrine $E_4$ ($LTE_4$) by the action of gamma-glutamyl-transpeptidase and dipeptidases. $LTC_4$ synthase plays a pivotal role as the only committed enzyme in the formation of cysteinyl leukotrienes.

SUMMARY OF THE INVENTION

Described herein is 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof, and methods of uses thereof in the treatment of leukotriene mediated diseases, disorders, or conditions. Also described are pharmaokinetic and pharmodynamic properties of such formulations in mammals, including humans.

Described herein are pharmaceutical compositions comprising: 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof as the active ingredient in the pharmaceutical composition; and at least one pharmaceutically acceptable inactive ingredient.

In one aspect, 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof is in an amorphous phase, a partially crystalline form, or a crystalline form.

In some embodiments, 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof is in an amorphous phase.

In other embodiments, 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof is in a crystalline form.

In one aspect, the pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid comprises the deprotonated form of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid as the anion, and the cation is a metal cation or an ammonium cation. In one aspect, the cation is selected from $Li^+$, $Na^+$, $K^+$, and $NH_4^+$. In one aspect, the cation is $Na^+$.

Pharmaceutical compositions described herein that include 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof are suitable for oral administration to a mammal. In one aspect, the pharmaceutical composition is in the form of a pill, capsule, tablet, aqueous solution, or aqueous suspension.

In one aspect, the pharmaceutical composition is in the form of a pill, capsule, or tablet. In one aspect, the pharmaceutical composition is in the form of an aqueous solution, or aqueous suspension.

In one aspect, the pharmaceutical composition comprises a detectable amount of palladium less than about 20 ppm. In one aspect, the pharmaceutical composition comprises a detectable amount of palladium less than about 10 ppm.

In one aspect, pharmaceutical compositions described herein include sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof. In one aspect, sodium 3-[5-(pyridin-2-ylmethoxy)-3-(2-methyl-2-propylthio)-1-[4-(2-methoxypyridin-5-yl)benzyl]indol-2-yl]-2,2-dimethyl-propionate or pharmaceutically acceptable solvate thereof is in an amorphous phase, a partially crystalline form, or a crystalline form.

Described herein are pharmaceutical compositions comprising: sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or a pharmaceutically acceptable solvate thereof, as the active ingredient in the pharmaceutical composition; and at least one pharmaceutically acceptable inactive ingredient.

In one aspect, pharmaceutical compositions described herein include 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof. In one aspect, 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid or a pharmaceutically acceptable solvate thereof is in an amorphous phase, a partially crystalline form, or a crystalline form. In specific embodiments, the pharmaceutical composition described herein is formulated as a tablet and 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof is in crystalline form. In specific embodiments, the pharmaceutical composition described herein is formulated as a tablet and 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof is in an amorphous phase.

In one aspect, the pharmaceutical composition is in the form of a tablet; and sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate is in a crystalline form. In one aspect, sodium 3-[5-(pyridin-2-ylmethoxy)-3-(2-methyl-2-propylthio)-1-[4-(2-methoxypyridin-5-yl)benzyl]indol-2-yl]-2,2-dimethyl-propionate is in a crystalline form having an X-ray diffraction pattern with characteristic deg 2-theta values of 3.84, 12.02, 16.72, 17.44, 18.26, 19.04, 19.84, 20.54, and 23.22. In another aspect, sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate is in a crystalline form having an X-ray diffraction pattern substantially the same as FIG. 1.

In another aspect, the pharmaceutical composition is in the form of a tablet; and sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate is in an amorphous phase.

In another aspect, sodium 3-[5-(pyridin-2-ylmethoxy)-3-(2-methyl-2-propylthio)-1-[4-(2-methoxypyridin-5-yl)benzyl]indol-2-yl]-2,2-dimethyl-propionate is in a crystalline form having an X-ray diffraction pattern with characteristic deg 2-theta values of 7.26, 9.12, 18.24, 18.98, 20.9, and 22.3. In one aspect, sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate is in a crystalline form having an X-ray diffraction pattern substantially the same as FIG. 2.

In one aspect, sodium 3-[5-(pyridin-2-ylmethoxy)-3-(2-methyl-2-propylthio)-1-[4-(2-methoxypyridin-5-yl)benzyl]

indol-2-yl]-2,2-dimethyl-propionate has a solubility in water at a pH of about 9.8 and about 25° C. of greater than about 50 mg/mL.

In some embodiments, the pharmaceutical composition comprises a detectable amount of a compound selected from:

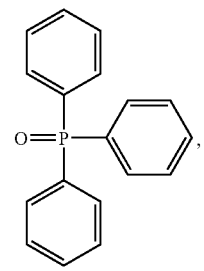

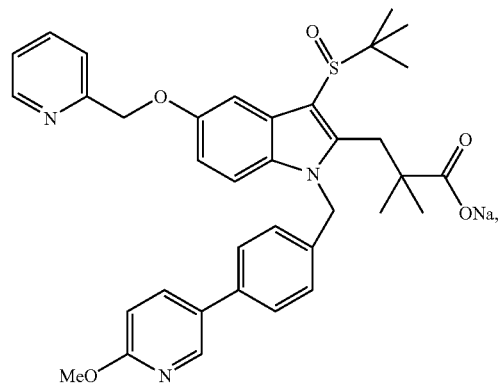

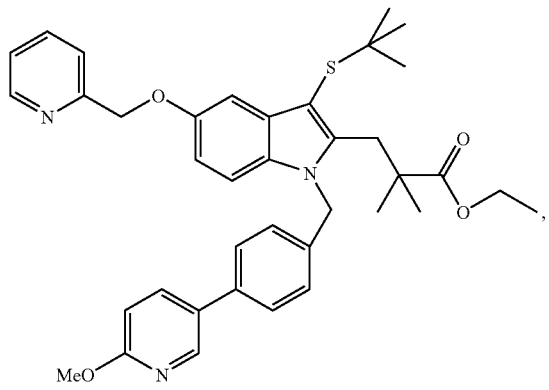

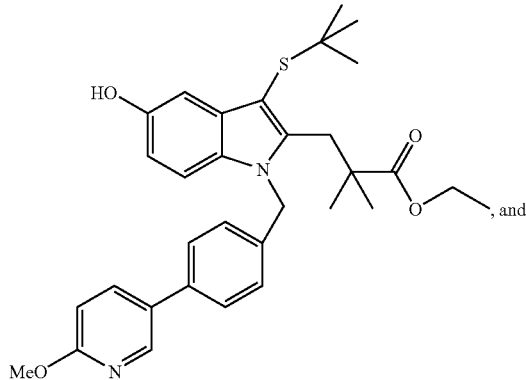

-continued

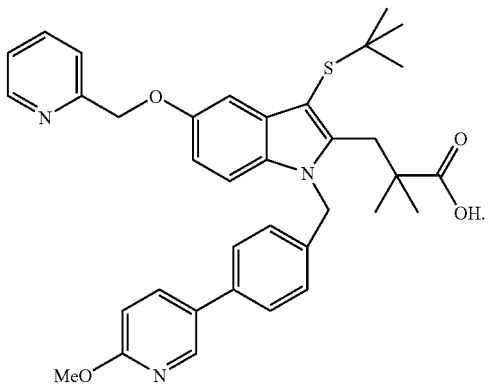

In one aspect, described herein is an oral pharmaceutical composition comprising: (a) an alkali metal salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof as the active ingredient in the oral pharmaceutical composition; (b) ethanol; and (c) an aqueous buffer solution. In one aspect, the alkali metal is sodium. In one aspect, the aqueous buffer solution is an aqueous sodium carbonate buffer solution. In another aspect, the oral pharmaceutical composition further comprises a pharmaceutically acceptable sweetener. In one aspect, the pharmaceutically acceptable sweetener is selected from aspartame, sucrose, sucralose, simple syrup, and syrpalta. In another aspect, the pharmaceutically acceptable sweetener is aspartame.

In one aspect, the oral pharmaceutical composition comprises a detectable amount of palladium that is less than about 10 ppm.

In one aspect, the oral pharmaceutical composition has a concentration of up to about 10 mg/mL of sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof.

In one aspect, the oral pharmaceutical composition includes: (a) about 1 gram of sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof; and (b) about 100 mL of about 10 mM aqueous sodium carbonate buffer solution with a pH of about 9-10 comprising about 10% w/w absolute ethanol and about 0.003% w/w aspartame.

In one aspect, a single dose of the oral pharmaceutical composition is administered to healthy adult human subjects in the fasted state. In one aspect, multiple doses of the oral pharmaceutical composition are administered to healthy adult human subjects in the fasted state.

In one aspect, a single dose of the pharmaceutical composition comprising from about 50 mg to about 1000 mg of the active ingredient when administered to healthy adult human subjects in the fasted state provides a $C_{max}$ of about 0.65 µM to about 13 µM, a $t_{max}$ of about 1 hour to about 3.5 hours, and an $AUC_{0-24}$ of about 5.4 hr*µM to about 85 hr*µM.

In one aspect, the single dose of the pharmaceutical composition when administered to healthy adult human subjects in the fasted state provides a $C_{max}$ that is less than about 9 µM.

In another aspect, the single dose of the oral pharmaceutical composition when administered to healthy adult human subjects in the fasted state provides after about 8 hours at least 80% reduction in blood $LTB_4$ levels and provides after about 24 hours at least 25% reduction in blood $LTB_4$ levels.

In another aspect, the single dose of the oral pharmaceutical composition when administered to healthy adult human subjects in the fasted state provides after about 24 hours at least 70% reduction in urinary $LTE_4$ levels.

In one aspect, the single dose of the oral pharmaceutical composition comprises about 50 mg to about 1000 mg of the active ingredient. In one aspect, the single dose of the oral pharmaceutical composition comprises about 50 mg, about 100 mg, about 150 mg, about 200 mg, about 300 mg, about 450 mg, about 500 mg, about 600 mg, about 700 mg, about 800 mg, about 900 mg, or about 1000 mg of the active ingredient.

In another aspect, described herein is an oral solid dosage form pharmaceutical composition comprising: (a) from about 25 mg to about 800 mg of sodium 3-[5-(pyridin-2-ylmethoxy)-3-(2-methyl-2-propylthio)-1-[4-(2-methoxypyridin-5-yl)benzyl]indol-2-yl]-2,2-dimethyl-propionate or pharmaceutically acceptable solvate thereof as the active ingredient in the composition; and (b) at least one inactive pharmaceutical ingredient.

In one aspect, the oral solid dosage form pharmaceutical composition comprises about 25 mg to about 1000 mg of sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof.

In another aspect, the oral solid dosage form pharmaceutical composition comprises about 50 mg to about 600 mg of sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof.

In yet another aspect, the oral solid dosage form pharmaceutical composition comprises about 100 mg to about 400 mg of sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof.

In one aspect, the oral solid dosage form pharmaceutical composition comprises about 25 mg, about 50 mg, about 100 mg, about 150 mg, about 200 mg, about 250 mg, about 300 mg, about 350 mg, 400 mg, 450 mg, or about 500 mg of sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof.

In one aspect, the oral solid dosage form pharmaceutical composition comprises a detectable amount of palladium that is less than about 10 ppm.

In one aspect, the oral solid dosage form pharmaceutical comprises a detectable amount of ethyl acetate that is less than about 5000 ppm.

In one aspect, the oral solid dosage form pharmaceutical composition comprises a detectable amount of ethanol that is less than about 5000 ppm.

In some embodiments, the oral solid dosage form pharmaceutical composition comprises a detectable amount of a compound selected from:

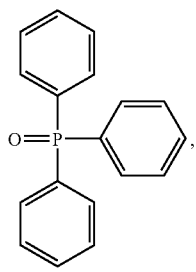

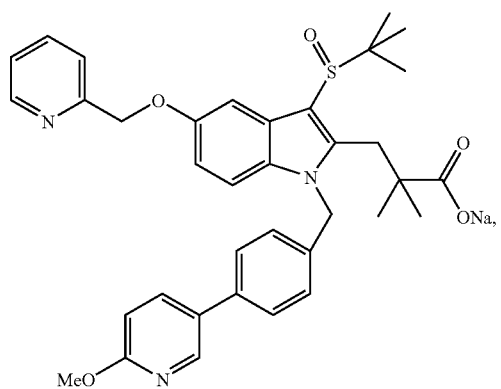

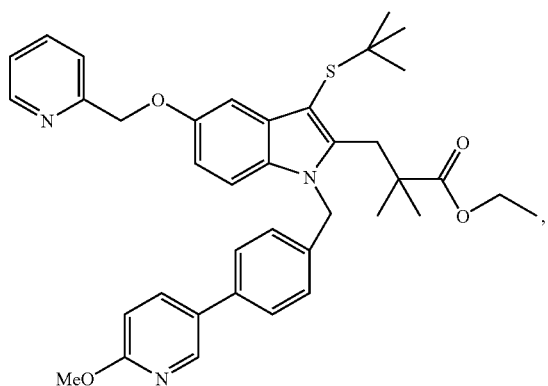

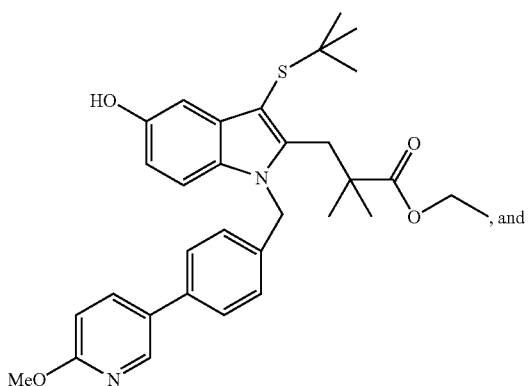, and

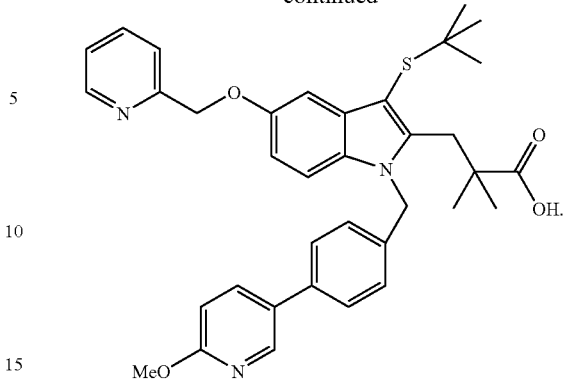

In any of the oral solid dosage form pharmaceutical compositions described herein, sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof is in a crystalline form, a partially crystalline form, or an amorphous phase.

In one aspect of the oral solid dosage form pharmaceutical compositions described herein sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof is in a crystalline form. In one aspect, sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof is in a crystalline form having an X-ray diffraction pattern with characteristic deg 2-theta values of 3.84, 12.02, 16.72, 17.44, 18.26, 19.04, 19.84, 20.54, and 23.22. In another aspect, sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof is in a crystalline form having an X-ray diffraction spectrum substantially the same as FIG. 1.

In another aspect of the oral solid dosage form pharmaceutical compositions described herein, sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof is in a crystalline form having an X-ray diffraction pattern with characteristic deg 2-theta values of 7.26, 9.12, 18.24, 18.98, 20.9, and 22.3. In another aspect, sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof is in a crystalline form having an X-ray diffraction spectrum substantially the same as FIG. 2.

In another aspect of the oral solid dosage form pharmaceutical compositions described herein, sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof is in an amorphous phase.

In one aspect, oral solid dosage form pharmaceutical compositions described herein that include 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof, allow for rapid absorption of the active ingredient in the upper gastrointestinal tract.

In one aspect, oral solid dosage form pharmaceutical compositions described herein that include sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof, allow for rapid absorption of the active ingredient in the upper gastrointestinal tract. In one aspect, the upper gastrointestinal tract includes the stomach. In another aspect, the upper gastrointestinal tract includes the stomach and the duodenum. In another aspect, the upper gastrointestinal tract includes the stomach and the small intestine.

In one aspect, the oral solid dosage form pharmaceutical composition is in the form of a tablet. In one aspect, the oral solid dosage form pharmaceutical composition is in the form of an immediate release tablet.

In another aspect, the oral solid dosage form pharmaceutical composition exhibits an in vitro release of the active ingredient in about 1% sodium lauryl sulfate solution at pH of about 7.0 and about 37° C. of about 100% after about 10 minutes. In one aspect, the in vitro release is measured by a drug release test using the United States Pharmacopea (USP) Apparatus 1 (rotating basket) at about 100 rpm with about 500 mL of about 1% sodium lauryl sulfate solution at pH of about 7.0 and about 37° C.

In one aspect, the oral solid dosage form pharmaceutical compositions described herein that include sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof when administered as a single dose to healthy adult human subjects in the fasted state provides a $C_{max}$ less than about 5 µM, and provides after about 8 hours at least 80% reduction in blood $LTB_4$ levels.

In one aspect, the oral solid dosage form pharmaceutical compositions described herein that include sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof when administered as a single dose to healthy adult humans in the fasted state provides after about 24 hours at least 30% reduction in blood $LTB_4$ levels.

In one aspect, the oral solid dosage form pharmaceutical compositions described herein that include sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof when administered as a single dose to healthy adult human subjects in the fasted state provides after about 24 hours at least 80% reduction of urinary $LTE_4$ levels.

In one aspect, the oral solid dosage form pharmaceutical compositions described herein comprise inactive pharmaceutical ingredients selected from binding agents, disintegrants, and glidants. In one aspect, the inactive pharmaceutical ingredients comprise silicified microcrystalline cellulose (SMCC), mannitol, crospovidone, and magnesium stearate.

In one aspect, the oral solid dosage form pharmaceutical compositions described herein comprise from about 10% by weight to about 20% by weight of sodium 3-[5-(pyridin-2-ylmethoxy)-3-(2-methyl-2-propylthio)-1-[4-(2-methoxypyridin-5-yl)benzyl]indol-2-yl]-2,2-dimethyl-propionate or pharmaceutically acceptable solvate thereof. In another aspect, the oral solid dosage form pharmaceutical compositions described herein comprise more than about 20% by weight of sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof.

In one aspect, pharmaceutical compositions described herein provide at least one metabolite of 3-[3-tert-butylsulfanyl-1-[4-(6-methoxy-pyridin-3-yl)-benzyl]-5-(pyridin-2-ylmethoxy)-1H-indol-2-yl]-2,2-dimethyl-propionic acid after administration to a mammal. In one aspect, the least one metabolite is selected from among: 3-[3-tert-butylsulfanyl-1-[4-(6-hydroxy-pyridin-3-yl)-benzyl]-5-(pyridin-2-ylmethoxy)-1H-indol-2-yl]-2,2-dimethyl-propionic acid; 3-[1-[4-(6-methoxy-pyridin-3-yl)-benzyl]-3-(2-methyl-propane-2-sulfonyl)-5-(pyridin-2-ylmethoxy)-1H-indol-2-yl]-2,2-dimethyl-propionic acid; 3-[1-[4-(6-methoxy-pyridin-3-yl)-benzyl]-3-(2-methyl-propane-2-sulfinyl)-5-(pyridin-2-ylmethoxy)-1H-indol-2-yl]-2,2-dimethyl-propionic acid; 3-[3-tert-butylsulfanyl-1-[4-(6-methoxy-pyridin-3-yl)-benzyl]-5-(1-oxy-pyridin-2-ylmethoxy)-1H-indol-2-yl]-2,2-dimethyl-propionic acid; and the acyl gluconuride of 3-[3-tert-butylsulfanyl-1-[4-(6-methoxy-pyridin-3-yl)-benzyl]-5-(pyridin-2-ylmethoxy)-1H-indol-2-yl]-2,2-dimethyl-propionic acid.

In another aspect, the least one metabolite is the acyl gluconuride of 3-[3-tert-butylsulfanyl-1-[4-(6-methoxy-pyridin-3-yl)-benzyl]-5-(pyridin-2-ylmethoxy)-1H-indol-2-yl]-2,2-dimethyl-propionic acid.

In one aspect, described herein are pharmaceutical compositions for oral administration to a mammal that comprises an active ingredient that inhibits 5-lipoxygenase-activating protein (FLAP) and does not inhibit at least one Cytochrome P450 enzyme selected from CYP 3A4, CYP 1A2, CYP 2A6, CYP 2B6, CYP 2C8, CYP 2C9, CYP 2C19, CYP 2D6, and CYP 2E1 at doses up to 50 µM. In one aspect, described herein are pharmaceutical compositions for oral administration to a mammal that comprises an active ingredient that inhibits 5-lipoxygenase-activating protein (FLAP) and does not inhibit at least one Cytochrome P450 enzyme selected from CYP 3A4, CYP 1A2, and CYP 2D6 at doses up to 50 µM. In one aspect, the pharmaceutical composition does not induce Cytochrome P450 CYP 3A4 or CYP 2C9 at doses up to 50 µM. In another aspect, the pharmaceutical composition does not induce Cytochrome P450 CYP 3A4 or CYP 2C9 at doses up to 10 µM. In one aspect, the active ingredient is 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof. In another aspect, the active ingredient is sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof.

In one aspect, described herein are pharmaceutical compositions for oral administration to a mammal that comprises an active ingredient that inhibits 5-lipoxygenase-activating protein (FLAP) and does not substantially cause increases in liver weight of the mammal. In one aspect, the active ingredient is 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof. In another aspect, the active ingredient is sodium 3-[5-(pyridin- 2-ylmethoxy)-3-(2-methyl-2-propylthio)-1-[4-(2-methoxypyridin-5-yl)benzyl]indol-2-yl]-2,2-dimethyl-propionate or a pharmaceutically acceptable solvate thereof.

In one aspect, described herein is an oral solid dosage form pharmaceutical composition comprising: a) 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl) benzyl]-indol-2-yl]-2,2-dimethyl-propionic acid or pharmaceutically acceptable solvate thereof; and b) optionally at least one inactive pharmaceutical ingredient.

In one aspect, the oral solid dosage form pharmaceutical composition comprises: a) sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof as the active ingredient in the composition; and b) optionally at least one inactive pharmaceutical ingredient.

In some embodiments, the oral solid dosage form pharmaceutical composition is in the form of a capsule.

In some embodiments, the capsule are hard gelatine capsules.

In one aspect, sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate or pharmaceutically acceptable solvate thereof, is amorphous, partially crystalline, or crystalline.

The oral solid dosage form pharmaceutical composition of claim 78, wherein:
sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate or pharmaceutically acceptable solvate thereof is crystalline.

In some embodiments, the capsule comprises at least one excipient.

In other embodiments, the capsule does not comprise an excipient.

Also described are articles of manufacture comprising multiple unit doses of the oral solid dosage form pharmaceutical compositions described herein in a high-density polyethylene (HDPE) bottle equipped with a high-density polyethylene (HDPE) cap. In one aspect, the article of manufacture further comprises an aluminum foil induction seal and silica gel desiccant.

In one aspect, described herein is a method of treating asthma in a human comprising administering to the human an oral pharmaceutical composition described herein that includes 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof, as the active ingredient the oral pharmaceutical composition. In another aspect, the active ingredient is sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof.

In one aspect, described herein is an oral pharmaceutical composition comprising 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof, as the active ingredient for the treatment of asthma in a human. In another aspect, the active ingredient is sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof.

In another aspect, described herein is a method of preventing exercise-induced bronchoconstriction in a human who is otherwise susceptible to bronchoconstriction when exercising comprising administering to the human an oral pharmaceutical composition that includes 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid or pharmaceutically acceptable solvate thereof, as the active ingredient the oral pharmaceutical composition. In another aspect, the active ingredient is sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof.

In another aspect, described herein is an oral pharmaceutical composition comprising 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof, as the active ingredient for the prevention of exercise-induced bronchoconstriction in a human. In a further aspect, the active ingredient is sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof.

In one aspect, described herein is a method of treating allergic rhinitis in a human comprising administering to the human an oral pharmaceutical composition that includes 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof, as the active ingredient in the oral pharmaceutical composition. In another aspect, the active ingredient is sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof.

In another aspect, described herein is an oral pharmaceutical composition comprising 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof, as the active ingredient for the treatment of allergic rhinitis in a human. In a further aspect, the active ingredient is sodium 3-[5-(pyridin-2-ylmethoxy)-3-(2-methyl-2-propylthio)-1-[4-(2-methoxypyridin-5-yl)

benzyl]-indol-2-yl]-2,2-dimethyl-propionate or pharmaceutically acceptable solvate thereof.

In any of the method of treatments described herein, the methods may further comprise administering at least one additional pharmaceutical agent selected from inhaled corticosteroids, short acting beta-agonists, long acting beta-agonists, antihistamines, non-steroidal glucocorticoid receptor (GR) agonists, anticholinergics, antiinfective and antivirals.

In one aspect, described herein is a method of treating chronic obstructive pulmonary disease in a human comprising administering to the human a pharmaceutical composition that includes 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof, as the active ingredient in the oral pharmaceutical composition. In another aspect, the active ingredient is sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or a pharmaceutically acceptable solvate thereof.

In another aspect, described herein is an oral pharmaceutical composition comprising 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof, as the active ingredient for the treatment of chronic obstructive pulmonary disease in a human. In a further aspect, the active ingredient is sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or a pharmaceutically acceptable solvate thereof.

In one aspect, described herein is a method of treating cardiovascular disease in a human comprising administering to the human a pharmaceutical composition that includes 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof, as the active ingredient in the oral pharmaceutical composition. In another aspect, the active ingredient is sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or a pharmaceutically acceptable solvate thereof.

In another aspect, described herein is an oral pharmaceutical composition comprising 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof, as the active ingredient for the treatment of cardiovascular disease in a human. In a further aspect, the active ingredient is sodium 3-[5-(pyridin-2-ylmethoxy)-3-(2-methyl-2-propylthio)-1-[4-(2-methoxypyridin-5-yl)benzyl]indol-2-yl]-2,2-dimethyl-propionate or a pharmaceutically acceptable solvate thereof.

In one aspect, described herein is a method of treating pain in a human comprising administering to the human a pharmaceutical composition that includes 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid or pharmaceutically acceptable solvate thereof, as the active ingredient in the oral pharmaceutical composition. In another aspect, the active ingredient is sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or a pharmaceutically acceptable solvate thereof.

In another aspect, described herein is an oral pharmaceutical composition comprising 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof, as the active ingredient for the treatment of pain in a human. In a further aspect, the active ingredient is sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or a pharmaceutically acceptable solvate thereof. In one aspect, the pain is acute pain or chronic pain. In one aspect, the pain is nociceptive pain, neuropathic pain, inflammatory pain, or non-inflammatory pain. In one aspect, the pain is central pain or peripheral pain. In one aspect, the pain is peripheral neuropathic pain.

In one embodiment, 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof, are used to treat patients suffering from leukotriene-dependent conditions or diseases, including, but not limited to, asthma, chronic obstructive pulmonary disease, pulmonary hypertension, interstitial lung fibrosis, allergic rhinitis, adult respiratory distress syndrome, and inflammatory conditions.

In another aspect are methods for modulating, including reducing and/or inhibiting the activity of 5-lipoxygenase activating protein, directly or indirectly, in a mammal comprising administering to the mammal at least once an effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof.

In another aspect are methods for modulating, including reducing and/or inhibiting, the activity of leukotrienes in a mammal, directly or indirectly, comprising administering to the mammal at least once an effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof.

In another aspect are methods for treating leukotriene-dependent or leukotriene mediated conditions or diseases, comprising administering to the mammal at least once an effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof.

In another aspect are methods for treating inflammation comprising administering to a mammal at least once an effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof.

In another aspect are methods for treating pain comprising administering to a mammal at least once an effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof.

In another aspect, described herein is an oral formulation comprising 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof, as the active ingredient for the treatment of inflammation in a human. In a further aspect, the active ingredient is sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof.

In another aspect are methods for treating respiratory diseases comprising administering to the mammal at least once an effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof. In a further embodiment of this aspect, the respiratory disease is asthma. In a further embodiment of this aspect, the respiratory disease includes, but is not limited to, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, allergic rhinitis, vasomotor rhinitis, vascular responses, endotoxic shock, fibrogenesis, pulmonary fibrosis, allergic diseases, chronic inflammation and adult respiratory distress syndrome.

In another aspect are methods for treating chronic obstructive pulmonary disease comprising administering to the mammal at least once an effective amount of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid, including pharmaceutically acceptable salts, and pharmaceutically acceptable solvates thereof. In a further embodiment of this aspect, chronic obstructive pulmonary disease includes, but is not limited to, chronic bronchitis or emphysema, pulmonary hypertension, interstitial lung fibrosis and/or airway inflammation and cystic fibrosis.

In another aspect are methods for preventing increased mucosal secretion and/or edema in a disease or condition that would otherwise result in increased mucosal secretion and/or edema comprising administering to the mammal at least once an effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof.

In another aspect are methods for treating eosinophil and/or basophil and/or dendritic cell and/or neutrophil and/or monocyte recruitment comprising administering to the mammal at least once an effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof. In another aspect are methods for preventing eosinophil and/or basophil and/or dendritic cell and/or neutrophil and/or monocyte recruitment in a patient that is otherwise susceptible to eosinophil and/or basophil and/or dendritic cell and/or neutrophil and/or monocyte recruitment comprising administering to the patient at least once an effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof.

In another aspect are methods for treating ocular inflammation and allergic conjunctivitis, vernal keratoconjunctivitis, and papillary conjunctivitis comprising administering to the mammal at least once an effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof. In another aspect are methods for preventing ocular inflammation and allergic conjunctivitis, vernal keratoconjunctivitis, and papillary conjunctivitis in a patient that is otherwise susceptable to ocular inflammation and allergic conjunctivitis, vernal keratoconjunctivitis, and papillary conjunctivitis comprising administering to the patient at least once an effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof.

In another aspect are methods for treating acute or chronic disorders involving recruitment or activation of eosinophils comprising administering to the mammal at least once an effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof.

In another aspect are methods for treating NSAID-induced gastric lesions comprising administering to the mammal at least once an effective amount of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid, including pharmaceutically acceptable salts, and pharmaceutically acceptable solvates thereof. In another aspect are methods for preventing NSAID-induced gastric lesions in a patient that is otherwise susceptible to gastric lesions when provided with NSAIDS comprising administering to the patient at least once an effective amount of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid, including pharmaceutically acceptable salts, and pharmaceutically acceptable solvates thereof.

In any of the aforementioned aspects are further embodiments in which the mammal is a human, including embodiments wherein (a) the human has an asthmatic condition or one or more other condition(s) selected from the group consisting of allergic (extrinsic) asthma, non-allergic (intrinsic)

asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, or seasonal asthma, or chronic obstructive pulmonary disease, or pulmonary hypertension or interstitial lung fibrosis. In any of the aforementioned aspects are further embodiments in which the mammal is an animal model for pulmonary inflammation, examples of which are provided herein.

In any of the aforementioned aspects are further embodiments comprising single administrations of the effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof, including further embodiments in which 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid, including pharmaceutically acceptable salts, and pharmaceutically acceptable solvates thereof is (i) administered once-a-day; (ii) is administered twice-a-day; or (iii) is administered multiple times over the span of one day.

In any of the aforementioned aspects are further embodiments comprising multiple administrations of the effective amount of the compound, including further embodiments in which (i) the compound is administered in a single dose; (ii) the time between multiple administrations is every 6 hours; (iii) the compound is administered to the mammal every 8 hours.

In further or alternative embodiments, the method comprises a drug holiday, wherein the administration of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof is temporarily suspended or the dose being administered is temporarily reduced; at the end of the drug holiday dosing is resumed. In one embodiment, the length of the drug holiday varies from 2 days to 1 year.

In one aspect, 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof are used in the manufacture of medicaments for the treatment of leukotriene dependent conditions, disorders, or diseases in a human that is a non-responder to montelukast. In one aspect, the leukotriene dependent condition, disorder, or disease is a respiratory disease or condition. In one aspect, the respiratory disease or condition is asthma.

In one aspect, described herein is the treatment of leukotriene dependent conditions, diseases, or disorders in a human that is a non-responder to montelukast. In one aspect, the leukotriene dependent condition, disorder, or disease is a respiratory disease or condition. In one aspect, the respiratory disease or condition is asthma.

In one aspect, the dose of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof, that is administered to healthy human patients is reduced in human patients that lack or have a defect in a UDP-glucuronosyltransferase enzyme normally present in the human.

In one aspect, described herein is a method of increasing the bioavailability of an orally administered dose of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof, in healthy human patients comprising orally administering to a mammal: (1) a dose of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof; and (2) an inhibitor of a UDP-glucuronosyltransferase enzyme normally present in the mammal. In one aspect, the UDP-glucuronosyltransferase enzyme is selected from UGT1A1, UGT1A3, UGT1A6, UGT1A9, and UGT2B7.

In any of the aforementioned aspects involving the prevention or treatment of inflammation are further embodiments comprising: (a) monitoring inflammation in a mammal; (b) measuring bronchoconstriction in a mammal; (c) measuring eosinophil and/or basophil and/or dendritic cell and/or neutrophil and/or monocyte and/or lymphocyte recruitment in a mammal; (d) monitoring mucosal secretion in a mammal; (e) measuring mucosal edema in a mammal; (e) measuring levels of $LTB_4$ in the calcium ionophore-challenged blood of a mammal; (f) measuring levels of $LTE_4$ in the urinary excretion of a mammal; or (g) identifying a patient by measuring leukotriene-driven inflammatory biomarkers such as $LTB_4$, $LTC_4$, Il-6, CRP, SAA, MPO, EPO, MCP-1, MIP-$\alpha$, sICAMs, Il-4, Il-13.

In any of the aforementioned aspects involving the prevention or treatment of leukotriene-dependent or leukotriene mediated diseases or conditions are further embodiments comprising identifying patients by screening for a leukotriene gene haplotype. In further or alternative embodiments the leukotriene gene haplotype is a leukotriene pathway gene, while in still further or alternative embodiments, the leukotriene gene haplotype is a 5-lipoxygenase-activating protein (FLAP) haplotype.

In any of the aforementioned aspects involving the prevention or treatment of leukotriene-dependent or leukotriene mediated diseases or conditions are further embodiments comprising identifying patients by monitoring the patient for either:

i) at least one leukotriene related inflammatory biomarker; or ii) at least one functional marker response to a leukotriene modifying agent; or iii) at least one leukotriene related inflammatory biomarker and at least one functional marker response to a leukotriene modifying agent.

In further or alternative embodiments, the leukotriene-related inflammatory biomarkers are selected from the group consisting of $LTB_4$, cysteinyl leukotrienes, CRP, SAA, MPO, EPO, MCP-1, MIP-$\alpha$, sICAM, IL-6, IL-4, and IL-13, while in still further or alternative embodiments, the functional marker response is significant lung volume (FEV1).

In any of the aforementioned aspects involving the prevention or treatment of leukotriene-dependent or leukotriene mediated diseases or conditions are further embodiments comprising identifying patients by either:

i) screening the patient for at least one leukotriene gene SNP and/or haplotype including SNP's in intronic or exonic locations; or ii) monitoring the patient for at least one leukotriene related inflammatory biomarker; or iii) monitoring the patient for at least one functional marker response to a leukotriene modifying agent In further or alternative embodiments, the leukotriene gene SNP or haplotype is a leukotriene pathway gene. In still further or alternative embodiments, the leukotriene gene SNP or haplotype is a 5-lipoxygenase-activating protein (FLAP) SNP or haplotype. In further or alternative embodiments, the leukotriene-related inflammatory biomarkers are selected from the group consisting of $LTB_4$, cysteinyl leukotrienes, CRP, SAA, MPO, EPO, MCP-1, MIP-α, sICAM, IL-6, IL-4, and IL-13, while in still further or alternative embodiments, the functional marker response is significant lung volume (FEV1).

In any of the aforementioned aspects involving the prevention or treatment of leukotriene-dependent or leukotriene mediated diseases or conditions are further embodiments comprising identifying patients by at least two of the following:
 i) screening the patient for at least one leukotriene gene SNP or haplotype;
 ii) monitoring the patient for at least one leukotriene related inflammatory biomarker;
 iii) monitoring the patient for at least one functional marker response to a leukotriene modifying agent.

In further or alternative embodiments, the leukotriene gene SNP or haplotype is a leukotriene pathway gene. In still further or alternative embodiments, the leukotriene gene SNP or haplotype is a 5-lipoxygenase-activating protein (FLAP) SNP or haplotype. In further or alternative embodiments, the leukotriene-related inflammatory biomarkers are selected from the group consisting of $LTB_4$, cysteinyl leukotrienes, CRP, SAA, MPO, EPO, MCP-1, MIP-α, sICAM, IL-6, IL-4, and IL-13, while in still further or alternative embodiments, the functional marker response is significant lung volume (FEV1).

In any of the aforementioned aspects involving the prevention or treatment of leukotriene-dependent or leukotriene mediated diseases or conditions are further embodiments comprising identifying patients by:
 i) screening the patient for at least one leukotriene gene SNP or haplotype; and
 ii) monitoring the patient for at least one leukotriene related inflammatory biomarker; and
 iii) monitoring the patient for at least one functional marker response to a leukotriene modifying agent.

In further or alternative embodiments, the leukotriene gene SNP or haplotype is a leukotriene pathway gene. In still further or alternative embodiments, the leukotriene gene SNP or haplotype is a 5-lipoxygenase-activating protein (FLAP) SNP or haplotype. In further or alternative embodiments, the leukotriene-related inflammatory biomarkers are selected from the group consisting of $LTB_4$, cysteinyl leukotrienes, CRP, SAA, MPO, EPO, MCP-1, MIP-α, sICAM, IL-6, IL-4, and IL-13, while in still further or alternative embodiments, the functional marker response is significant lung volume (FEV1).

In another aspect is the prevention or treatment of leukotriene-dependent or leukotriene mediated diseases or conditions comprising administering to a patient an effective amount of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance, wherein the patients has been identified using information obtained by:
 i) screening the patient for at least one leukotriene gene SNP or haplotype; and
 ii) monitoring the patient for at least one leukotriene related inflammatory biomarker; and
 iii) monitoring the patient for at least one functional marker response to a leukotriene modifying agent.

In further or alternative embodiments, the leukotriene gene SNP or haplotype is a leukotriene pathway gene. In still further or alternative embodiments, the leukotriene gene SNP or haplotype is a 5-lipoxygenase-activating protein (FLAP) SNP or haplotype. In further or alternative embodiments, the leukotriene-related inflammatory biomarkers are selected from the group consisting of $LTB_4$, cysteinyl leukotrienes, CRP, SAA, MPO, EPO, MCP-1, MIP-α, sICAM, IL-6, IL-4, and IL-13, while in still further or alternative embodiments, the functional marker response is significant lung volume (FEV1). In further or alternative embodiments, the information obtained from the three diagnostic methods are used in an algorithm in which the information is analyzed to identify patients in need of treatment with a FLAP modulator, the treatment regimen, and the type of FLAP modulator used.

In any of the aforementioned aspects the leukotriene-dependent or leukotriene mediated diseases or conditions include, but are not limited to, asthma, chronic obstructive pulmonary disease, pulmonary hypertension, interstitial lung fibrosis, rhinitis, allergy, adult respiratory distress syndrome.

In one aspect, described is a pharmaceutical composition comprising 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof for treating asthma in a human.

In one aspect, described is a pharmaceutical composition comprising 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof for preventing or limiting the onset of exercise-induced bronchoconstriction in a human that is otherwise susceptible to exercise-induced bronchoconstriction.

In one aspect, described is a pharmaceutical composition comprising 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof for treating allergic rhinitis in a human.

In one aspect, described is a pharmaceutical composition comprising 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof for treating chronic obstructive pulmonary disease in a human.

In one aspect, described is a pharmaceutical composition comprising 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof for treating cardiovascular disease in a human.

In one aspect, described is a pharmaceutical composition comprising 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof for treating NSAID-indused gastric lesions in a human.

In one aspect, described is a pharmaceutical composition comprising 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof for treating pain in a human.

In one aspect, described is a pharmaceutical composition comprising 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof for treating any of the diseases, disorders, or conditions that are presented herein. In one aspect, described is a pharmaceutical composition comprising 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid or a pharmaceutically acceptable solvate thereof, or a pharmaceutically acceptable salt of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid or pharmaceutically acceptable solvate thereof for preventing (or minimizing the onset of) any of the diseases, disorders, or conditions that are presented herein, wherein the human is otherwise susceptible to such disease, disorder or condition.

In one aspect, the pharmaceutically acceptable salt of 3-[(5-pyridin-2ylmethoxy)-3-(2-methyl-2-propylthio)-1-[4-(2-methoxypyridin-5-yl)benzyl]-indol-2-yl]-2,2-dimethyl-propionic acid is sodium 3-[(5-pyridin-2ylmethoxy)-3-(2-methyl-2-propylthio)-1-[4-(2-methoxypyridin-5-yl)benzyl]-indol-2-yl]-2,2-dimethyl-propionate.

In one aspect, described is a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof for treating asthma in a human.

In one aspect, described is a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof for preventing exercise-induced bronchoconstriction in a human.

In one aspect, described is a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof for treating allergic rhinitis in a human.

In one aspect, described is a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof for treating chronic obstructive pulmonary disease in a human.

In one aspect, described is a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof for treating cardiovascular disease in a human.

In one aspect, described is a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof for treating NSAID-indused gastric lesions in a human.

In one aspect, described is a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof for treating pain in a human.

In one aspect, described is 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid or pharmaceutically acceptable solvate thereof for treating asthma, preventing exercise-induced bronchoconstriction, treating allergic rhinitis, treating chronic obstructive pulmonary disease, treating cardiovascular disease, treating NSAID-indused gastric lesions, or for treating pain in a human. In one aspect, 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof is in a crystalline form. In one aspect, 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof is in an amorphous phase.

In one aspect, described is a pharmaceutically acceptable salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof for treating or preventing any of the diseases, disorders or conditions presented herein.

In one aspect, the pharmaceutically acceptable salt of 3-[(5-pyridin-2ylmethoxy)-3-(2-methyl-2-propylthio)-1-[4-(2-methoxypyridin-5-yl)benzyl]-indol-2-yl]-2,2-dimethyl-propionic acid is sodium 3-[(5-pyridin-2ylmethoxy)-3-(2-methyl-2-propylthio)-1-[4-(2-methoxypyridin-5-yl)benzyl]-indol-2-yl]-2,2-dimethyl-propionate.

In one aspect, described is a pharmaceutically acceptable salt of 3-[(5-pyridin-2ylmethoxy)-3-(2-methyl-2-propylthio)-1-[4-(2-methoxypyridin-5-yl)benzyl]-indol-2-yl]-2,2-dimethyl-propionic acid or pharmaceutically acceptable solvate thereof.

In one aspect, the pharmaceutically acceptable salt comprises 3-[(5-pyridin-2ylmethoxy)-3-(2-methyl-2-propylthio)-1-[4-(2-methoxypyridin-5-yl)benzyl]indol-2-yl]-2,2-dimethyl-propionate as the anion, and a cation selected from $Na^+$, $K^+$, $Ca^{2+}$, $NH_4^+$, the protonated form of dicyclohexylamine, the protonated form of N-methyl-D-glucamine, the protonated form of tris(hydroxymethyl)methylamine, the protonated form of arginine, and the protonated form of lysine. In one aspect, the pharmaceutically acceptable salt comprises 3-[(5-pyridin-2ylmethoxy)-3-(2-methyl-2-propylthio)-1-[4-(2-methoxypyridin-5-yl)benzyl]-indol-2-yl]-2,2-dimethyl-propionate as the anion, and $Na^+$ as the cation.

In one aspect is a pharmaceutically acceptable salt having the following structure:

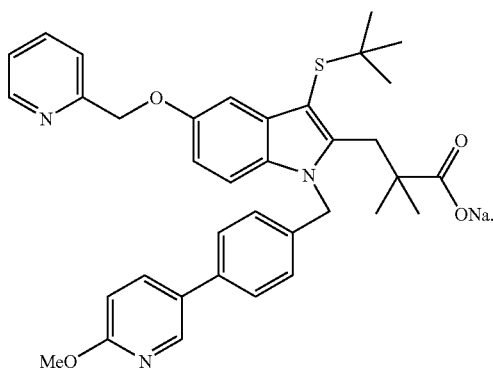

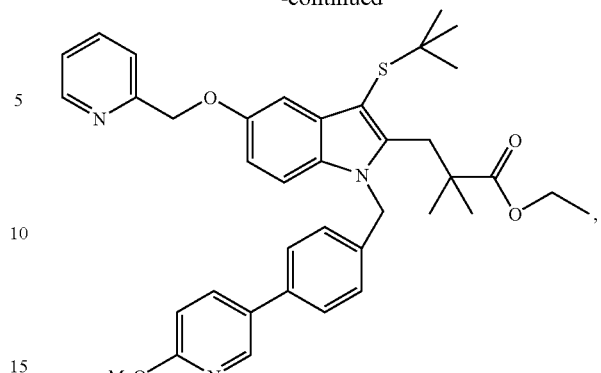

In one aspect, the pharmaceutically acceptable salt is in an amorphous phase.

In another aspect, the pharmaceutically acceptable salt is in a crystalline form.

In one aspect, the pharmaceutically acceptable salt is in a crystalline form and has an X-ray powder diffraction pattern (XRPD) substantially similar to that shown in FIG. 1.

In one aspect, the pharmaceutically acceptable salt comprises a detectable amount of water.

In one aspect, the pharmaceutically acceptable salt comprises a detectable amount of an organic solvent. In one instance, the organic solvent is selected from ethyl acetate, isopropyl acetate, tert-butylmethylether, heptane, isopropanol, and ethanol.

In some embodiments, the pharmaceutically acceptable salt comprises a detectable amount of palladium.

In one aspect, the pharmaceutically acceptable salt comprises a detectable amount of palladium that is less than 20 ppm.

In some embodiments, the pharmaceutically acceptable salt comprises a detectable amount of a compound selected from:

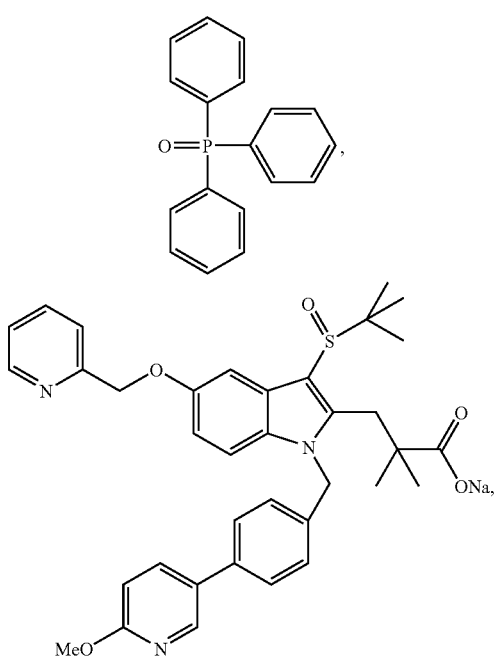

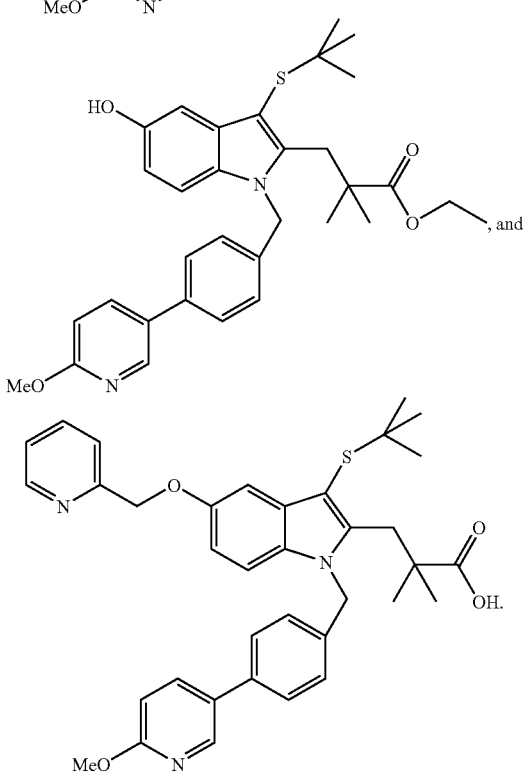

In one aspect, pharmaceutically acceptable salt comprises an organic solvent in the crystal lattice. In some embodiments, the organic solvent is a Class 3 solvent. In one aspect, the Class 3 solvent is selected from ethyl acetate, isopropyl acetate, tert-butylmethylether, heptane, isopropanol, or ethanol. In one aspect, pharmaceutically acceptable salt comprises ethanol in the crystal lattice.

In one aspect, pharmaceutically acceptable salt is in a desolvated form.

In one instance, provided is a pharmaceutically acceptable salt comprising 3-[(5-pyridin-2ylmethoxy)-3-(2-methyl-2-propylthio)-1-[4-(2-methoxypyridin-5-yl)benzyl]-indol-2-yl]-2,2-dimethyl-propionate as the anion and a cation is selected from $Na^+$, $K^+$, $Li^+$, $Ca^{2+}$, $NH_4^+$, the protonated form of dicyclohexylamine, the protonated form of N-methyl-D-glucamine, the protonated form of tris(hydroxymethyl)methylamine, the protonated form of arginine, and the protonated form of lysine, or pharmaceutically acceptable solvate thereof wherein the pharmaceutically acceptable salt is in an amorphous phase.

In another instance, provided is a crystalline form of sodium 3-[(5-pyridin-2ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof.

In one aspect, the crystalline form is solvated with a Class 3 solvent selected from ethyl acetate, isopropyl acetate, tert-butylmethylether, heptane, isopropanol, and ethanol. In one aspect, the crystalline form is solvated with ethanol.

In one aspect, the crystalline form has an X-ray diffraction pattern with characteristic deg 2Θ values of 7.2, 9.1, 18.2, 18.9, 20.9, and 22.3.

In another aspect, the crystalline form has substantially the same X-ray diffraction pattern as shown in FIG. 2.

In one aspect, the crystalline form is in a desolvated form.

In one aspect, the crystalline form has an X-ray diffraction pattern with characteristic deg 2Θ values of 12.0, 17.4, 18.2, 19.0, 20.5, and 23.2.

In one aspect, the crystalline form has substantially the same X-ray diffraction pattern as shown in FIG. 1.

Also described is a composition comprising sodium 3-[(5-pyridin-2ylmethoxy)-3-(2-methyl-2-propylthio)-1-[4-(2-methoxypyridin-5-yl)benzyl]-indol-2-yl]-2,2-dimethyl-propionate or pharmaceutically acceptable solvate thereof as a solid, wherein the composition comprises a detectable amount of palladium that is less than about 20 ppm. In one aspect, the composition comprises a detectable amount of palladium that is less than about 10 ppm. In some embodiments, the composition comprises a detectable amount of palladium that is less than about 5 ppm. In other embodiments, the composition comprises a detectable amount of a compound selected from:

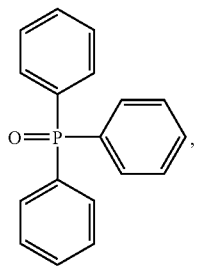

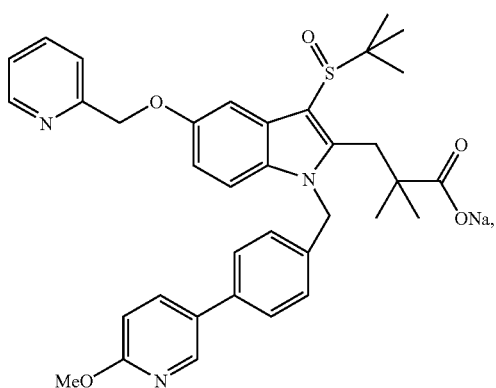

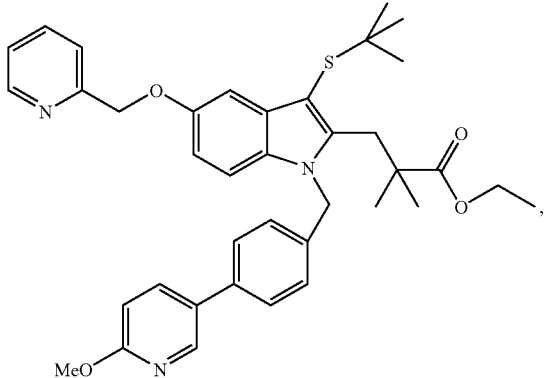

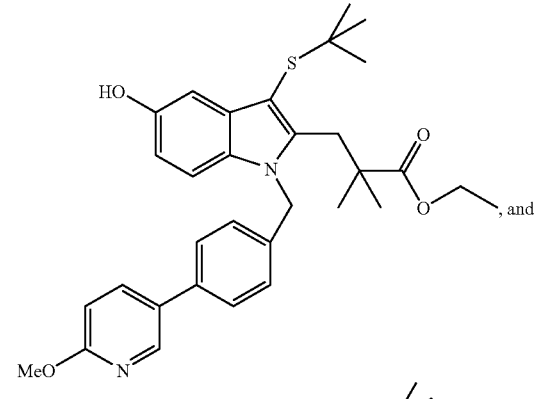

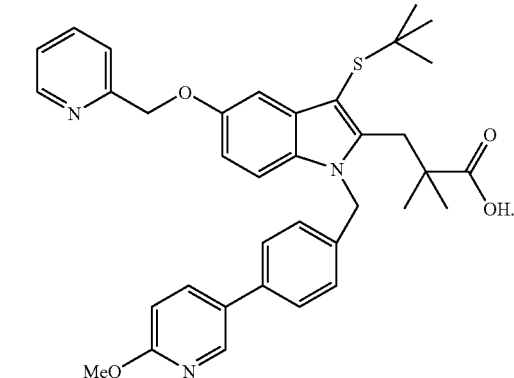

In some embodiments, sodium 3-[(5-pyridin-2yl-methoxy)-3-(2-methyl-2-propylthio)-1-[4-(2-methoxypyridin-5-yl)benzyl]indol-2-yl]-2,2-dimethyl-propionate or pharmaceutically acceptable solvate thereof is in a crystalline form.

In some embodiments, sodium 3-[(5-pyridin-2yl-methoxy)-3-(2-methyl-2-propylthio)-1-[4-(2-methoxypyridin-5-yl)benzyl]indol-2-yl]-2,2-dimethyl-propionate is in a crystalline form and solvated with a Class 3 solvent selected from ethyl acetate, isopropyl acetate, tert-butylmethylether, heptane, isopropanol, and ethanol.

In some embodiments, sodium 3-[(5-pyridin-2yl-methoxy)-3-(2-methyl-2-propylthio)-1-[4-(2-methoxypyridin-5-yl)benzyl]indol-2-yl]-2,2-dimethyl-propionate is in a crystalline form and solvated with ethanol.

In some embodiments, sodium 3-[(5-pyridin-2yl-methoxy)-3-(2-methyl-2-propylthio)-1-[4-(2-methoxypyridin-5-yl)benzyl]indol-2-yl]-2,2-dimethyl-propionate is in a crystalline form and is desovated.

In one aspect, sodium 3-[(5-pyridin-2ylmethoxy)-3-(2-methyl-2-propylthio)-1-[4-(2-methoxypyridin-5-yl)benzyl]- indol-2-yl]-2,2-dimethyl-propionate or pharmaceutically acceptable solvate thereof is in a amorphous phase.

In one aspect, described is a composition comprising sodium 3-[(5-pyridin-2ylmethoxy)-3-(2-methyl-2-propylthio)-1-[4-(2-methoxypyridin-5-yl)benzyl]-indol-2-yl]-2,2-dimethyl-propionate as a solid, wherein the composition comprises a detectable amount of solvent, wherein the solvent is selected from 1,2-dimethoxyethane, ethyl acetate, methanol, ethanol, acetonitrile, tetrahydrofuran, 2-propanol, heptane, tert-butylmethylether, and water.

In one aspect, described is a composition comprising sodium 3-[(5-pyridin-2ylmethoxy)-3-(2-methyl-2-propylthio)-1-[4-(2-methoxypyridin-5-yl)benzyl]-indol-2-yl]-2,2-dimethyl-propionate, wherein the solubility of sodium 3-[(5-pyridin-2ylmethoxy)-3-(2-methyl-2-propylthio)-1-[4-(2-methoxypyridin-5-yl)benzyl]-indol-2-yl]-2,2-dimethyl-propionate in water at a pH of about 9 at about 25° C. is greater than about 9 mg/mL.

Also provided is a process for the preparation of a crystalline form of sodium 3-[(5-pyridin-2ylmethoxy)-3-(2-methyl-2-propylthio)-1-[4-(2-methoxypyridin-5-yl)benzyl]-indol-2-yl]-2,2-dimethyl-propionate comprising the step of recrystallizing sodium 3-[(5-pyridin-2ylmethoxy)-3-(2-methyl-2-propylthio)-1-[4-(2-methoxypyridin-5-yl)benzyl]-indol-2-yl]-2,2-dimethyl-propionate from ethyl acetate.

Described in one embodiment is a crystalline form of sodium 3-[(5-pyridin-2ylmethoxy)-3-(2-methyl-2-propylthio)-1-[4-(2-methoxypyridin-5-yl)benzyl]-indol-2-yl]-2,2-dimethyl-propionate prepared by recrystallizing sodium 3-[(5-pyridin-2ylmethoxy)-3-(2-methyl-2-propylthio)-1-[4-(2-methoxypyridin-5-yl)benzyl]-indol-2-yl]-2,2-dimethyl-propionate from ethyl acetate.

In one aspect, a crystalline form of sodium 3-[(5-pyridin-2ylmethoxy)-3-(2-methyl-2-propylthio)-1-[4-(2-methoxypyridin-5-yl)benzyl]-indol-2-yl]-2,2-dimethyl-propionate prepared by recrystallizing sodium 3-[(5-pyridin-2ylmethoxy)-3-(2-methyl-2-propylthio)-1-[4-(2-methoxypyridin-5-yl)benzyl]-indol-2-yl]-2,2-dimethyl-propionate from ethanol.

In one aspect, described is a process for the preparation of sodium 3-[(5-pyridin-2ylmethoxy)-3-(2-methyl-2-propylthio)-1-[4-(2-methoxypyridin-5-yl)benzyl]-indol-2-yl]-2,2-dimethyl-propionate comprising the steps of:

(i) reacting a compound of Formula (I):

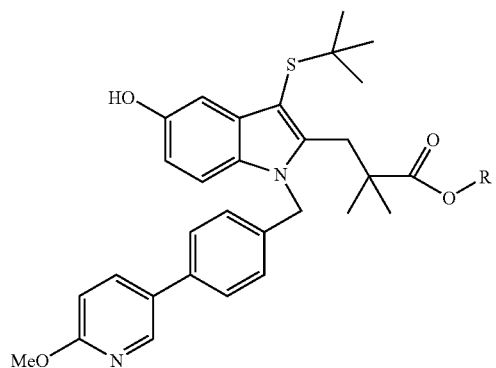

Formula (I)

wherein R is $C_1$-$C_6$ alkyl;

with a compound of Formula (II):

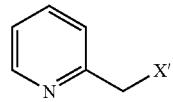

Formula (II)

wherein X' is a leaving group;
in the presence of a base in a suitable solvent to form a compound of Formula (III):

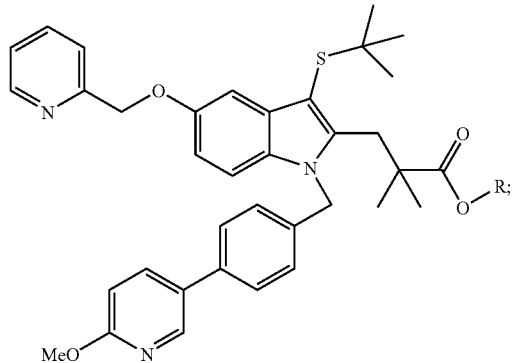

Formula (III)

and
(ii) forming a sodium salt of the product of step (i).
In one aspect, R is —$CH_3$ or —$CH_2CH_3$. In another aspect, R is —$CH_2CH_3$.

In one aspect, the base is a cesium base, potassium base or a sodium base. In another aspect, the base is a cesium base.

In some embodiments, X' is selected from —Cl, —Br, —I, —$OSO_2CF_3$, —$OSO_2$(4-methylphenyl), —$OSO_2$(phenyl) and —$OSO_2CH_3$. In a certain embodiment, X' is —Cl.

In one aspect, step (i) further comprises heating to a temperature of about 50° C. to about 90° C.

In other embodiments, step (i) further comprises isolating the compound of Formula (III) from step (i).

In one aspect, the compound of Formula (I) comprises a detectable amount of palladium and isolating the product of step (i) further comprises a means for reducing the amount of palladium.

In some embodiments, step (ii) comprises hydrolysis of the ester moiety of the compound of Formula (III) from step (i).

In one aspect, step (ii) comprises: a) treatment of the compound of Formula (III) from step (i) with LiOH, KOH, or Ca(OH)$_2$, followed by pH adjustment, followed by treatment with NaOH; or b) treatment of the compound of Formula (III) from step (i) with NaOH.

In some embodiments, step (ii) comprises treatment of the compound of Formula (III) of step (i) with LiOH, followed by pH adjustment, followed by treatment with NaOH.

In certain embodiments, step (ii) comprises treatment of the compound of Formula (III) from step (i) with NaOH.

In one aspect, step (ii) is performed in a solution comprising tetrahydrofuran, water, and an alcohol selected from methanol and ethanol. In another aspect, step (ii) is performed in a solution comprising ethanol and water.

In one aspect, the compound of Formula (I) is prepared by: reacting a compound of formula (IV):

Formula (IV)

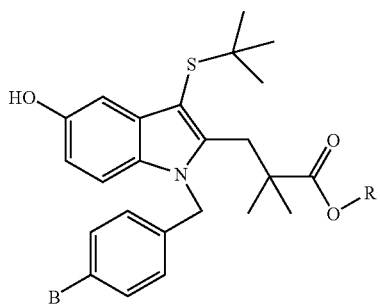

wherein R is $C_1$-$C_6$ alkyl; and B is a boronic acid or boronate ester;
with a compound of Formula (V):

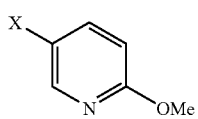

Formula (V)

wherein X is a leaving group,
in the presence of a first coupling catalyst in a suitable solvent, to form a compound of Formula (I):

Formula (I)

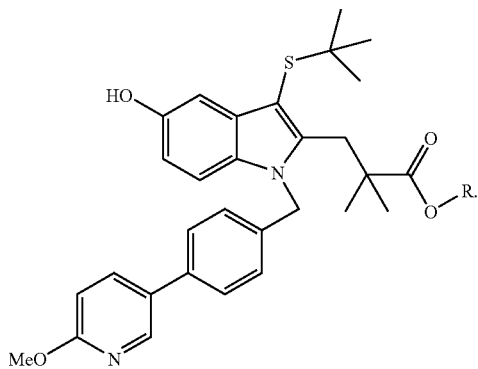

In another embodiment is a processes for the preparation of a compound of Formula (I) comprising reacting a compound of formula (X):

Formula (X)

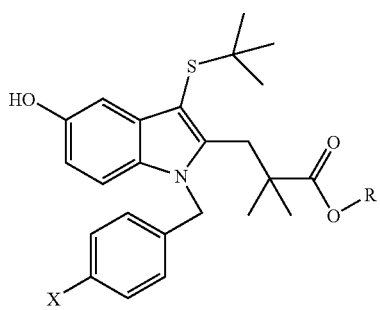

wherein R is $C_1$-$C_6$ alkyl; and X is a leaving group;

with a compound of Formula (XI):

Formula (XI)

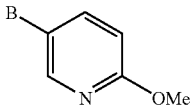

wherein B is a boronic acid or boronate ester,
in the presence of a first coupling catalyst and base in a suitable solvent to form a compound of Formula (I).

In some embodiments, X is selected from —Cl, —Br, —I, —OSO$_2$CF$_3$, —OSO$_2$(4-methylphenyl), and —OSO$_2$CH$_3$.
In one aspect, X is —Br.
In some embodiments, B is selected from

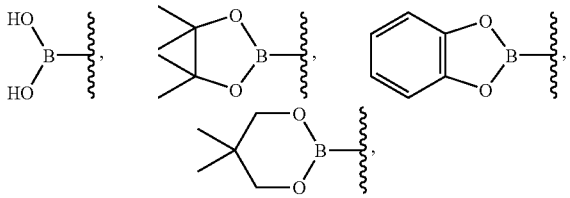

and

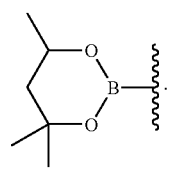 [SMILES: *B1OC(C)CC(C)(C)O1]

In one aspect, B is

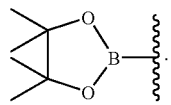 [SMILES: *B1OC(C)(C)C(C)(C)O1]

In some embodiments, the first coupling catalyst is a palladium catalyst. In some embodiments, the palladium catalyst is Pd(PPh$_3$)$_4$.

In one aspect, the reaction further comprises heating to a temperature of about 60° C. to about 95° C.

In some embodiments, the compound of Formula (IV) is prepared by reacting a compound of Formula (VI):

Formula (VI)

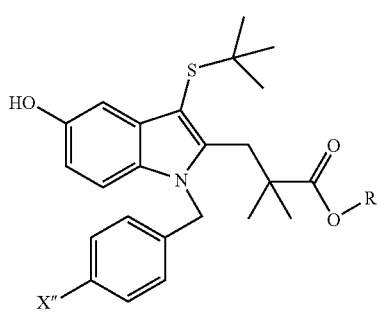

wherein X" is a leaving group; and R is —C$_1$-C$_6$ alkyl;

with a borylation reagent, in the presence of a second coupling catalyst in a suitable solvent to provide a compound of Formula (IV):

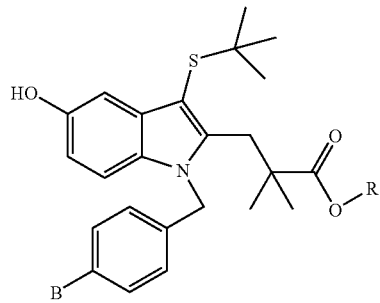

Formula (IV)

wherein R is —C$_1$-C$_6$ alkyl; and B is a boronic acid or boronate ester.

In some embodiments, X" is selected from —Cl, —Br, —I, —OSO$_2$CF$_3$, —OSO$_2$(4-methylphenyl), and —OSO$_2$CH$_3$. In one embodiment, X" is —Br.

In one aspect, the borylation reagent is selected from pinacolborane, catecholborane, bis(neopentyl glycolato)diboron, bis(pinacolato)diboron, bis(hexylene glycolato)diboron, and bis(catecholato)diboron. In one embodiment, the borylation reagent is bis(pinacolato)diboron.

In one aspect, the second coupling catalyst is a palladium catalyst. In one embodiment, the palladium catalyst is Pd(dppf)Cl$_2$.

In one aspect, the first coupling catalyst is the same as the second coupling catalyst.

In one aspect, the first coupling catalyst is not the same as the second coupling catalyst.

In one aspect, the reaction further comprises heating to a temperature of about 60° C. to about 95° C.

In one embodiment, the compound of Formula (VI) is prepared by:
(a) reacting a compound of Formula (VII):

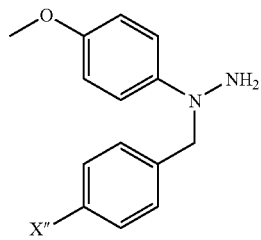

Formula (VII)

wherein X" is a leaving group;
with a compound of Formula (VIII) in a suitable solvent:

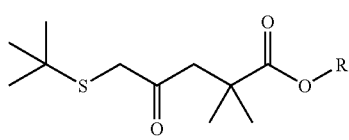

Formula (VIII)

wherein R is C$_1$-C$_6$ alkyl;

to form a compound of Formula (IX):

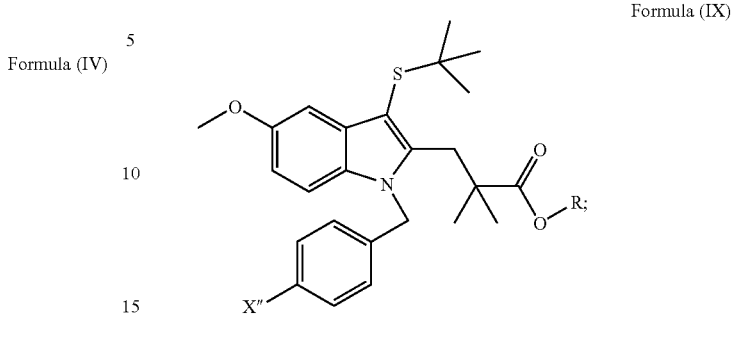

Formula (IX)

and
(b) demethylating the compound of Formula (IX) from step (i) to form a compound of Formula (VI):

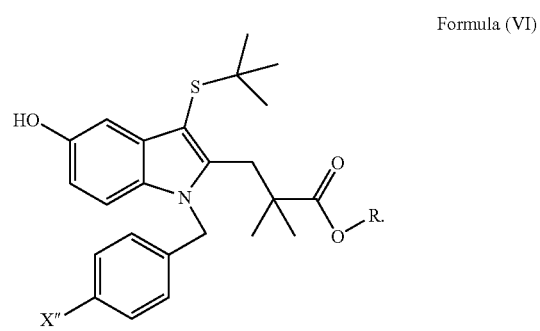

Formula (VI)

In one aspect, step (a) is performed in a suitable solvent at a temperature of about 10° C. to about 35° C.

In some embodiments, X" is selected from —Br, —Cl, and —I. In one embodiment, X" is —Br.

In some embodiments, R is —CH$_3$ or —CH$_2$CH$_3$. In one embodiment, R is —CH$_2$CH$_3$.

In some embodiments, step (b) comprises reacting the compound of Formula (IX) from step (a) with 2-methyl-2-propanethiol and AlCl$_3$ in a suitable solvent.

In one aspect, sodium 3-[(5-pyridin-2ylmethoxy)-3-(2-methyl-2-propylthio)-1-[4-(2-methoxypyridin-5-yl)benzyl]-indol-2-yl]-2,2-dimethyl-propionate comprises a detectable amount of palladium.

In one aspect, sodium 3-[(5-pyridin-2ylmethoxy)-3-(2-methyl-2-propylthio)-1-[4-(2-methoxypyridin-5-yl)benzyl]indol-2-yl]-2,2-dimethyl-propionate comprises a detectable amount of a compound selected from:

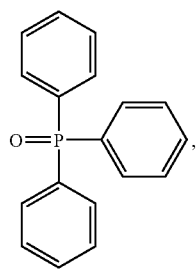

-continued

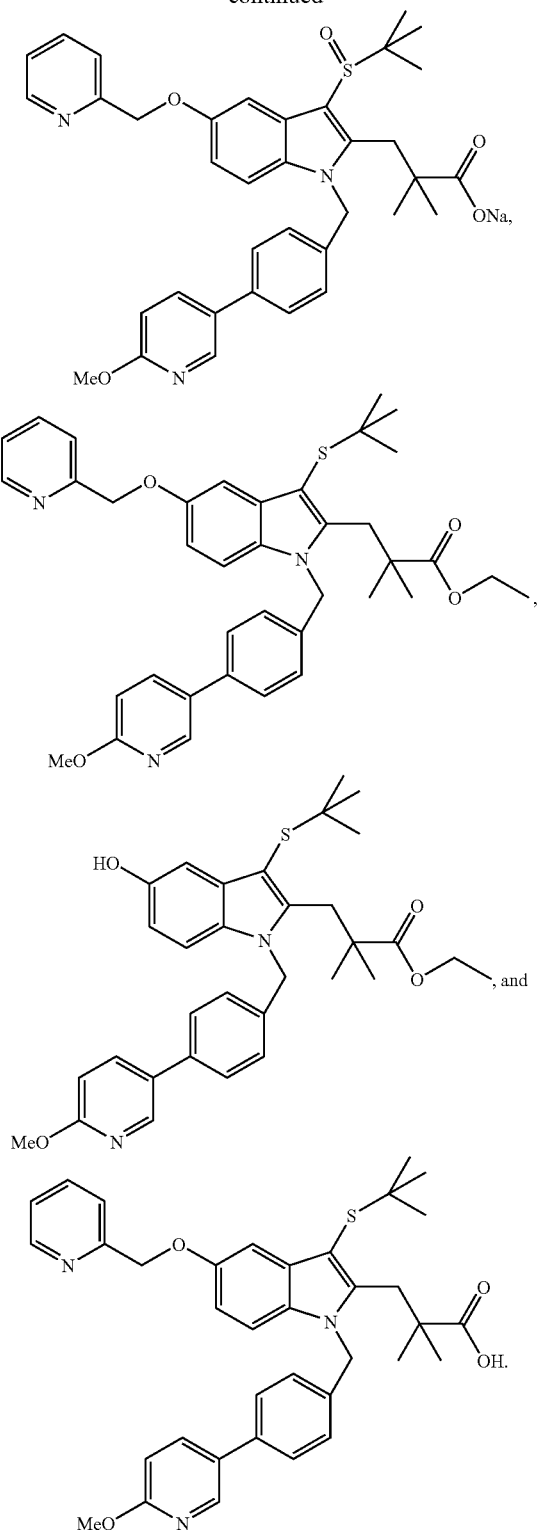

In one aspect, described is crystalline sodium 3-[(5-pyridin-2ylmethoxy)-3-(2-methyl-2-propylthio)-1-[4-(2-methoxypyridin-5-yl)benzyl]indol-2-yl]-2,2-dimethyl-propionate or pharmaceutically acceptable solvate thereof.

In one aspect, described is crystalline 3-[(5-pyridin-2yl-methoxy)-3-(2-methyl-2-propylthio)-1-[4-(2-methoxypyridin-5-yl)benzyl]indol-2-yl]-2,2-dimethyl-propionic acid or pharmaceutically acceptable solvate thereof.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this

BRIEF DESCRIPTION OF THE FIGURES

FIG. 8 presents the results of experiments conducted to evaluate the CYP induction of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid. 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid is not an inducer of CYP 3A4 and CYP 2C9.

DETAILED DESCRIPTION OF THE INVENTION

Figure 1:
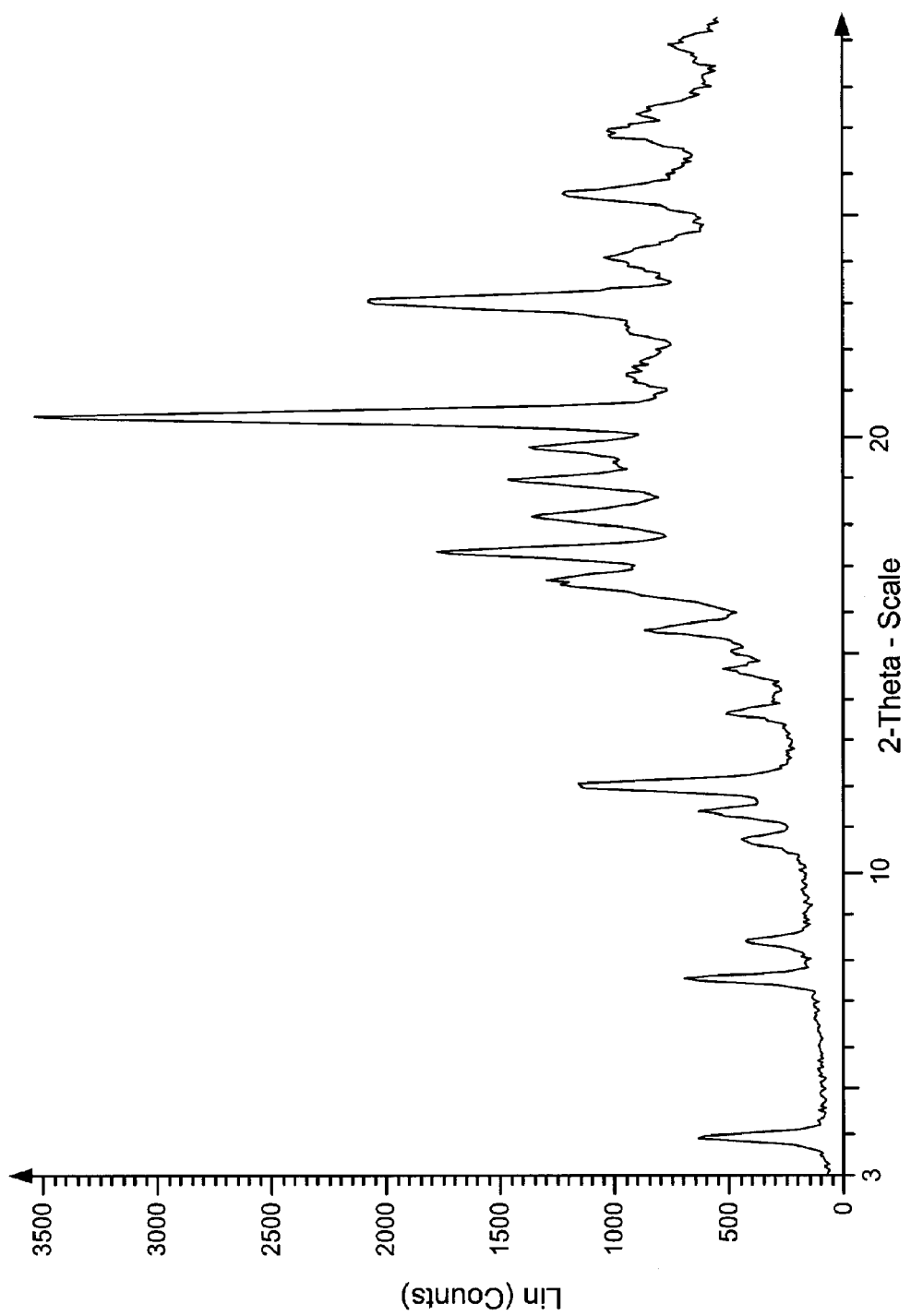
FIG. 1 presents XRPD of Form C of sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate.

Leukotrienes (LTs) are a class of pro-inflammatory lipid mediators derived from arachidonic acid that have been shown to play important roles in a number of biological processes. Arachidonic acid is converted to leukotriene $A_4$ ($LTA_4$) in a two-step process mediated by the enzyme 5-lipoxygenase (5-LO). The initial step is the oxygenation of arachidonic acid to form 5(S)-hydroperoxy-6,8,11,14(E,Z,Z,Z)-eicosatetraenoic acid (5-HPETE) followed by dehydration to produce the unstable epoxide $LTA_4$. $LTA_4$ is converted either to LTB$_4$ via LTA$_4$ hydrolase or to LTC$_4$ through conjugation with glutathione mediated by LTC$_4$ synthase. Amide bond cleavage converts LTC$_4$ to LTD$_4$ and then subsequently to LTE$_4$. The initial oxidation step is a process that requires the intimate involvement of both 5-LO and the membrane bound 5-lipoxygenase-activating protein (FLAP). Inhibition of either FLAP or 5-LO results in the inhibition of all leukotriene production. LTB$_4$ is the ligand for the G protein-coupled receptors (GPCRs) BLT$_1$ and BLT$_2$ and both receptors are involved in chemotaxis and cell stimulation in the inflammatory response. Bronchoconstriction, airway edema and hypersecretion of mucus are a result of the actions of the cysteinyl leukotrienes (cysLTs) LTC$_4$, LTD$_4$ and LTE$_4$. Both LTD$_4$ and LTE$_4$ are ligands for the cysLT$_1$ receptor. Antagonism of the cysLT$_1$ receptor or inhibition of 5-lipoxygenase have been shown to be effective methods for the treatment of asthma (Drazen, J. (1998) Clinical pharmacology of leukotriene receptor antagonists and 5-lipoxygenase inhibitors. *Am. J. Respire. Crit. Care Med.*, 157, S233-S237).

Leukotrienes are lipid mediators of inflammation that are involved in the pathogenesis of respiratory and cardiovascular diseases. Cellular activation by immune complexes and other inflammatory stimuli results in an increase of intracellular calcium and the translocation of cytosolic phospholipase A$_2$ (cPLA$_2$) and 5-lipoxygenase (5-LO) from the cytosol to the nuclear membrane. In the presence of the 5-lipoxygenase-activating protein (FLAP), arachidonic acid (AA) released from the nuclear membrane by cPLA$_2$ is delivered to 5-LO for conversion to 5-(S)-hydroperoxy-6,8,11,14-eicosatetraenoic acid (5-HpETE) and then leukotriene A$_4$ (LTA$_4$). Membrane interaction of 5-LO with FLAP is essential for leukotriene biosynthesis. FLAP is an integral membrane protein that belongs to the MAPEG (membrane-associated proteins in eicosanoid and glutathione metabolism) superfamily. In contrast to other MAPEGs, FLAP has not been shown to have enzymatic activity or to be functionally modulated by glutathione.

Leukotrienes are potent mediators of inflammation and bronchospasm. Leukotrienes are produced mainly by mast cells, eosinophils, monocytes/macrophages, and neutrophils in response to allergic or inflammatory stimuli. For cellular synthesis of leukotrienes, 5-lipoxygenase translocates from a nonmembrane compartment (cytosol or nucleosol) to membranes (nuclear or endoplasmic reticulum) and interacts with 5-lipoxygenase activating protein (FLAP). FLAP transfers arachidonic acid, released from membrane phospholipids by phospholipases, to 5-lipoxygenase. Then, a two step reaction occurs to convert arachidonic acid to LTA$_4$. LTA$_4$ can be exported from the cell for transcellular metabolism or converted to either LTB$_4$ or LTC$_4$. LTC$_4$ is exported from cells and converted to LTD$_4$ and then LTE$_4$ in blood. LTB$_4$ activates BLT$_1$ and BLT$_2$ receptors, and the cysteinyl leukotrienes activate cysLT$_I$ and cysLT$_2$ receptors (and possibly a cysLT$_3$ receptor).

While cysteinyl leukotriene-mediated human bronchoconstriction occurs by means of cysLT$_1$ receptor activation, both cysLT$_1$ and cysLT$_2$ receptors are present on cells involved in allergic inflammation, including mast cells, eosinophils, and monocytes.

A number of orally active drugs have been developed that affect the leukotriene pathway. Montelukast is a marketed leukotriene receptor antagonist, although others (pranlukast, zafirlukast) are also approved for treatment of asthma and allergic rhinitis. These drugs antagonize cysLT$_1$ receptors but not cysLT$_2$ or LTB$_4$ receptors. Clinical studies with these cysLT$_1$ receptor antagonists have demonstrated that cysteinyl leukotrienes are important mediators of allergen-induced lung volume decline (early and late phases) as well as chronic asthma. One 5-lipoxygenase inhibitor, zileuton, has exhibited clinical efficacy in chronic asthma although it was not effective in allergen-challenge studies.

Three FLAP inhibitors in clinical trials (MK-0591, MK-866, and BAYX-1005) have shown efficacy against allergen-induced early and late phases of lung-volume decline. Although none of these FLAP inhibitors is marketed, MK-0591 has also shown efficacy in chronic asthma studies.

MK-0591 is known as 3-[1-(4-chlorobenzyl)-3-(tert-butylthio)-5-(quinolin-2-ylmethoxy)indol-2-yl]-2,2-dimethyl propanoic acid. MK-866 is known as 3-[1-(4-chlorobenzyl)-3-(tert-butylthio)-5-(isopropyl)-indol-2-yl]-2,2-dimethyl propanoic acid. BAYX-1005 is known as (R)-2-[4-(quinolin-2-yl-methoxy)phenyl]-2-cyclopentyl acetic acid.

Inhaled medications, such as beta-agonists and corticosteroids, can be effective and minimize systemic exposure, patient compliance with such drug-delivery devices is less than optimal (Cochrane M G, et al., Inhaled corticosteroids for asthma therapy: Patient compliance, devices, and inhalation technique. *Chest.* 2000; 117:542-550). Among patients who used inhaled steroids, for example, growth may be retarded in children or cataracts induced in adults.

3-[5-(Pyridin-2-ylmethoxy)-3-(2-methyl-2-propylthio)-1-[4-(2-methoxypyridin-5-yl)benzyl]-indol-2-yl]-2,2-dimethyl-propionic acid is a potent FLAP inhibitor that blocks an early step in the leukotriene pathway, i.e., 5-lipoxygenase activation. 3-[5-(Pyridin-2-ylmethoxy)-3-(2-methyl-2-propylthio)-1-[4-(2-methoxypyridin-5-yl)benzyl]-indol-2-yl]-2,2-dimethyl-propionic acid is pharmacologically active in vitro and after oral administration and well tolerated in nonclinical studies. Furthermore, because it inhibits the formation of LTB$_4$ and the cysteinyl leukotrienes, 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid offers additional clinical benefits over leukotriene receptor antagonists such as montelukast.

The role of FLAP in the leukotriene synthesis pathway is significant because FLAP in concert with 5-lipoxygenase performs the first step in the pathway for the synthesis of leukotrienes. Therefore the leukotriene synthesis pathway provides a number of targets for compounds useful in the treatment of leukotriene-dependent or leukotriene mediated diseases or conditions, including, by way of example, vascular and inflammatory disorders, proliferative diseases, respiratory and non-cancerous disorders. Compounds that are inhibitors of proteins involved in leukotriene synthesis, such as FLAP, are useful in the treatment of leukotriene-dependent or leukotriene mediated diseases or conditions.

Described herein are compositions, pharmaceutical compositions, methods for treating, methods for formulating, methods for producing, methods for manufacturing, treatment strategies, pharmacokinetic strategies using 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, or pharmaceutically salts thereof, including pharmaceutically acceptable solvates thereof.

3-[5-(Pyridin-2-ylmethoxy)-3-(2-methyl-2-propylthio)-1-[4-(2-methoxypyridin-5-yl)benzyl]-indol-2-yl]-2,2-dimethyl-propionic acid has the following structure:

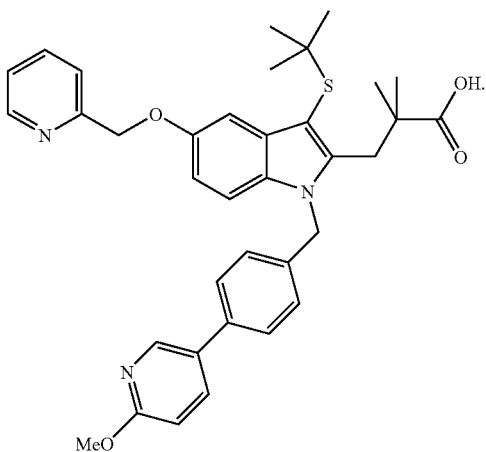 [SMILES: COc1ccc(-c2ccc(Cn3c(CC(C)(C)C(=O)O)c(SC(C)(C)C)c4cc(OCc5ccccn5)ccc43)cc2)cn1]

3-[5-(Pyridin-2-ylmethoxy)-3-(2-methyl-2-propylthio)-1-[4-(2-methoxypyridin-5-yl)benzyl]indol-2-yl]-2,2-dimethyl-propionic acid is also known as 3-[3-tert-butylsulfanyl-1-[4-(6-methoxy-pyridin-3-yl)-benzyl]-5-(pyridin-2-ylmethoxy)1H-indol-2-yl]-2,2-dimethyl propionic acid, and the two names are interchangeable. Other names may be known.

The sodium salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, also known as sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate and sodium 3-[3-tert-butylsulfanyl-1-[4-(6methoxy-pyridin-3-yl)-benzyl]-5-(pyridin-2-ylmethoxy) 1H-indol-2-yl]-2,2-dimethyl propionate, has the following structure:

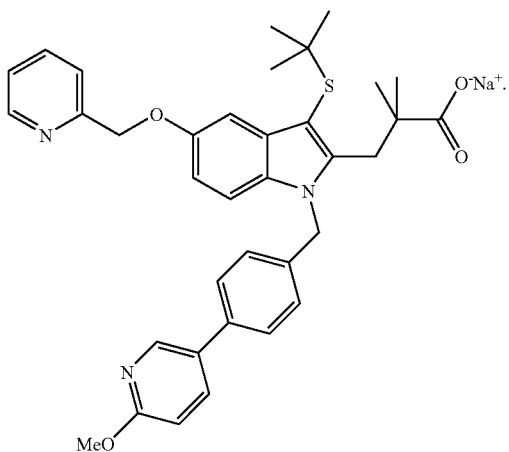

Other names for the sodium salt of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid may be known.

3-[5-(Pyridin-2-ylmethoxy)-3-(2-methyl-2-propylthio)-1-[4-(2-methoxypyridin-5-yl)benzyl]-indol-2-yl]-2,2-dimethyl-propionic acid contains two basic sites (pyridinyl groups) and one acidic site (carboxylic acid). A wide variety of salts are formed.

Salts of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid include:

A) salts formed when the acidic proton of the carboxylic acid of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid is replaced by a metal ion, such as for example, an alkali metal ion (e.g. lithium, sodium, potassium), an alkaline earth ion (e.g. magnesium, or calcium), or an aluminum ion, or is replaced by an ammonium cation ($NH_4^+$);

B) salts formed by reacting 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid with a pharmaceutically acceptable organic base, which includes alkylamines, such as ethanolamine, diethanolamine, triethanolamine, tromethamine, N-methylglucamine, dicyclohexylamine, tris(hydroxymethyl)methylamine, and salts with amino acids such as arginine, lysine, and the like;

C) salts formed by reacting 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid with a pharmaceutically acceptable acid, which provides acid addition salts. Pharmaceutically acceptable acids include hydrochloric acid, hydrobromic acid, sulfuric acid, nitric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

The term "pharmaceutically acceptable excipient," as used herein, refers to a material which does not abrogate the desired biological activity or desired properties of the compound, and is relatively nontoxic, i.e., the material is administered to an individual without causing undesirable biological effects or interacting in a deleterious manner with any of the components of the composition in which it is contained. Pharmaceutically acceptable excipient(s) are used in the manufacture of pharmaceutical compositions, formulations and medicaments.

"3-[5-(Pyridin-2-ylmethoxy)-3-(2-methyl-2-propylthio)-1-[4-(2-methoxypyridin-5-yl)benzyl]-indol-2-yl]-2,2-dimethyl-propionic acid drug substance" includes 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid, pharmaceutically acceptable salts, pharmaceutically acceptable solvates, and pharmaceutically acceptable hydrates thereof. The term includes the different forms, such as, amorphous phase, partially crystalline, and crystalline forms. In one aspect, "3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance" refers to the crystalline form of sodium 3-[5-

(pyridin-2-ylmethoxy)-3-(2-methyl-2-propylthio)-1-[4-(2-methoxypyridin-5-yl)benzyl]-indol-2-yl]-2,2-dimethyl-propionate or pharmaceutically solvate thereof. In one aspect, "3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance" refers to the crystalline form of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid or pharmaceutically solvate thereof.

"Sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate drug substance" includes sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate, and pharmaceutically acceptable solvates thereof. The term includes the different forms and phases, such as, amorphous phase and partially crystalline, and crystalline forms.

The term "pharmaceutically acceptable salt" refers to a salt that does not cause significant irritation to an organism to which it is administered and does not abrogate the biological activity and properties of the compound. In one aspect, the term "pharmaceutically acceptable salt" refers to a salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, which does not cause significant irritation to an organism to which it is administered and does not abrogate the biological activity and properties of the compound.

The term "pharmaceutical combination" as used herein, means a product that results from the mixing or combining of more than one active ingredient and includes both fixed and non-fixed combinations of the active ingredients. The term "fixed combination" means that the active ingredients, e.g. 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance, and a co-agent, are both administered to a patient simultaneously in the form of a single entity or dosage. The term "non-fixed combination" means that the active ingredients, e.g. 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of an active agent (or ingredient) with other inactive chemical components, such as carriers, stabilizers, diluents, dispersing agents, suspending agents, thickening agents, and/or excipients. The pharmaceutical composition facilitates administration of the compound to an organism. In one aspect, the active agent is 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance.

It should be understood that a reference to a pharmaceutically acceptable salt includes the solvent addition forms (solvates). Solvates contain either stoichiometric or non-stoichiometric amounts of a solvent, and are formed during the process of crystallization with pharmaceutically acceptable solvents such as water, ethanol, and the like. In one aspect, solvates are formed using, but not limited to, Class 3 solvent(s). Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005). In one aspect, a solvate is a hydrate. Hydrates are formed when the solvent is water, or alcoholates are formed when the solvent is alcohol. In one embodiment, solvates of 3-[5-(pyridin-2-ylmethoxy)-3-(2-methyl-2-propylthio)-1-[4-(2-methoxypyridin-5-yl)benzyl] indol-2-yl]-2,2-dimethyl-propionic acid, or solvates of pharmaceutically acceptable salts of 3-[5-(pyridin-2-ylmethoxy)-3-(2-methyl-2-propylthio)-1-[4-(2-methoxypyridin-5-yl) benzyl]-indol-2-yl]-2,2-dimethyl-propionic acid, are conveniently prepared or formed during the processes described herein. In one aspect, solvates are formed by adsorption of water from the atmosphere. Solvates include instances when the solvent molecule is a part of the crystal lattice or when it is adsorbed. In addition, 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid, or pharmaceutically acceptable salts thereof, exist in unsolvated form.

Further Forms and Phases

3-[5-(Pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts thereof, and pharmaceutically acceptable solvates thereof, are in various forms, including but not limited to, amorphous phase, partially crystalline forms, crystalline forms, milled forms, and nano-particulate forms. The crystalline forms are known as polymorphs. Polymorphs include the different crystal packing arrangements of the same elemental composition of a compound. This arrangement can significantly affect the physiochemical, formulation and processing parameters as well as the shelf life or stability of the substance and excipients. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature cause a single crystal form to dominate. In one aspect, a crystalline form of sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate is formed by crystallization from ethyl acetate. In one aspect, a crystalline form of sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate is formed by crystallization from a mixture of ethanol and ethyl acetate. In another aspect, a crystalline form of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid is formed by crystallization from ethanol.

Suitable Solvents

Good Manufacturing Practice (GMP) guidelines outline acceptable contamination levels of active therapeutic agents, such as, for example, the amount of residual solvent in the final product. Preferred solvents are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene.

Class 3 solvents, which possess low toxicity, include: acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran.

In some embodiments are compositions comprising 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable salts thereof that include an organic solvent(s). In some embodiments are compositions comprising 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable salts thereof that include a residual amount of an organic solvent(s). In some embodiments are compositions comprising 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable salts thereof that include a detectable amount of an organic solvent(s).

In one aspect, the organic solvent is selected from Class 3 solvents. In one aspect, the Class 3 solvents are as defined herein. In yet a further embodiment the Class 3 solvent is selected from ethyl acetate, isopropyl acetate, tert-butylmethylether, heptane, isopropanol, and ethanol. In other embodiments the organic solvent is selected from isopropanol, acetonitrile, ethanol, propylene glycol, and methylcellulose in water.

In some embodiments are compositions comprising a crystalline form of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable salts thereof comprising an organic solvent. In one aspect, the organic solvent in the composition is a residual amount. In another aspect, the organic solvent is a detectable amount. In one aspect, the crystalline form comprises crystalline 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid. In another aspect, the crystalline form comprises crystalline sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate.

In one aspect, the pharmaceutically acceptable salt of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid is selected from the sodium salt, potassium salt, lithium salt, calcium salt, ammonium salt, protonated dicyclohexylamine salt, protonated N-methyl-D-glucamine salt, protonated tris(hydroxymethyl)methylamine salt, protonated arginine salt, and protonated lysine salt.

In one aspect is a composition comprising sodium 3-[5-(pyridin-2-ylmethoxy)-3-(2-methyl-2-propylthio)-1-[4-(2-methoxypyridin-5-yl)benzyl]indol-2-yl]-2,2-dimethyl-propionate and an organic solvent. In another embodiment is a composition comprising sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate and a Class 3 solvent. In one embodiment, described is a composition comprising sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate and a Class 3 solvent selected from ethyl acetate, isopropyl acetate, tert-butylmethylether, heptane, isopropanol, and ethanol.

In yet a further embodiment, the Class 3 solvent is ethanol. In another embodiment, the Class 3 solvent is ethyl acetate.

In one aspect, a composition comprising 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid or pharmaceutically acceptable salts thereof includes a detectable amount of water. In another aspect, a composition comprising 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid or pharmaceutically acceptable salts thereof does not include a detectable amount of water.

Appropriate selection of the solvent(s) used for the synthesis of drug substance may enhance the yield, or determine characteristics such as crystal form, purity, and solubility. In one aspect, the solvent is a critical parameter in the synthetic process.

In one aspect, described are compositions comprising 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid or pharmaceutically acceptable salts thereof, wherein the composition comprises a detectable amount of one or more solvents. In one aspect, the test for residual solvents was performed via headspace or direct injection using a gas chromatograph equipped with a flame ionization detector (FID). In one aspect, the detectable amount of one or more solvents in the composition is less than about 1% based on gas chromatogram peak area. In one aspect the solvent is selected from 1,2-dimethoxyethane, acetonitrile, ethyl acetate, tetrahydrofuran, methanol, ethanol, heptane, and 2-propanol. In a further embodiment, the composition comprises a detectable amount of one or more solvents which is less than about 5000 ppm. In yet a further embodiment, are compositions comprising a detectable amount of one or more solvents that is less than about 3000 ppm, less than about 1000 ppm, less than about 500 ppm, or less than about 100 ppm.

Processes for the Preparation of a FLAP Inhibitor

Scheme 1 outlines the process for the preparation of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid and sodium salt thereof, in good yield and high purity.

Scheme 1: Synthesis of a FLAP Inhibitor:

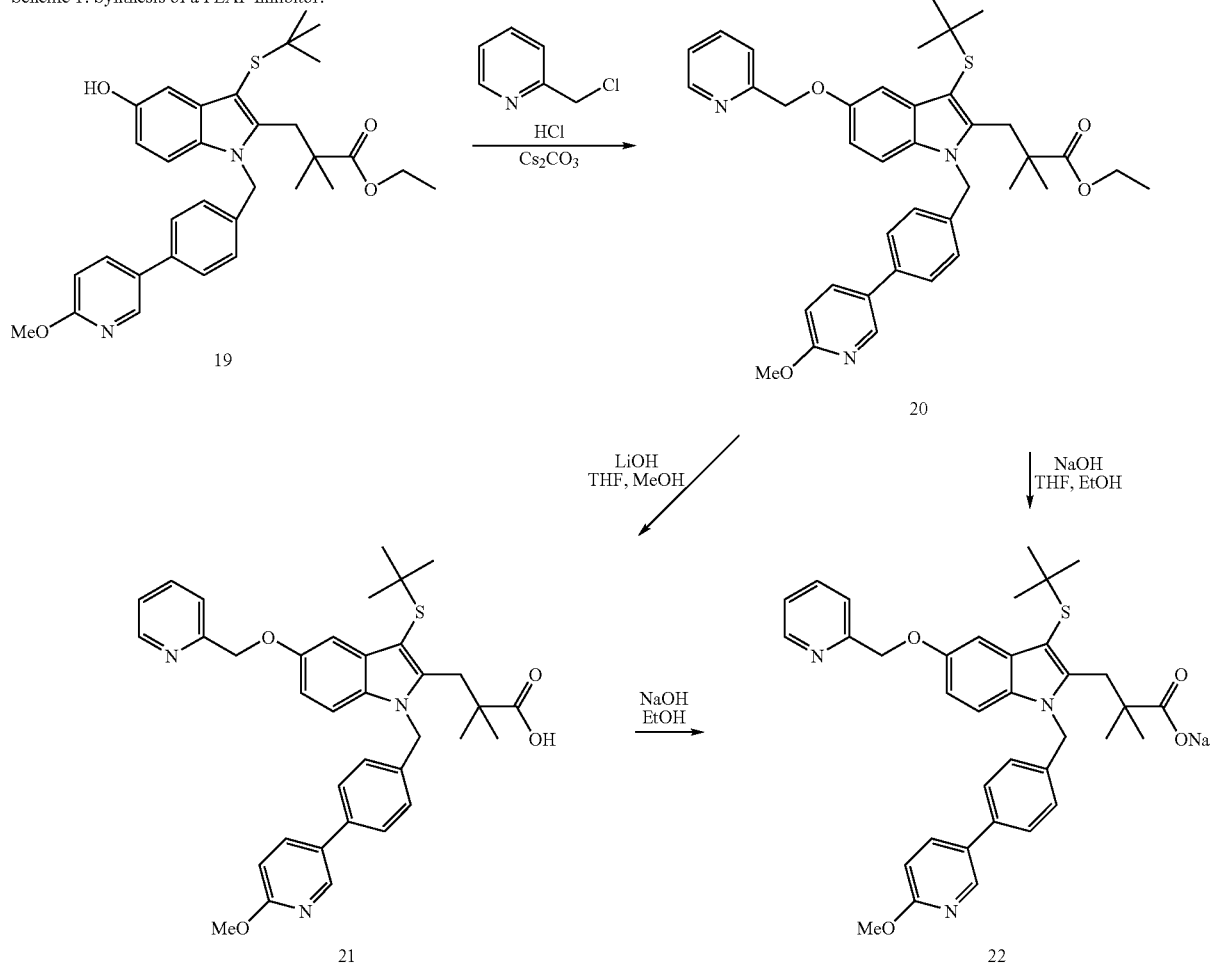

Reaction of compound 19 with 2-chloromethylpyridine hydrochloride in the presence of a base in a suitable solvent provides ester 20. In one aspect, the base is cesium carbonate. In another aspect, the base is potassium carbonate. In another aspect, the base is sodium carbonate. Other bases are known. In one aspect, the solvent is acetonitrile. In one aspect, the reaction is performed at an elevated temperature of about 70° C. to about 75° C. Hydrolysis of ester 20 with a base such as LiOH yields compound 21 after pH adjustment. Compound 21 is isolated by removal of solvent and dried under vacuum without the need for column chromatography. Treatment of compound 21 with sodium hydroxide yields sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate (compound 22) in good yield. In another aspect, saponification of compound 20 with NaOH yields sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate (compound 22) in good yield. In one aspect, amounts of heavy metals, such as palladium, are reduced or removed by dissolving compound 20 in a suitable solvent and treating with powdered activated carbon. In one aspect, the powdered activated carbon is Darco KB-G. In one aspect, the suitable solvent is ethanol. In one instance, compound 20 is treated with powdered activated carbon in a suitable solvent for at least 12 hours.

In one aspect, isolation of the compounds from the reactions identified in Scheme 1 does not require column chromatography.

In one aspect, amorphous 21 is obtained upon standard work of the reaction. In one instance, crystalline 21 is obtained by dissolving compound 21 in a suitable solvent and allowing compound 21 to crystallize. In one aspect, the suitable solvent is ethanol.

In one aspect, amorphous 22 is obtained upon standard work of the reaction. In one instance, crystalline 22 is obtained by dissolving compound 22 in a suitable solvent and allowing compound 22 to crystallize. In one aspect, the suitable solvent is ethyl acetate.

In one aspect are compositions comprising 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid or pharmaceutically acceptable salts thereof, including the pharmaceutically acceptable solvates thereof, and a detectable amount of a heavy metal which complies with the Good Manufacturing Practice. In one aspect, the heavy metal is palladium. In a further aspect, the detectable amount of palladium is less than about 20 ppm. In yet further embodiments, the detectable amount of palladium is less than about 10 ppm. In yet further embodiments, the detectable amount of palladium is less than about 5 ppm.

Compound 19 was prepared by utilizing a transition metal cross coupling reaction.

Scheme 2: Synthesis of Methoxy Pyridine Derivative

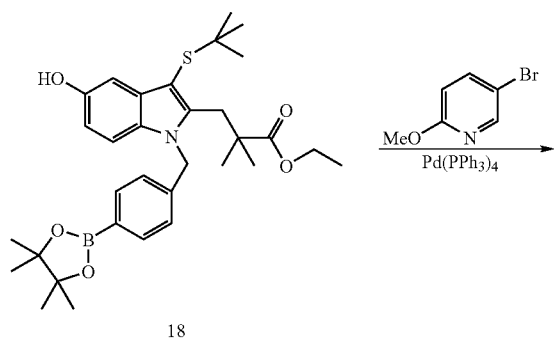

18

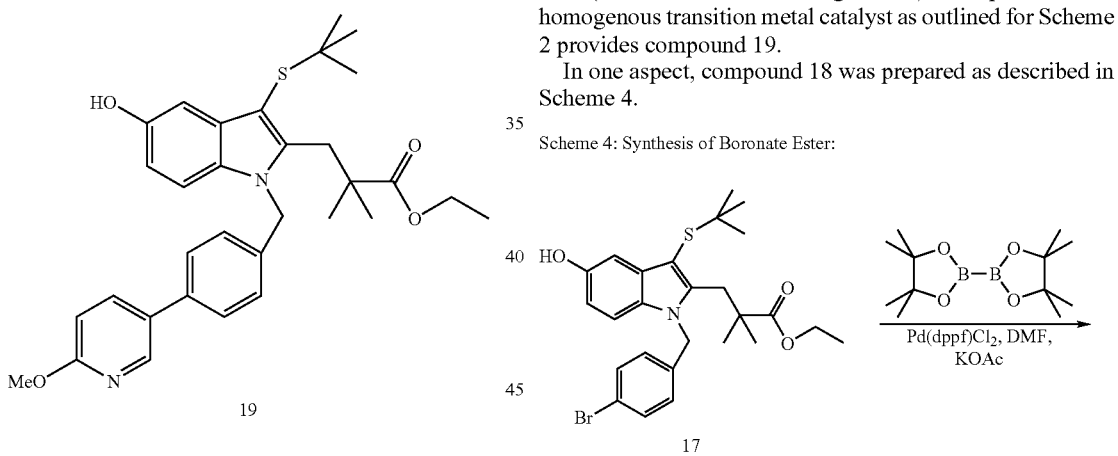

19

Coupling of phenyl boronate ester 18, or the boronic acid analog of 18, with a 5-halo-2-methoxy-pyridine compound, in the presence of a homogenous transition metal catalyst provides compound 19. In one instance, the homogenous transition metal catalyst is a homogeneous palladium catalyst. Typically, coupling reactions employing homogeneous palladium catalyst results in compounds containing varying amounts of the heavy metal. In one aspect, the palladium impurities are reduced or removed by dissolving compound 19 is a suitable solvent and adding activated carbon, followed by filtration of the resulting mixture over Celite. In another aspect, any remaining palladium in a sample of compound 19 was further reduced following the use of compound 19 in the reactions described in Scheme 1 and the purification of compound 20 as described above.

In another aspect, compound 19 is prepared by the reaction scheme outlined in Scheme 3.

Scheme 3: Alternative Synthesis of Methoxy Pyridine Derivative

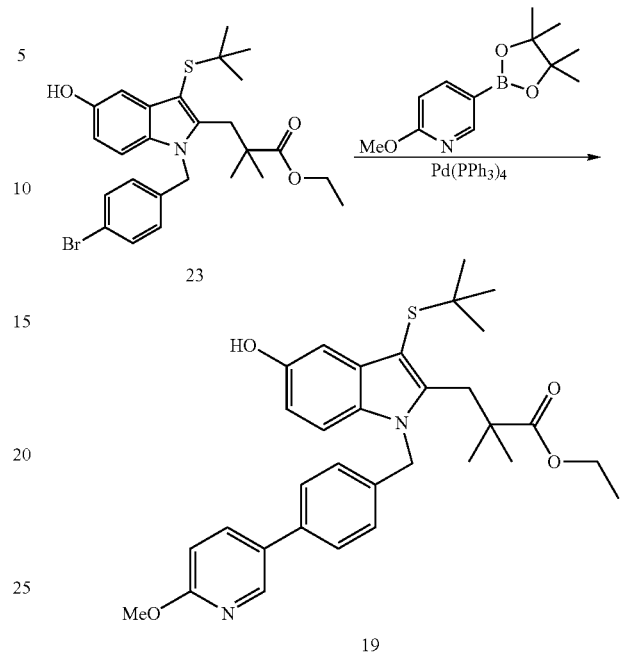

Coupling of benzyl halide 23 with a pyridinyl boronate ester (or the boronic acid analog thereof) in the presence of a homogenous transition metal catalyst as outlined for Scheme 2 provides compound 19.

In one aspect, compound 18 was prepared as described in Scheme 4.

Scheme 4: Synthesis of Boronate Ester:

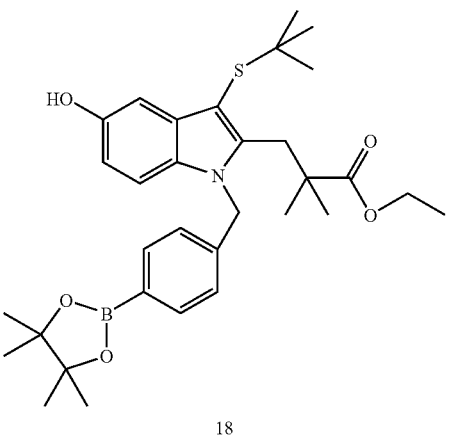

Phenyl boronate ester 18 is prepared by treating benzyl halide 17 with a borylation reagent in the presence of a heavy metal catalyst in a suitable solvent. In one embodiment, the heavy metal catalyst is a transition metal catalyst. In yet a further embodiment, the transition metal catalyst is a palladium metal catalyst. In another embodiment, the palladium catalyst is bis(diphenylphosphinoferrocene)palladium dichloride. In one aspect, the borylation reagent is selected from among pinacolborane, catecholborane, bis(neopentyl glycolato)diboron, bis(pinacolato)diboron, bis(hexylene glycolato)diboron, and bis(catecholato)diboron. In a further embodiment, the borylation reagent is bis(pinacolato)diboron. In one aspect, the reaction shown in Scheme 4 is performed at a temperature of about 70° C. to about 85° C. In other embodiments, the reaction shown in Scheme 4 is performed at a temperature of about 75 to about 85° C. under nitrogen. In a further embodiment, the reaction shown in Scheme 4 is agitated for a period of about 1-3 hours at an elevated temperature of about 80 to about 85° C.

In one instance, benzyl halide 17 was prepared as outlined in Scheme 5.

Scheme 5: Synthesis of Benzyl halide 17

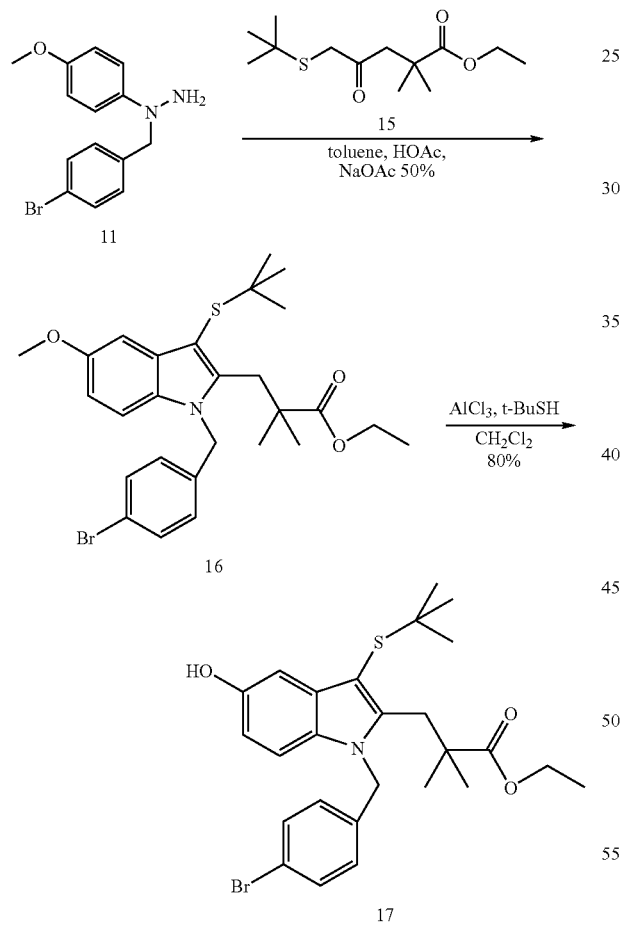

In one aspect, hydrazine 11 is prepared by reacting 4-methoxyphenyl hydrazine hydrochloride with 4-bromo-benzylbromide in the presence of a base and a suitable solvent. In one aspect, the suitable solvent is $Et_3N$. Other bases suitable for this alkylation reaction are contemplated. In one aspect, the bromine atom of compound 11 is replaced with other suitable atoms or groups, including but not limited to, —Cl, —I, —OSO$_2$CF$_3$, —OSO$_2$CH$_3$, and —OSO$_2$(4-methylphenyl).

Ketone 15 is formed through a series of reactions beginning with the alkylation of ethyl isobutyrate with 2,3-dichloropropene to give 4-chloro-2,2-dimethyl-pent-4-enoic acid ethyl ester. In one aspect, a strong non-nucleophilic base is used to deprotonate ethyl isobutyrate before it reacts with 2,3-dichloropropene. In one aspect, the strong non-nucleophilic base is selected from lithium diisopropylamide, sodium bis(trimethylsilyl)amide, potassium bis(trimethylsilyl)amide, sodium tert-butoxide, and lithium tetramethylpiperidine. 4-Chloro-2,2-dimethyl-pent-4-enoic acid ethyl ester is reacted with bromine to give a brominated ketone, which is then reacted with 2-methyl-2-propanethiol in the presence of a base to give ketone 15.

Hydrazine 11 is reacted with ketone 15 in a suitable solvent to form indole derivative 16 using Fischer-Indole reaction conditions. In one aspect, the suitable solvent is toluene. Indole derivative 16 is carried forward after a filtration wash using Celite. Demethylation of indole derivative 16 to provide hydroxy compound 17 is achieved by the use of a Lewis acid in a suitable solvent. In one aspect, the Lewis Acid is $AlCl_3$. In one embodiment, demethylation of indole derivative 16 comprises reacting indole derivative 16 with $AlCl_3$ in the presence of tert-butyl mercaptan. In other embodiments the Lewis acid is selected from Fe (III) chloride, boron trifluoride, niobium pentachloride, and lanthanide triflates, such as by way of example only, ytterbium (III) triflate. In one aspect, the suitable solvent is $CH_2Cl_2$. In some embodiments, Lewis acid mediated demethylations described above are performed at temperatures of about −5° C. to about 0° C. In one aspect, after acidification and extraction techniques, compound 17 is obtained without the need of purification using column chromatography.

In one embodiment is a processes for the preparation of a compound of Formula (I):

Formula (I)

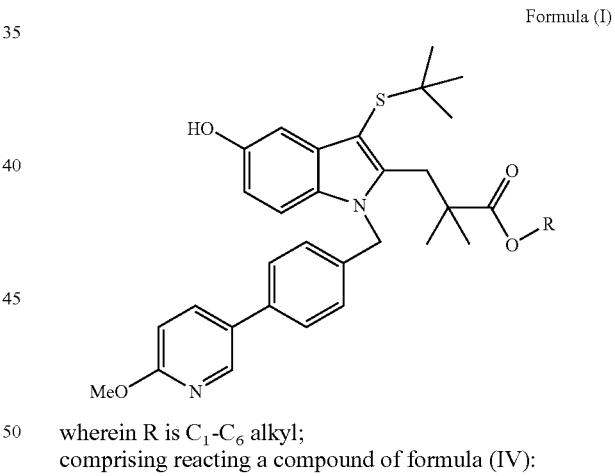

wherein R is $C_1$-$C_6$ alkyl;
comprising reacting a compound of formula (IV):

Formula (IV)

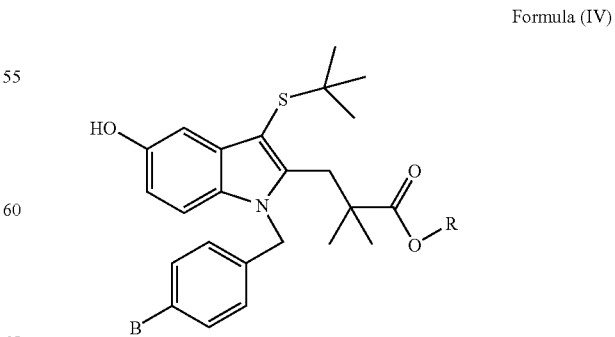

wherein R is $C_1$-$C_6$ alkyl; and B is a boronic acid or boronate ester;

with a compound of Formula (V):

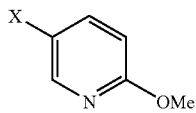

Formula (V)

wherein X is a leaving group,
in the presence of a first coupling catalyst and base in a suitable solvent.

In another embodiment is a processes for the preparation of a compound of Formula (I):

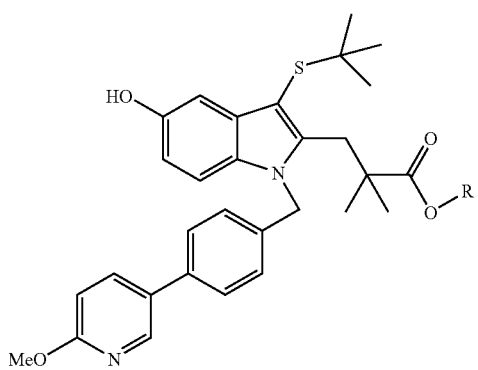

Formula (I)

wherein R is $C_1$-$C_6$ alkyl;
comprising reacting a compound of formula (X):

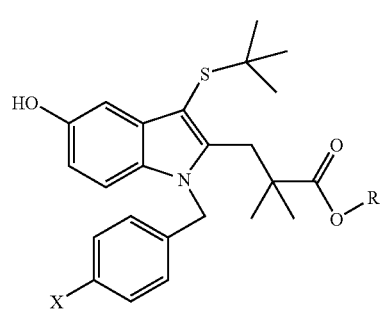

Formula (X)

wherein R is $C_1$-$C_6$ alkyl; and X is a leaving group;
with a compound of Formula (XI):

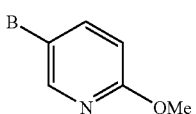

Formula (XI)

wherein B is a boronic acid or boronate ester,
in the presence of a first coupling catalyst and base in a suitable solvent.

In one aspect, a by-product of the process for the synthesis of the compound of Formula (I) is triphenylphosphine oxide. In one aspect, the first coupling catalyst is a triphenylphosphine containing catalyst. In one instance, the first coupling catalyst is a transition metal catalyst. In one aspect, the first coupling catalyst is a palladium metal catalyst containing triphenylphosphine.

Bases typically used in palladium mediated reactions include but are not limited to $Cs_2CO_3$, triethylamine, diisopropylethylamine, 1,2,2,6,6-pentamethylpiperidine, tributylamine, $Na_2CO_3$, $K_2CO_3$, NaOAc, and $K_3PO_4$.

In one aspect, presented herein is a process for the preparation of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, pharmaceutically acceptable solvates, crystalline forms, amorphous phases, partially crystalline forms thereof, comprising the steps of:

(i) reacting a compound of Formula (I):

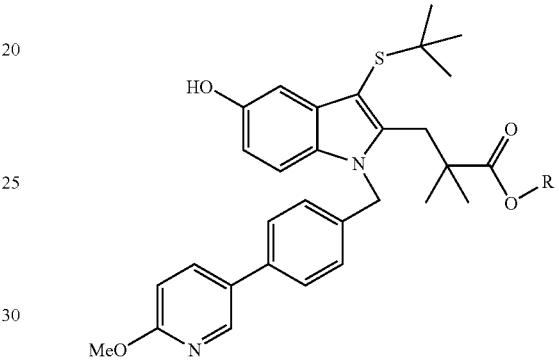

Formula (I)

wherein R is $C_1$-$C_6$ alkyl;
with a compound of Formula (II):

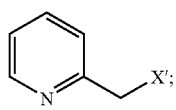

Formula (II)

wherein X' is a leaving group;
in a suitable solvent and in the presence of a base to form a compound of Formula (III)

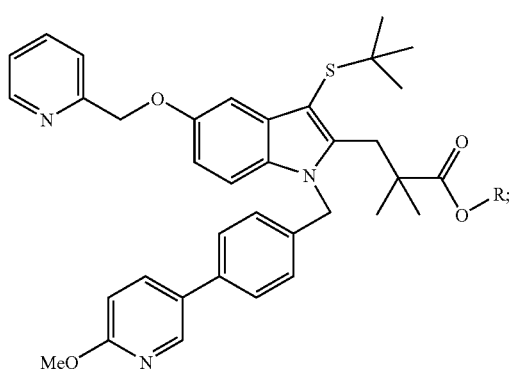

Formula (III)

(ii) forming a salt of the product of step (i).

In one aspect, step (ii) comprises forming a sodium salt of the product of step (i). In one aspect, step (ii) comprises:

a) treatment of the product of step (i) with LiOH, KOH, or Ca(OH)$_2$, followed by a pH adjustment to form the carboxylic acid, followed by NaOH; or b) treatment of the product of step (i) with NaOH.

In one aspect, step (ii) comprises treatment of the product of step (i) with LiOH, followed by a pH adjustment to form the carboxylic acid, followed by NaOH. In one aspect, step (ii) comprises treatment of the product of step (i) with NaOH.

In one aspect, step (ii) comprises:

hydrolyzing the ester of the compound of Formula (III) to form

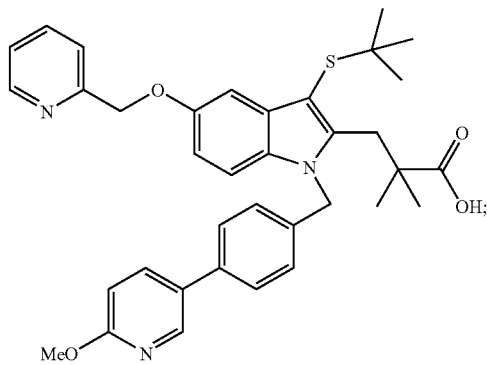 [SMILES: COc1ccc(-c2ccc(Cn3c(CC(C)(C)C(=O)O)c(SC(C)(C)C)c4cc(OCc5ccccn5)ccc43)cc2)cn1]

followed by forming a salt of

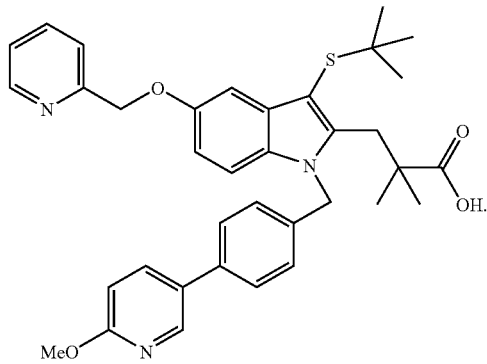 [SMILES: COc1ccc(-c2ccc(Cn3c(CC(C)(C)C(=O)O)c(SC(C)(C)C)c4cc(OCc5ccccn5)ccc43)cc2)cn1]

In one aspect, step (ii) comprises:

treatment of the product of step (i) with LiOH, KOH, or Ca(OH)$_2$, followed by a pH adjustment to form

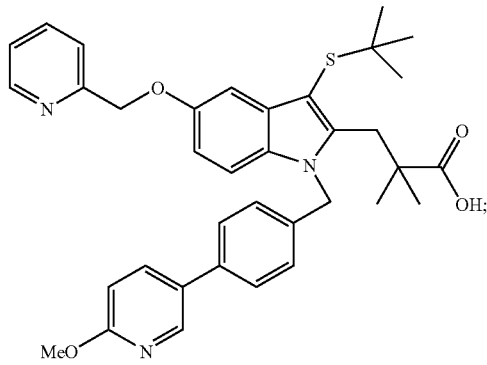 [SMILES: COc1ccc(-c2ccc(Cn3c(CC(C)(C)C(=O)O)c(SC(C)(C)C)c4cc(OCc5ccccn5)ccc43)cc2)cn1]

followed by forming a salt of

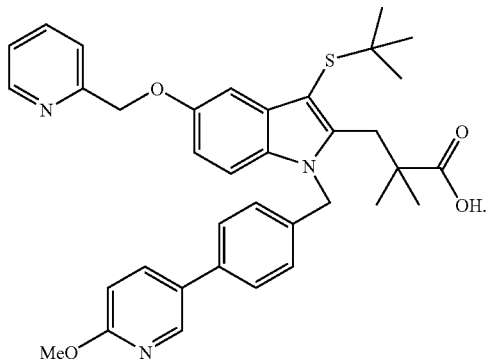 [SMILES: COc1ccc(-c2ccc(Cn3c(CC(C)(C)C(=O)O)c(SC(C)(C)C)c4cc(OCc5ccccn5)ccc43)cc2)cn1]

In some embodiments, R is methyl or ethyl. In other embodiments, R is methyl. In yet other embodiments, R is ethyl.

In one aspect, salts of

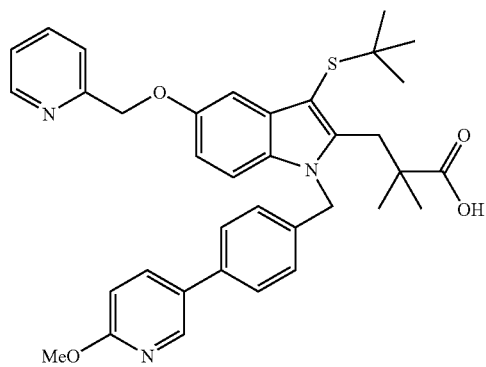 [SMILES: COc1ccc(-c2ccc(Cn3c(CC(C)(C)C(=O)O)c(SC(C)(C)C)c4cc(OCc5ccccn5)ccc43)cc2)cn1]

are formed by treatment with a sodium base, potassium base, lithium base, calcium base, ammonia, dicyclohexylamine, N-methyl-D-glucamine, tris(hydroxymethyl)methylamine, arginine, or lysine. In one aspect, a sodium base is used.

In one aspect, the process for preparing 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid includes a solvent. In one aspect, the process for preparing sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate includes a solvent. In some embodiments, the solvent is an organic solvent. In other embodiments, the organic solvent is a Class 3 solvent. In other embodiments, the solvent is selected from among ethyl acetate, ethanol, acetonitrile and tetrahydrofuran. In some other embodiments, the solvent is ethyl acetate. In other embodiments, the solvent is acetonitrile.

The process for preparing 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid includes reacting a compound of Formula (I) with a compound of Formula (II) in the presence of a base. In some embodiments, the base is a cesium base. In one aspect, the cesium base is Cs$_2$CO$_3$.

In one aspect, X' is selected from the group of —Cl, —Br, —I, —OSO$_2$CF$_3$, —OSO$_2$(4-methylphenyl), and —OSO$_2$CH$_3$. In another aspect, X' is a halide. In yet a further aspect, X' is —Cl.

In one embodiment the reaction of step (i) further comprises heating to a temperature of about 50 to about 90° C. In other embodiments, the reaction of step (i) is heated to a temperature of about 60 to about 80° C. In further embodiments, the reaction of step (i) is heated to a temperature of about 70 to about 75° C. Heating methods include the use of heating equipment such as, for example only, a heating plate, heating mantle, an oil bath or a water bath.

In one aspect, the product from step (i) is isolated. In another aspect, the product from step (i) is not isolated. In one aspect, the compound of Formula (I) is prepared using a palladium coupling reaction and contains residual palladium. In one aspect, isolating the product from step (i) comprises a means for reducing residual palladium. In one aspect, activated carbon is used to reduce residual palladium. Activated carbon, a carbon material generally derived from charcoal, has an exceptionally high surface area and good adsorptive capacity. Powdered activated carbon is typically composed of ground carbon particles with average particle sizes ranging from about 5 to about 500 microns. In a further embodiment, the activated carbon is powdered activated carbon. In yet a further embodiment, the powdered activated carbon has an average particle size from about 5 to about 100 microns. In another embodiment, the powdered activated carbon has a particle size from about 5 to about 50 microns. In yet a further embodiment, the powdered activated carbon is DARCO® KB-G, DARCO® KB-WJ.

"Means for reducing residual palladium" (or a similarly worded phrase) refers to a means used for reducing the amount of palladium in samples comprising active pharmaceutical ingredients in order to meet palladium specification guidelines. ("Guideline on the Specification Limits for Residues of Metal Catalysts" European Medicines Agency *Preauthorisation Evaluation of Medicines for Human Use*, London, January 2007, Doc. Ref. CPMP/SWP/QWP/4446/00 corr.). In one aspect, purifying means for reducing amount palladium include, but are not limited to, solid trimercaptotriazine (TMT), polystyrene-bound TMT, mercapto-porous polystyrene-bound TMT, polystyrene-bound ethylenediamine, activated carbon, glass bead sponges, Smopex™, silica bound scavengers, thiol-derivatized silica gel, N-acetylcysteine, n-Bu₃P, crystallization, extraction, 1-cysteine, n-Bu₃P/lactic acid. Garrett et al., *Adv. Synth. Catal.* 2004, 346, 889-900. In one aspect, activated carbon includes but is not limited to DARCO® KB-G, DARCO® KB-WJ. In one aspect silica bound scavengers include but are not limited to

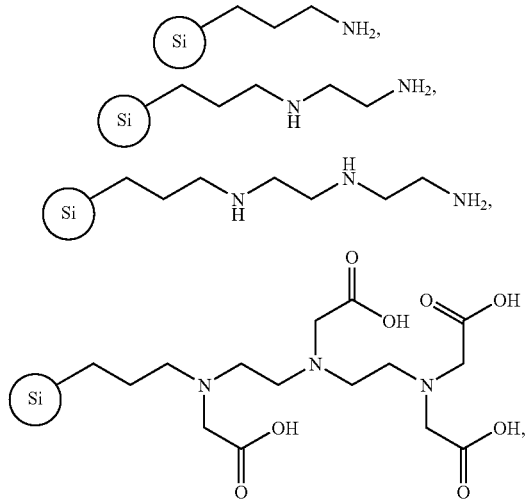

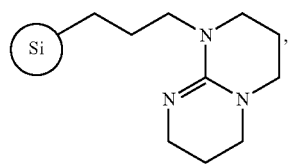

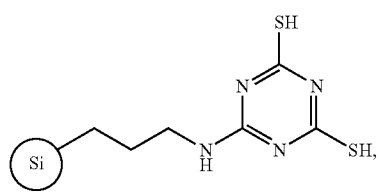

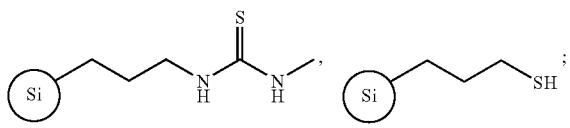

denotes silica gel.

In one aspect, compositions comprising sodium 3-[5-(pyridin-2-ylmethoxy)-3-(2-methyl-2-propylthio)-1-[4-(2-methoxypyridin-5-yl)benzyl]indol-2-yl]-2,2-dimethyl-propionate comprise a detectable amount of one or more compounds selected from:

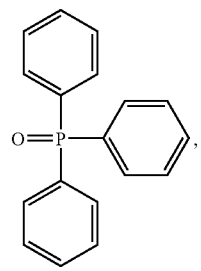

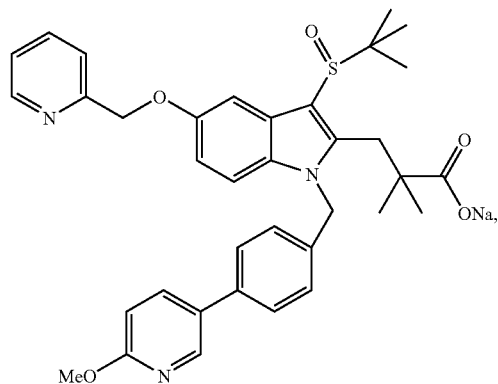

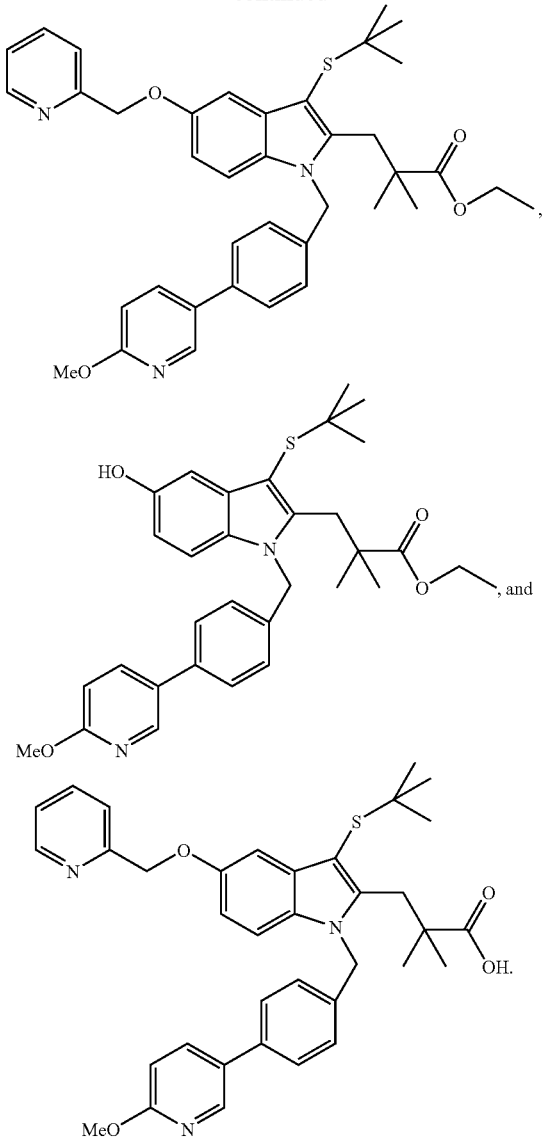

In one aspect, sodium 3-[5-(pyridin-2-ylmethoxy)-3-(2-methyl-2-propylthio)-1-[4-(2-methoxypyridin-5-yl)benzyl]indol-2-yl]-2,2-dimethyl-propionate has a purity greater than about 96%, about 97%, about 98% or 99%. In one aspect, the purity is measured by high performance liquid chromatography. In another aspect, the purity is measured by other analytical methods.

Described herein are processes for the preparation of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid, pharmaceutically acceptable salts, pharmaceutically acceptable solvates, crystalline forms, amorphous phases thereof, that avoid the use of toxic solvents and minimizes the contamination of the final product(s) with toxic solvents, by-products and/or reagents. In one aspect, described herein are processes that avoid the need for time consuming and expensive purification methods, such as column chromatography.

Processes described herein provide a crystalline form of sodium 3-[5-(pyridin-2-ylmethoxy)-3-(2-methyl-2-propylthio)-1-[4-(2-methoxypyridin-5-yl)benzyl]indol-2-yl]-2,2-dimethyl-propionate that has good solubility and good oral bioavailability.

Processes described herein provide a crystalline form of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid Described herein are processes for the preparation of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid, including but not limited to pharmaceutically acceptable solvates, pharmaceutically acceptable salts, crystalline forms, amorphous phases, on an industrial scale (such as multi-kilogram scale).

A crystalline form of sodium 3-[5-(pyridin-2-ylmethoxy)-3-(2-methyl-2-propylthio)-1-[4-(2-methoxypyridin-5-yl)benzyl]indol-2-yl]-2,2-dimethyl-propionate that has good solubility and oral bioavailability is also provided.

The processes disclosed herein are particularly applicable to large scale chemical production of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, pharmaceutically acceptable solvates, crystalline forms, amorphous phases.

Provided herein are compositions comprising a crystalline form of sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate, including pharmaceutically acceptable solvates thereof.

In another embodiment, the crystalline form of sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate is solvated with a Class 3 solvent selected from ethyl acetate, isopropyl acetate, tert-butylmethylether, heptane, isopropanol, and ethanol.

In one embodiment, the crystalline form of sodium 3-[5-(pyridin-2-ylmethoxy)-3-(2-methyl-2-propylthio)-1-[4-(2-methoxypyridin-5-yl)benzyl]indol-2-yl]-2,2-dimethyl-propionate is solvated with ethanol.

In a further embodiment, the crystalline form of sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate is in a desolvated form.

In yet a further embodiment, the crystalline form of sodium 3-[5-(pyridin-2-ylmethoxy)-3-(2-methyl-2-propylthio)-1-[4-(2-methoxypyridin-5-yl)benzyl]indol-2-yl]-2,2-dimethyl-propionate has an X-ray diffraction pattern with characteristic deg 2Θ values of 12.0, 17.4, 18.2, 19.0, 20.5 and 23.2.

In other embodiments, the crystalline form of sodium 3-[5-(pyridin-2-ylmethoxy)-3-(2-methyl-2-propylthio)-1-[4-(2-methoxypyridin-5-yl)benzyl]indol-2-yl]-2,2-dimethyl-propionate has an X-ray diffraction pattern with characteristic deg 2Θ values of 7.2, 9.1, 18.2, 20.9, and 22.3.

In yet another embodiment, the crystalline form of sodium 3-[5-(pyridin-2-ylmethoxy)-3-(2-methyl-2-propylthio)-1-[4-(2-methoxypyridin-5-yl)benzyl]indol-2-yl]-2,2-dimethyl-propionate has substantially the same X-ray diffraction pattern as shown in FIG. 1.

Figure 2:
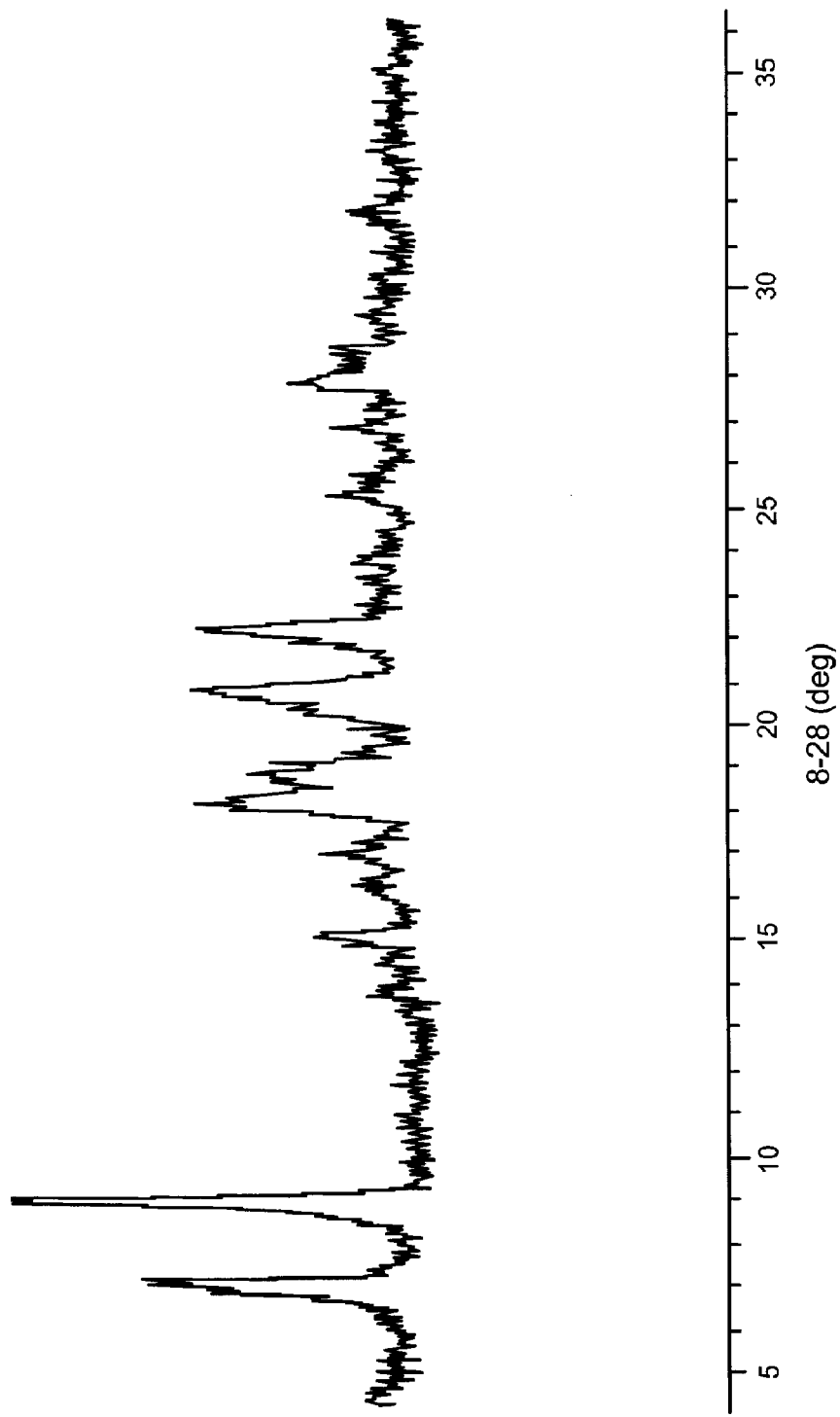
FIG. 2 presents XRPD of Form B of sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate.

In a further embodiment, the crystalline form of sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate has substantially the same X-ray diffraction pattern as shown in FIG. 2.

In one aspect, presented herein are is a crystalline form of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid.

In another aspect, presented herein is an amorphous phase of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid.

In a further embodiment is a crystalline form of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, wherein the crystalline form is desolvated. In yet a further embodiment, the crystalline form of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid is solvated.

In one aspect, sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate is soluble in an organic solvent selected from isopropanol, acetonitrile, ethanol, propylene glycol, methanol, and methylcellulose.

In another embodiment, sodium 3-[5-(pyridin-2-ylmethoxy)-3-(2-methyl-2-propylthio)-1-[4-(2-methoxypyridin-5-yl)benzyl]indol-2-yl]-2,2-dimethyl-propionate is soluble in water at a pH of between about 6 and about 10 at a temperature of about 25° C. greater than about 50 μg/mL.

In another embodiment, the solubility of sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate at a pH of about 9 and at a temperature of about 25° C. is greater than about 9 mg/mL.

In a further embodiment is a composition comprising sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate wherein the solubility of the sodium salt in water at a pH of about 0.5 at about 25° C. is greater than about 10 mg/mL.

In a further embodiment is a composition comprising sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate wherein the solubility of the sodium salt in water at a pH of about 8 at about 25° C. is about 6 μg/mL.

Certain Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, organic synthesis, biochemistry, recombinant DNA techniques and pharmacology, within the skill of the art are employed. In this application, the use of "or" means "and/or" unless stated otherwise. Furthermore, use of the term "including" as well as other forms, such as "include", "includes," and "included," is not limiting.

An "alkyl" group refers to an aliphatic hydrocarbon group. The alkyl group, whether saturated or unsaturated, is branched, straight chain, or cyclic. In one aspect, an "alkyl" is a "$C_1$-$C_6$ alkyl" (whenever it appears herein, a numerical range such as "1 to 6" refers to each integer in the given range; e.g., "1 to 6 carbon atoms" means that the alkyl group includes group with 1 carbon atom, 2 carbon atoms, 3 carbon atoms, etc., up to and including 6 carbon atoms, although the present definition also covers the occurrence of the term "alkyl" where no numerical range is designated). By way of example only, "$C_1$-$C_6$ alkyl" indicates that there are one to six carbon atoms in the alkyl chain, i.e., the alkyl is selected from, but are in no way limited to, methyl, ethyl, propyl, isopropyl, butyl, isobutyl, tertiary butyl, sec-butyl, pentyl, neopentyl, hexyl, ethenyl, propenyl, butenyl, cyclopropyl, cyclobutyl, cyclopentyl, cyclohexyl, and the like. In one aspect, the alkyl is selected from methyl, ethyl, propyl, isopropyl, butyl, isobutyl, tertiary butyl, sec-butyl, pentyl, neopentyl, and hexyl. In another aspect, the alkyl is selected from methyl and ethyl.

"Detectable amount" refers to an amount that is measurable using standard analytic methods (e.g. ion chromatography, mass spectrometry, NMR, HPLC, gas chromatography, elemental analysis, IR spectroscopy, inductively coupled plasma atomic emission spectrometry, USP<231> Method II, etc).

The term "acceptable" with respect to a formulation, composition or ingredient, as used herein, means having no persistent detrimental effect on the general health of the subject being treated.

The term "respiratory disease," as used herein, refers to diseases affecting the organs that are involved in breathing, such as the nose, throat, larynx, trachea, bronchi, and lungs. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "asthma" as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate cause.

The term "cardiovascular disease," as used herein refers to diseases affecting the heart or blood vessels or both, including but not limited to: arrhythmia; atherosclerosis and its sequelae; angina; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue.

The terms "effective amount" or "therapeutically effective amount," as used herein, refer to a sufficient amount of an agent being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. In one embodiment, an appropriate "effective" amount in any individual case is determined using techniques, such as a dose escalation study.

The terms "co-administration" or the like, as used herein, are meant to encompass administration of the selected therapeutic agents to a single patient, and are intended to include treatment regimens in which the agents are administered by the same or different route of administration or at the same or different time.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "fibrosis" or "fibrosing disorder," as used herein, refers to conditions that follow acute or chronic inflammation and are associated with the abnormal accumulation of cells and/or collagen and include but are not limited to fibrosis of individual organs or tissues such as the heart, kidney, joints, lung, or skin, and includes such disorders as idiopathic pulmonary fibrosis and cryptogenic fibrosing alveolitis.

The term "leukotriene-driven mediators," as used herein, refers to molecules able to be produced in a patient that results from excessive production of leukotriene stimulation of cells, such as, by way of example only, $LTB_4$, $LTC_4$, $LTE_4$, cysteinyl leukotrienes, monocyte inflammatory protein (MIP-1α), interleukin-8 (IL-8), interleukin-4 (IL-4), interleukin-13 (IL-13), monocyte chemoattractant protein (MCP-1), soluble intracellular adhesion molecule (sICAM; soluble ICAM), myeloperoxidase (MPO), eosinophil peroxidase (EPO), and general inflammation molecules such as interleukin-6 (I1-6), C-reactive protein (CRP), and serum amyloid A protein (SAA).

The term "leukotriene-related mediators," as used herein, refers to molecules able to be produced in a patient that result from excessive production of leukotriene stimulation of cells, such as, by way of example only, $LTB_4$, $LTC_4$, $LTE_4$, cysteinyl leukotrienes, monocyte inflammatory protein (MIP-1α), interleukin-8 (IL-8), interleukin-4 (IL-4), interleukin-13 (IL-13), monocyte chemoattractant protein (MCP-1), soluble intracellular adhesion molecule (sICAM; soluble ICAM), myeloperoxidase (MPO), eosinophil peroxidase (EPO), and general inflammation molecules such as interleukin-6 (I1-6), C-reactive protein (CRP), and serum amyloid A protein (SAA).

The term "leukotriene-dependent", as used herein, refers to conditions or disorders that would not occur, or would not occur to the same extent, in the absence of one or more leukotrienes.

The term "leukotriene-mediated", as used herein, refers to conditions or disorders that occur in the absence of leukotrienes but also occur in the presence of one or more leukotrienes.

The term "leukotriene-responsive patient," as used herein, refers to a patient who has been identified by either genotyping of FLAP haplotypes, or genotyping of one or more other genes in the leukotriene pathway and/or, by phenotyping of patients either by previous positive clinical response to another leukotriene modulator, including, by way of example only, zileuton (Zyflo™), montelukast (Singulair™), pranlukast (Onon™), zafirlukast (Accolate™), and/or by their profile of leukotriene-driven mediators that indicate excessive leukotriene stimulation of inflammatory cells, as likely to respond favorably to leukotriene modulator therapy. In one aspect, a leukotriene-responsive patient shows a positive clinical response to 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance.

"MAPEG" refers to "membrane associated proteins involved in eicosanoid and glutathione metabolism" and includes the following human proteins: 5-lipoxygenase activating protein (FLAP), leukotriene $C_4$ synthase ($LTC_4$ synthase), which are involved in leukotriene biosynthesis; microsomal glutathione 5-transferase 1 (MGST1), MGST2, and MGST3, which are all glutathione transferases as well as glutathione dependent peroxidases; and prostaglandin E synthase (PGES), also referred to as MGST1-like 1 (MGST1-L1). PGES catalyzes the formation of $PGE_2$ from $PGH_2$, which in turn is generated from arachidonic acid by the prostaglandin endoperoxide synthase systems. PGES isozymes have been identified: cytosolic PGES (cPGES), microsomal PGES-1 (mPGES-1) and microsomal PGES-2 (mPGES-2). cPGES is constitutively and ubiquitously expressed and selectively expressed with COX-1. mPGES-1 is induced by proinflammatory stimuli, downregulated by anti-inflammatory glucocorticoids, and functionally coupled with COX-2 in preference to COX-1.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized (biotransformed). The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases (UGT) catalyze the transfer of an activated glucuronic-acid molecule to aromatic alcohols, aliphatic alcohols, carboxylic acids, amines and free sulphydryl groups (e.g. conjugation reactions). Further information on metabolism is available in The Pharmacological Basis of Therapeutics, 9th Edition, McGraw-Hill (1996). In one embodiment, metabolites of the compounds disclosed herein are identified either by administration of compounds to a host and analysis of tissue samples from the host or blood samples or urine samples, or by incubation of compounds with hepatic cells in vitro and analysis of the resulting compounds.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The term "agonist," as used herein, refers to a molecule such as a compound, a drug, an enzyme activator or a hormone modulator which enhances the activity of another molecule or the activity of a receptor site.

The term "antagonist," as used herein, refers to a molecule such as a compound, a drug, an enzyme inhibitor, or a hormone modulator, which diminishes, or prevents the action of another molecule or the activity of a receptor site.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine;

domestic animals such as rabbits, dogs, and cats; laboratory animals including rodents, such as rats, mice and guinea pigs, and the like. In one embodiment of the methods and compositions provided herein, the mammal is a human.

"Bioavailability" refers to the percentage of the weight of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance dosed that is delivered into the general circulation of the animal or human being studied. The total exposure ($AUC_{(0-\infty)}$) of a drug when administered intravenously is usually defined as 100% Bioavailable (F %). "Oral bioavailability" refers to the extent to which 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance is absorbed into the general circulation when the pharmaceutical composition is taken orally as compared to intravenous injection.

"Blood plasma concentration" refers to the concentration of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, in the plasma component of blood of a subject. It is understood that the plasma concentration of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, may vary significantly between subjects, due to variability with respect to metabolism and/or interactions with other therapeutic agents. In one aspect, the blood plasma concentration of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid varies from subject to subject. Likewise, values such as maximum plasma concentration ($C_{max}$) or time to reach maximum plasma concentration ($T_{max}$), or total area under the plasma concentration time curve ($AUC_{(0-\infty)}$) vary from subject to subject. Due to this variability, in one embodiment, the amount necessary to constitute "a therapeutically effective amount" of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance varies from subject to subject.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

A "measurable serum concentration" or "measurable plasma concentration" describes the blood serum or blood plasma concentration, typically measured in mg, µg, or ng of therapeutic agent per ml, dl, or l of blood serum, absorbed into the bloodstream after administration. As used herein, measurable plasma concentrations are typically measured in ng/ml or µg/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Steady state," as used herein, is when the amount of drug administered is equal to the amount of drug eliminated within one dosing interval resulting in a plateau or constant plasma drug exposure.

"Treat" or "treatment" as used herein refers to any treatment of a disorder or disease, such as preventing the disorder or disease from occurring in a subject predisposed to the disorder or disease, but has not yet been diagnosed as having the disorder or disease; inhibiting the disorder or disease, e.g., arresting the development of the disorder or disease, relieving the disorder or disease, causing regression of the disorder or disease, relieving a condition caused by the disease or disorder, or stopping the symptoms of the disease or disorder either prophylactically and/or therapeutically. Thus, as used herein, the term "treat" includes the term "prevent."

Oral Pharmaceutical Compositions/Formulations

In one embodiment, oral pharmaceutical compositions are formulated in a conventional manner using one or more physiologically acceptable carriers (i.e. inactive ingredients) comprising excipients and auxiliaries which facilitate processing of the active compounds into preparations which are used pharmaceutically. Suitable techniques, carriers, and excipients include those found within, for example, *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), herein incorporated by reference in their entirety.

For oral administration, 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance, such as but not limited to the sodium salt, are formulated by combining the active compound with pharmaceutically acceptable carriers or excipients. Such carriers enable 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance to be formulated as tablets, powders, pills, dragees, capsules, liquids, gels, syrups, elixirs, slurries, suspensions and the like, for oral ingestion by a patient to be treated.

The pharmaceutical compositions will include at least one pharmaceutically acceptable carrier, diluent or excipient and 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid as an active ingredient in free-acid or free-base form, or in a pharmaceutically acceptable salt form.

The oral solid dosage formulations described herein include particles of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, or sodium salt thereof, including solvates thereof, existing in crystalline form, amorphous phase, semi-crystalline form, semi-amorphous phase, or mixtures thereof. In one aspect, the oral solid dosage formulations described herein include crystalline particles of sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate, or pharmaceutically acceptable solvate thereof.

The pharmaceutical compositions described herein include: (a) 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance; and one or more of the following: (b) Binders; (c) Disintegrants; (d) Fillers (diluents); (e) Lubricants; (f) Glidants (flow enhancers); (g) Compression aids; (h) Colors; (i) Sweeteners; (j) Preservatives; (k) Suspending/dispersing agents; (l) Film formers/coatings; (m) Flavors; (o) Printing inks.

In one aspect, pharmaceutical compositions described herein include one or more of the following in addition to 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance: (a) Magnesium Stearate; (b) Lactose; (c) Microcrystalline Cellulose; (d) Silicified microcrystalline cellulose; (e) Mannitol; (f) Starch (corn); (g) Silicon Dioxide; (h) Titanium Dioxide; (i) Stearic Acid; (j) Sodium Starch Glycolate; (k) Gelatin; (l) Talc; (m) Sucrose; (n) aspartame; (o) Calcium Stearate; (p) Povidone; (q) Pregelatinized Starch; (r) Hydroxy Propyl Methylcellulose; (s) OPA products (coatings & inks); (t) Croscarmellose; (u) Hydroxy Propyl Cellulose; (v) Ethylcellulose; (w) Calcium Phosphate (dibasic); (x) Crospovidone; (y) Shellac (and Glaze); (z) Sodium carbonate.

In one embodiment, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, silicified microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate.

In one embodiment, the pharmaceutical compositions described herein are formulated into any suitable dosage form, including but not limited to, aqueous oral dispersions, solid oral dosage forms, fast melt formulations, effervescent formulations, lyophilized formulations, tablets, capsules, extended release formulations, inhaled powder, inhaled dispersion, IV formulations.

In some embodiments, formulations provide a therapeutically effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, enabling, for example, once-a-day, twice-a-day (b.i.d.), or three times a day (t.i.d.) administration if desired. In one embodiment, the formulation provides a therapeutically effective amount of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid enabling once-a-day administration.

In one embodiment, 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance is formulated into an immediate release form that provides for once-a-day administration. Generally speaking, one will desire to administer an amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance that is effective to achieve a plasma level commensurate with the concentrations found to be effective in vivo for a period of time effective to elicit a therapeutic effect.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

"Carrier materials" include any excipients in pharmaceutics and should be selected on the basis of compatibility with the active agent and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like.

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol has a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. In one embodiment, plasticizcers such as cellulose or triethyl cellulose are also used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

In one embodiment, combinations of one or more erosion facilitator with one or more diffusion facilitator are also used.

"Diluents" increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "disintegrate" includes both the dissolution and dispersion of the dosage form when contacted with gastrointestinal fluid. "Disintegration agents or disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, microcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, and the like.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" and/or "sweeteners" useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol has a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

In some embodiments, the solid dosage forms described herein are in the form of a tablet, (including an immediate release tablet, an extended release tablet, a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, multiparticulate dosage forms, pellets, or granules.

In other embodiments, the pharmaceutical formulation is in the form of a powder. In still other embodiments, the pharmaceutical formulation is in the form of a tablet, including but not limited to, an immediate release tablet. Additionally, pharmaceutical formulations described herein are administered as a single dosage or in multiple dosages.

In some embodiments, the pharmaceutical formulation is administered in two, or three, or four tablets.

In some embodiments, solid dosage forms, e.g., tablets, effervescent tablets, and capsules, are prepared by mixing 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance with one or more pharmaceutical excipients to form a bulk blend composition. When referring to these bulk blend compositions as homogeneous, it is meant that the 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance particles are dispersed evenly throughout the composition so that the composition is capable of being readily subdivided into equally effective unit dosage forms, such as tablets, pills, or capsules. In one embodiment, the individual unit dosages also include film coatings, which disintegrate upon oral ingestion or upon contact with diluent. In one embodiment, these formulations are manufactured by conventional techniques.

Conventional techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms described herein include the 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance compositions described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance is rapidly absorbed in the upper gastrointestinal tract, and thus there is a strong correlation between the rate of dissolution and bioavailability. Thus, it is important to optimize the rate of dissolution in biological matrices in order to enhance in vivo absorption. In order to release the 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, microcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that is filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself acts as moderate binder.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Non water-soluble diluents are compounds typically used in the formulation of pharmaceuticals, such as calcium phosphate, calcium sulfate, starches, modified starches and microcrystalline cellulose, and microcellulose (e.g., having a density of about 0.45 g/cm$^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol has a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that are included in solid dosage forms described herein.

Compressed tablets are solid dosage forms prepared by compacting the bulk blend formulations described above. In various embodiments, compressed tablets which are designed to dissolve in the mouth will include one or more flavoring agents. In other embodiments, the compressed tablets will include a film surrounding the final compressed tablet. In some embodiments, the film coating aids in patient compliance (e.g., Opadry® coatings or sugar coating). Film coatings comprising Opadry® typically range from about 1% to about 3% of the tablet weight. In other embodiments, the compressed tablets include one or more excipients.

In one embodiment, a capsule is prepared, e.g., by placing the bulk blend formulation described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating. In some embodiments, the therapeutic dose is split into multiple (e.g., two, three, or four) capsules. In some embodiments, the entire dose of the formulation is delivered in a capsule form.

In one aspect, 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance and one or more excipients are dry blended and compressed into a mass, such as a tablet, having a hardness sufficient to provide a pharmaceutical composition that substantially disintegrates within less than about 10 minutes, less than about 15 minutes, less than about 20 minutes, less than about 25 minutes, less than about 30 minutes, less than about 35 minutes, or less than about 40 minutes, after oral administration, thereby releasing the 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance formulation into the gastrointestinal fluid.

In other embodiments a powder comprising the 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance formulations described herein are formulated to include one or more pharmaceutical excipients and flavors. Such a powder is prepared, for example, by mixing the 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance formulation and optional pharmaceutical excipients to form a bulk blend composition. Additional embodiments also comprise a suspending agent and/or a wetting agent. This bulk blend is uniformly subdivided into unit dosage packaging or multi-dosage packaging units. The term "uniform" means the homogeneity of the bulk blend is substantially maintained during the packaging process.

In still other embodiments, effervescent powders are prepared. Effervescent salts have been used to disperse medicines in water for oral administration. Effervescent salts are granules or coarse powders containing a medicinal agent in a dry mixture, usually composed of sodium bicarbonate, citric acid and/or tartaric acid. When such salts of the claimed compound are added to water, the acids and the base react to liberate carbon dioxide gas, thereby causing "effervescence."

Examples of effervescent salts include, e.g., the following ingredients: sodium bicarbonate or a mixture of sodium bicarbonate and sodium carbonate, citric acid and/or tartaric acid. In one embodiment, any acid-base combination that results in the liberation of carbon dioxide is used in place of the combination of sodium bicarbonate and citric and tartaric acids, as long as the ingredients were suitable for pharmaceutical use and result in a pH of about 6.0 or higher.

The method of preparation of the effervescent granules described herein employs three basic processes: wet granulation, dry granulation and fusion. The fusion method is used for the preparation of most commercial effervescent powders. It should be noted that, although these methods are intended for the preparation of granules, the formulations of effervescent salts described herein, in one embodiment, are also prepared as tablets, according to technology for tablet preparation.

Wet granulation is one the oldest method of granule preparation. The individual steps in the wet granulation process of tablet preparation include milling and sieving of the ingredients, dry powder mixing, wet massing, granulation, drying and final grinding. In various embodiments, the composition is added to the other excipients of the pharmaceutical formulation after they have been wet granulated.

Dry granulation involves compressing a powder mixture into a rough tablet or "slug" on a heavy-duty rotary tablet press. The slugs are then broken up into granular particles by a grinding operation, usually by passage through an oscillation granulator. The individual steps include mixing of the powders, compressing (slugging) and grinding (slug reduction or granulation). No wet binder or moisture is involved in any of the steps. In some embodiments, the formulation is dry granulated with other excipients in the pharmaceutical formulation. In other embodiments, the formulation is added to other excipients of the pharmaceutical formulation after they have been dry granulated.

In some embodiments, pharmaceutical formulations are provided comprising the 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance and at least one dispersing agent or suspending agent for oral administration to a subject. In one embodiment, the formulation is a powder and/or granules for suspension, and upon admixture with water, a substantially uniform suspension is obtained.

A suspension is "substantially uniform" when it is mostly homogenous, that is, when the suspension is composed of approximately the same concentration of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance at any point throughout the suspension (USP Chapter 905).

In one embodiment, liquid formulation dosage forms for oral administration are aqueous suspensions selected from, but not limited to, pharmaceutically acceptable aqueous oral dispersions, emulsions, solutions, and syrups. See, e.g., Singh et al., *Encyclopedia of Pharmaceutical Technology*, $2^{nd}$ Ed., pp. 754-757 (2002). In addition to including 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance, the liquid dosage forms include additives, such as: (a) disintegrating agents; (b) dispersing agents; (c) wetting agents; (d) at least one preservative, (e) viscosity enhancing agents, (f) at least one sweetening agent, and/or (g) at least one flavoring agent.

In one embodiment, the aqueous suspensions and dispersions described herein remain in a homogenous state, as defined above by USP Chapter 905, for at least 4 hours. The homogeneity should be determined by a sampling method consistent with regard to determining homogeneity of the entire composition. In one embodiment, an aqueous suspension is re-suspended into a homogenous suspension by physical agitation lasting less than 1 minute. In another embodiment, an aqueous suspension is re-suspended into a homogenous suspension by physical agitation lasting less than 45 seconds. In yet another embodiment, an aqueous suspension is re-suspended into a homogenous suspension by physical agitation lasting less than 30 seconds. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin- Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions described herein include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth. In one embodiment, the aqueous liquid dispersion comprises methylparaben and propylparaben in a concentration ranging from about 0.0001% to about 0.5% the volume of the aqueous dispersion. In another embodiment, the aqueous liquid dispersion comprises methylparaben and propylparaben in a concentration ranging from about 0.0002% to about 0.2% the volume of the aqueous dispersion. In yet another embodiment, the aqueous liquid dispersion comprises methylparaben and propylparaben in a concentration ranging from about 0.0003% to about 0.1% the volume of the aqueous dispersion.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In one embodiment, the aqueous liquid dispersion comprises a sweetening agent or flavoring agent in a concentration ranging from about 0.001% to about 1.0% the volume of the aqueous dispersion. In another embodiment, the aqueous liquid dispersion comprises a sweetening agent or flavoring agent in a concentration ranging from about 0.005% to about 0.5% the volume of the aqueous dispersion. In yet another embodiment, the aqueous liquid dispersion comprises a sweetening agent or flavoring agent in a concentration ranging from about 0.01% to about 1.0% the volume of the aqueous dispersion.

In one embodiment, the liquid formulations also include inert diluents, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

It is to be appreciated that there is overlap between the above-listed additives used in the aqueous dispersions or suspensions described herein, since a given additive is often classified differently by different practitioners in the field. Thus, the above-listed additives should be taken as merely exemplary, and not limiting, of the types of additives that are included in formulations described herein.

In one embodiment, the aqueous suspensions, solutions or dispersions described herein include 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance at a concentration of about 5 mg/ml to about 50 mg/ml of solution.

In another embodiment, the aqueous suspensions, solutions or dispersions described herein include 3-[5-(pyridin-2-ylmethoxy)-3-(2-methyl-2-propylthio)-1-[4-(2-methoxy-pyridin-5-yl)benzyl]-indol-2-yl]-2,2-dimethyl-propionic acid drug substance at a concentration of about 5 mg/ml to about 30 mg/ml of solution.

In another embodiment, the aqueous suspensions, solutions or dispersions described herein include 3-[5-(pyridin-2-ylmethoxy)-3-(2-methyl-2-propylthio)-1-[4-(2-methoxy-pyridin-5-yl)benzyl]-indol-2-yl]-2,2-dimethyl-propionic acid drug substance at a concentration of about 10 mg/ml of solution.

The aqueous dispersions described herein are beneficial for the administration to infants (less than 2 years old), children under 10 years of age and any patient group that is unable to swallow or ingest solid oral dosage forms.

For buccal or sublingual administration, in one embodiment, the compositions take the form of tablets, lozenges, or gels formulated in a conventional manner (see e.g. U.S. Pat. Nos. 4,229,447, 4,596,795, 4,755,386, and 5,739,136).

In one embodiment, dragee cores are prepared with suitable coatings. For this purpose, concentrated sugar solutions are used, which optionally contain gum arabic, talc, polyvinylpyrrolidone, carbopol gel, polyethylene glycol, and/or titanium dioxide, lacquer solutions, and suitable organic solvents or solvent mixtures. In one embodiment, dyestuffs or pigments are added to the tablets or dragee coatings for identification or to characterize different combinations of active compound doses.

In one embodiment, pharmaceutical preparations which are used orally include push-fit capsules made of gelatin, as well as soft, sealed capsules made of gelatin and a plasticizer, such as glycerol or sorbitol. In one embodiment, the push-fit capsules contain the active ingredients in admixture with filler such as lactose, binders such as starches, and/or lubricants such as talc or magnesium stearate and, optionally, stabilizers. In one embodiment, in soft capsules, the active compounds are dissolved or suspended in suitable liquids, such as fatty oils, liquid paraffin, or liquid polyethylene glycols. In addition, in one embodiment, stabilizers areadded. All formulations for oral administration should be in dosages suitable for such administration.

Liquid compositions illustratively take the form of a liquid where the agent is present in solution, in suspension or both. In one embodiment, the liquid composition is aqueous.

In one embodiment, aqueous suspensions also contain one or more polymers as suspending agents. Useful polymers include water-soluble polymers such as cellulosic polymers, e.g., hydroxypropyl methylcellulose, and water-insoluble polymers such as cross-linked carboxyl-containing polymers. In one embodiment, useful compositions also comprise an mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

In one embodiment, pharmaceutical compositions also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In one embodiment, liquid pharmaceutical compositions also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfate anions; suitable salts include sodium chloride, potassium chloride, sodium thiosulfate, sodium bisulfate and ammonium sulfate.

In one embodiment, pharmaceutical compositions also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other compositions include one or more antioxidants to enhance chemical stability where required. Suitable antioxidants include, by way of example only, ascorbic acid, tocopherol, and sodium metabisulfite.

In one embodiment, aqueous suspension compositions are packaged in single-dose non-reclosable containers. Alternatively, multiple-dose reclosable containers are used, in which case it is typical to include a preservative in the composition.

Pharmacokinetic Analysis

In one embodiment, any standard pharmacokinetic protocol is used to determine blood plasma concentration profile in humans following administration of a formulation described herein (that contains 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance), and thereby establish whether that formulation meets the pharmacokinetic criteria set out herein. For example in one aspect, a randomized single-dose crossover study is performed using a group of healthy adult human subjects. The number of subjects should be sufficient to provide adequate control of variation in a statistical analysis, and is typically about 10 or greater, although for certain purposes a smaller group suffices. Each subject receives administration at time zero a single dose (e.g., a dose containing about 50 mg, about 150 mg, about 300 mg, about 450 mg, about 600 mg, or about 1000 mg of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance) of a test formulation of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance, normally at around 8 am following an overnight fast. The subjects continue to fast and remain in an upright position for about 4 hours after administration of the formulation. Blood samples are collected from each subject prior to administration (e.g., 15 minutes) and at several intervals after administration. For the present purpose it is preferred to take several samples within the first hour and to sample less frequently thereafter. Illustratively, blood samples are collected at 0 (pre-dose), 0.25, 0.5, 1, 2, 3, 4, 6, 8, 12, and 16 hours after administration and, 24, 36, 48, 60 and 72 hours after administration. If the same subjects are to be used for study of a second test formulation, a period of at least 10 days should elapse before administration of the second formulation. Plasma is separated from the blood samples by centrifugation and the separated plasma is analyzed for 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid by a validated high performance liquid chromatography/tandem weight spectrometry (LC/APCI-MS/MS) procedure such as, for example, Ramu et al., *Journal of Chromatography B*, 751 (2001) 49-59).

Any formulation giving an acceptable pharmacokinetic profile is suitable for administration according to the present methods.

Methods of Dosing and Treatment Regimens

In one embodiment, the compositions containing 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance described herein is administered for prophylactic and/or therapeutic treatments. In therapeutic applications, the compositions are administered to a patient already suffering from a disease or condition, in an amount sufficient to at least partially arrest at least one of the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance described herein are administered to a patient susceptible to or otherwise at risk of a particular disease, disorder or condition. Such an amount is defined to be a prophylactically effective amount or dose. In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician. In one aspect, prophylactic treatment occurs when the drug is administered to a patient who is not experiencing symptoms but has previously experienced symptoms of a particular disease, disorder or condition. In one aspect, prophylactic treatment occurs when the drug is administered to a patient who is not experiencing symptoms but has who has been diagnosed (including via the use of genetic tests) a particular disease, disorder or condition. In another aspect, prophylactic treatment occurs when a patient is kept in remission.

In one embodiment, in the case wherein the patient's condition does not improve, upon the doctor's discretion the administration of the compounds is administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds is given continuously; alternatively, the dose of drug being administered is temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday is from about 10% to about 100%, including by way of example only about 10%, 15%, 20%, 25%, 30%, 35%, 40%, 45%, 50%, 55%, 60%, 65%, 70%, 75%, 80%, 85%, 90%, 95%, or about 100%.

Once improvement of the patient's conditions has occurred, a maintenance dose is administered if necessary. In one embodiment, subsequently, the dosage or the frequency of administration, or both, is reduced, as a function of the symptoms, to a level at which the improved disease, disorder or condition is retained. In one embodiment, patients, however, require intermittent treatment on a long-term basis upon any recurrence of symptoms.

The amount of a given agent that will correspond to such an amount will vary depending upon factors such as the particular compound, disease condition and its severity, the identity (e.g., weight) of the subject or host in need of treatment, but nevertheless be determined according to the particular circumstances surrounding the case, including, e.g., the specific agent being administered, the route of administration, the condition being treated, and the subject or host being treated. In general, however, doses employed for adult human treatment will typically be in the range of about 10 mg per day to about 1000 mg per day. In one aspect, the dose will be in the range of about 50 mg per day to about 600 mg per day. In one aspect, the dose will be about 50 mg per day, about 100 mg per day, about 150 mg per day, about 200 mg per day, about 250 mg per day, about 300 mg per day, about 350 mg per day, about 400 mg per day, about 500 mg per day, or about 600 mg per day. In one embodiment, the desired dose is conveniently presented in a single dose or as divided doses administered simultaneously (or over a short period of time) or at appropriate intervals, for example as two, three, four or more sub-doses per day.

In one embodiment, the pharmaceutical compositions described herein are in unit dosage forms suitable for single administration of precise dosages. In unit dosage form, the formulation is divided into unit doses containing appropriate quantities of the active drug. In one embodiment, the unit dosage is in the form of a package containing discrete quantities of the formulation. Non-limiting examples are packaged tablets or capsules, and powders in vials or ampoules. In one embodiment, aqueous suspension compositions are packaged in single-dose non-reclosable containers. Alternatively, multiple-dose reclosable containers are used, in which case it is typical to include a preservative in the composition.

Leukotriene-Dependent or Leukotriene Mediated Diseases or Conditions

In accordance with one aspect, compositions and methods described herein include compositions and methods for treating, preventing, reversing, halting or slowing the progression of leukotriene-dependent or leukotriene mediated diseases or conditions once it becomes clinically evident, or treating the symptoms associated with or related to leukotriene-dependent or leukotriene mediated diseases or conditions, by administering to the subject 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance, or pharmaceutical composition or medicament thereof. In one embodiment, the subject already has a leukotriene-dependent or leukotriene mediated disease or condition at the time of administration, or be at risk of developing a leukotriene-dependent or leukotriene mediated disease or condition (e.g., those symptoms described in the medical literature for such diseases).

In one embodiment, the activity of 5-lipoxygenase activating protein in a mammal is directly or indirectly modulated by the administration of (at least once) an effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance, to a mammal. Such modulation includes, but is not limited to, reducing and/or inhibiting the activity of 5-lipoxygenase activating protein. In addition, in one embodiment, the activity of leukotrienes in a mammal is directly or indirectly modulated, including reducing and/or inhibiting, by the administration of (at least once) an effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance to a mammal. Such modulation includes, but is not limited to, reducing and/or inhibiting the activity of 5-lipoxygenase activating protein.

In one embodiment, prevention and/or treatment leukotriene-dependent or leukotriene mediated diseases or conditions comprises administering to a mammal at least once an effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance. By way of example, the prevention and/or treatment of inflammation diseases or conditions comprises administering to a mammal at least once an effective amount of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance. Leukotriene-dependent or leukotriene mediated diseases or conditions that is treated by a method comprising administering to a mammal at least once an effective amount of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance, include, but are not limited to, inflammatory diseases and disorders, respiratory diseases and disorder.

By way of example only, included in the prevention/treatment methods described herein are methods for treating respiratory diseases comprising administering to the mammal at least once an effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance. By way of example the respiratory disease is asthma. In addition, the respiratory disease includes, but is not limited to, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, allergic rhinitis, vascular responses, endotoxin shock, fibrogenesis, pulmonary fibrosis, allergic diseases, chronic inflammation, and adult respiratory distress syndrome.

By way of example only, included in such treatment methods are methods for preventing chronic obstructive pulmonary disease comprising administering to the mammal at least once an effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance. In addition, chronic obstructive pulmonary disease includes, but is not limited to, chronic bronchitis or emphysema, pulmonary hypertension, interstitial lung fibrosis and/or airway inflammation and cystic fibrosis.

By way of example only, included in such treatment methods are methods for preventing increased mucosal secretion and/or edema in a disease or condition comprising administering to the mammal at least once an effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance.

By way of example only, included in the prevention/treatment methods described herein are methods for preventing eosinophil and/or basophil and/or dendritic cell and/or neutrophil and/or monocyte recruitment comprising administering at least once to the mammal an effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance.

By way of example only, included in the prevention/treatment methods described herein are methods for preventing ocular inflammation and allergic conjunctivitis, vernal keratoconjunctivitis, and papillary conjunctivitis comprising administering at least once to the mammal an effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance.

Combination Therapies

In one embodiment, the compositions and methods described herein are also used in conjunction with other therapeutic reagents that are selected for their particular usefulness against the condition that is being treated. In general, the compositions described herein and, in embodiments where combinational therapy is employed, other agents do not have to be administered in the same pharmaceutical composition, and are, because of different physical and chemical characteristics, administered by different routes. In one embodiment, the initial administration is made according to established protocols, and then, based upon the observed effects, the dosage, modes of administration and times of administration, further modified.

The particular choice of compounds used will depend upon the diagnosis of the attending physicians and their judgment of the condition of the patient and the appropriate treatment protocol. The compounds are administered concurrently (e.g., simultaneously, essentially simultaneously or within the same treatment protocol) or sequentially, depending upon the nature of the proliferative disease, the condition of the patient, and the actual choice of compounds used. The determination of the order of administration, and the number of repetitions of administration of each therapeutic agent during a treatment protocol, is based upon evaluation of the disease being treated and the condition of the patient.

In one embodiment, it is understood that the dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in one embodiment, the dosage regimen actually employed varies widely and therefore deviates from the dosage regimens set forth herein.

The formulations described herein are administered and dosed in accordance with good medical practice, taking into account the clinical condition of the individual patient, the method of administration, scheduling of administration, and other factors known to medical practitioners.

Contemplated pharmaceutical compositions provide a therapeutically effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid enabling, for example, once-a-day, twice-a-day, three times a day, etc. administration if desired. In one aspect, pharmaceutical compositions provide a therapeutically effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid enabling once-a-day dosing.

In certain instances, it is appropriate to administer 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance in combination with another therapeutic agent.

By way of example only, the therapeutic effectiveness of one of the compounds described herein are enhanced by administration of an adjuvant (i.e., by itself the adjuvant has minimal therapeutic benefit, but in combination with another therapeutic agent, the overall therapeutic benefit to the patient is enhanced). Or, by way of example only, the benefit experienced by a patient is increased by administering one of the compounds described herein with another therapeutic agent (which also includes a therapeutic regimen) that also has therapeutic benefit. By way of example only, in a treatment for asthma involving administration of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance, increased therapeutic benefit results by also providing the patient with other therapeutic agents or therapies for asthma. In any case, regardless of the disease, disorder or condition being treated, the overall benefit experienced by the patient is either simply additive of the two therapeutic agents or the patient experiences a synergistic benefit.

Therapeutically-effective dosages vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature.

A combination treatment regimen encompasses treatment regimens in which administration of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance is initiated prior to, during, or after treatment with a second agent, and continues until any time during treatment with the second agent or after termination of treatment with the second agent. It also includes treatments in which 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance and the second agent being used in combination are administered simultaneously or at different times and/or at decreasing or increasing intervals during the treatment period. Combination treatment further includes periodic treatments that start and stop at various times to assist with the clinical management of the patient.

In accordance with another aspect, the pharmaceutical compositions disclosed herein are used to treat respiratory diseases, e.g. asthma, and to induce bronchodilation in a subject. In one embodiment, pharmaceutical compositions disclosed herein are used to treat a subject suffering from a vascular inflammation-driven disorder.

In one embodiment, combination therapies described herein are used as part of a specific treatment regimen intended to provide a beneficial effect from the co-action of a FLAP inhibitor, e.g. 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance, and a concurrent treatment. It is understood that the dosage regimen to treat, prevent, or ameliorate the condition(s) for which relief is sought, is modified, in one embodiment, in accordance with a variety of factors. These factors include the type of respiratory disorder and the type of bronchodilation from which the subject suffers, as well as the age, weight, sex, diet, and medical condition of the subject. Thus, the dosage regimen actually employed, in one embodiment, varies widely and therefore deviates from the dosage regimens set forth herein.

For combination therapies described herein, dosages of the co-administered compounds will of course vary depending on the type of co-drug employed, on the specific drug employed, on the disease or condition being treated and so forth.

In any case, the multiple therapeutic agents (one of which is 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance) are administered either in any order or even simultaneously. If simultaneously, the multiple therapeutic agents are provided, in one embodiment, in a single, unified form, or in multiple forms (by way of example only, either as a single pill or as two separate pills). In one embodiment, one of the therapeutic agents is given in multiple doses, or both are given as multiple doses. If not simultaneous, the timing between the multiple doses varies from more than zero weeks to less than four weeks. In addition, the combination methods, compositions and formulations are not to be limited to the use of only two agents; the use of multiple therapeutic combinations are also envisioned.

3-[5-(Pyridin-2-ylmethoxy)-3-(2-methyl-2-propylthio)-1-[4-(2-methoxypyridin-5-yl)benzyl]-indol-2-yl]-2,2-dimethyl-propionic acid drug substance, and combination therapies thereof, in one embodiment, are administered before, during or after the occurrence of a disease or condition, and the timing of administering the composition containing a compound vary. Thus, for example, the compounds are used as a prophylactic and can be administered continuously to subjects with a propensity to develop conditions or diseases in order to prevent the occurrence of the disease or condition. In one embodiment, the compounds and compositions are administered to a subject during or as soon as possible after the onset of the symptoms. In one embodiment, the administration of the compounds is initiated within the first 48 hours of the onset of the symptoms, preferably within the first 48 hours of the onset of the symptoms, more preferably within the first 6 hours of the onset of the symptoms, and most preferably within 3 hours of the onset of the symptoms. In one embodiment, the initial administration is via oral administration, such as, for example, a pill, a capsule, a tablet, a solution, a suspension, and the like, or combination thereof. 3-[5-(Pyridin-2-ylmethoxy)-3-(2-methyl-2-propylthio)-1-[4-(2-methoxypyridin-5-yl)benzyl]-indol-2-yl]-2,2-dimethyl-propionic acid is preferably administered as soon as is practicable after the onset of a disease or condition is detected or suspected, and for a length of time necessary for the treatment of the disease, such as, for example, from about 1 month to about 3 months. In one embodiment, the length of treatment varies for each subject, and the length determined using known criteria. For example, the compound or a formulation containing the compound is administered for at least 2 weeks, preferably about 1 month to about 5 years, and more preferably from about 1 month to about 3 years.

By way of example, therapies which combine 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance, with inhibitors of leukotriene synthesis or leukotriene receptor antagonists, either acting at the same or other points in the leukotriene synthesis pathway, are particularly useful for treating leukotriene-dependent or leukotriene mediated diseases or conditions. In addition, by way of example, therapies which combine 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance, with inhibitors of inflammation are particularly useful for treating leukotriene-dependent or leukotriene mediated diseases or conditions.

Agents to Treat Respiratory Diseases or Conditions

In another embodiment described herein, methods for the treatment of leukotriene-dependent or leukotriene mediated conditions or diseases include administering to a patient 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance in combination with other therapeutic agents that are used in the treatment of respiratory conditions or disorders, such as, but not limited to asthma. Therapeutic agents used in the treatment of respiratory conditions and disorders, such as, but not limited to asthma, include: glucocorticoids, such as, ciclesonide, beclomethasone dipropionate, budesonide, flunisolide, fluticasone propionate, fluticasone furoate, mometasone furoate, and triamcinolone; leukotriene modifiers, such as, montelukast, zafirlukast, pranlukast, and zileuton; mast cell stabilizers, such as, cromoglicate (cromolyn), and nedocromil; antimuscarinics/anticholinergics, such as, ipratropium, oxitropium, and tiotropium; methylxanthines, such as, theophylline and aminophylline; antihistamines, such as, mepyramine (pyrilamine), antazoline, diphenhydramine, carbinoxamine, doxylamine, clemastine, dimenhydrinate, pheniramine, chlorphenamine (chlorpheniramine), dexchlorphenamine, brompheniramine, triprolidine, cyclizine, chlorcyclizine, hydroxyzine, meclizine, promethazine, alimemazine (trimeprazine), cyproheptadine, azatadine, ketotifen, acrivastine, astemizole, cetirizine, loratadine, mizolastine, terfenadine, fexofenadine, levocetirizine, desloratadine, fexofenadine; omalizumab, olapatidine and azelastine, an IgE blocker; beta2-adrenergic receptor agonists, such as: short acting beta2-adrenergic receptor agonists, such as, salbutamol (albuterol), levalbuterol, terbutaline, pirbuterol, procaterol, metaproterenol, fenoterol, bitolterol mesylate; and long-acting beta2-adrenergic receptor agonists, such as, salmeterol, formoterol, indacaterol and bambuterol.

In one aspect, 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance is administered in combination with one or more agents used to treat asthma, including, but not limited to: combination Inhalers (fluticasone propionate and salmeterol xinafoate (e.g. Advair); budesonide and formoterol fumarte (e.g. Symbicort); and indacaterol and mometasone furoate); inhaled Beta-2 agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler; inhaled corticosteroids (beclomethasone oral inhalation; budesonide inhalation solution; budesonide inhaler; flunisolide oral inhalation; fluticasone inhalation aerosol; fluticasone powder for oral inhalation; mometasone inhalation powder; triamcinolone oral inhalation); leukotriene modifiers (montelukast; zafirlukast; zileuton); mast cell stabilizers (cromolyn inhaler; nedocromil oral inhalation); monoclonal antibodies (omalizumab); oral Beta-2 agonists (albuterol oral syrup; albuterol oral tablets; metaproterenol; terbutaline); bronchodilator (aminophylline; oxtriphylline; theophylline).

In one aspect, 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance is administered in combination with one or more agents used to treat allergy, including, but not limited to: antihistamine and decongestant combinations (cetirizine and pseudoephedrine; desloratadine and pseudoephedrine ER; fexofenadine and pseudoephedrine; loratadine and pseudoephedrine); antihistamines (azelastine nasal spray; brompheniramine; brompheniramine oral suspension; carbinoxamine; cetirizine; chlorpheniramine; clemastine; desloratadine; dexchlorpheniramine ER; dexchlorpheniramine oral syrup; diphenhydramine oral; fexofenadine; loratadine; promethazine); decongestants (pseudoephedrine); leukotriene modifiers (montelukast; montelukast granules); nasal anticholinergics (ipratropium); nasal corticosteroids (beclomethasone nasal inhalation; budesonide nasal inhaler; flunisolide nasal inhalation; fluticasone nasal inhalation; mometasone nasal spray; triamcinolone nasal inhalation; triamcinolone nasal spray); nasal decongestants (phenylephrine); nasal mast cell stabilizers (cromolyn nasal spray).

In one aspect, 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance is administered in combination with one or more agents used to treat chronic obstructive pulmonary disease (COPD), including, but not limited to: anticholinergics-ipratropium bromide oral inhalation); combination Inhalers (albuterol and ipratropium (e.g. Combivent, DuoNeb); fluticasone and salmeterol oral inhalation (e.g. Advair)); corticosteroids (dexamethasone tablets; fludrocortisone acetate; hydrocortisone tablets; methylprednisolone; prednisolone liquid; prednisone oral; triamcinolone oral); inhaled Beta-2 Agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler); inhaled Corticosteroids (beclomethasone oral inhalation; budesonide inhalation solution; budesonide inhaler; flunisolide oral inhalation; fluticasone inhalation aerosol; fluticasone powder for oral inhalation; triamcinolone oral inhalation); mukolytics (guaifenesin); oral Beta-2 agonists (albuterol oral syrup; albuterol oral tablets; metaproterenol; terbutaline); bronchodilator (aminophylline; oxtriphylline; theophylline).

In one embodiment, 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance is administered to a patient in combination with norastemizole. In one embodiment, 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance is administered to a patient in combination with desloratadine. In one embodiment, 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance is administered to a patient in combination with loratadine. In one embodiment, 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance is administered to a patient in combination with terfenadine.

In one embodiment, 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance is administered to a patient in combination with cetirizine. In one embodiment, 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance is administered to a patient in combination with (−) cetirizine. In one embodiment, 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance is administered to a patient in combination with (+) cetirizine.

In one embodiment, 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance is administered to a patient in combination with inhaled corticosteroids.

In one embodiment, 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance is administered to a patient in combination with beta2-adrenergic receptor agonists. In one embodiment, 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance is administered to a patient in combination with short acting beta2-adrenergic receptor agonists. In one embodiment, 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance is administered to a patient in combination with long-acting beta2-adrenergic receptor agonists.

Leukotriene Receptor Antagonists

In another embodiment described herein, methods for treatment of leukotriene-dependent or leukotriene mediated conditions or diseases includes administration to a patient 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance in combination with leukotriene receptor antagonists including, but are not limited to, $CysLT_1/CysLT_2$ dual receptor antagonists and $CysLT_1$ receptor anatagonists. In another embodiment described herein, methods for treatment of leukotriene-dependent or leukotriene mediated conditions or diseases includes administered to a patient compounds, pharmaceutical compositions, or medicaments described herein in combination with a $CysLT_1/CysLT_2$ dual receptor antagonist. $CysLT_1/CysLT_2$ dual receptor antagonists include, but are not limited to, BAY u9773, Cuthbert et al EP 00791576 (published 27 Aug. 1997), DUO-LT (Galczenski et al, D38, Poster F4 presented at American Thoracic Society, May 2002) and Tsuji et al, *Org. Biomol. Chem.*, 1, 3139-3141, 2003. In one embodiment, for a particular patient, the most appropriate formulation or method of use of such combination treatments depends on the type of leukotriene-dependent or leukotriene mediated disorder, the time period in which the 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance acts to treat the disorder and the time period in which the $CysLT_1/CysLT_2$ dual receptor antagonist acts to inhibit CysLT receptor activity. By way of example only, such combination treatments are used for treating a patient suffering from a respiratory disorder.

In another embodiment described herein, methods for treatment of leukotriene-dependent or leukotriene mediated conditions or diseases includes administered to a patient compounds, pharmaceutical compositions, or medicaments described herein in combination with a $CysLT_1$ receptor antagonist. $CysLT_1$ receptor antagonists include, but are not limited to, zafirlukast ("Accolate™"), montelukast ("Singulair™"), prankulast ("Onon™"), and derivatives or analogs thereof. In one embodiment, such combinations are used to treat leukotriene-dependent or leukotriene mediated disorder, including respiratory disorders.

In one embodiment, the co-administration of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance with a $CysLT_1$ receptor antagonist or a dual $CysLT_1/CysLT_2$ receptor antagonist has therapeutic benefit over and above the benefit derived from the administration of a either 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance or a $CysLT_1R$ antagonist alone. In the case that substantial inhibition of leukotriene production has undesired effects, partial inhibition of this pathway through the amelioration of the effects of the proinflammatory $LTB_4$ and cysteinyl leukotrienes combined with the block of the $CysLT_1$ receptor and/or dual $CysLT_1/CysLT_2$ receptor block affords substantial therapeutic benefits, particularly for respiratory diseases.

Anti-Inflammatory Agents

In another embodiment described herein, methods for treatment of leukotriene-dependent or leukotriene mediated conditions or diseases include administering to a patient 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance in combination with an anti-inflammatory agent including, but not limited to, non-steroidal anti-inflammatory drugs (NSAIDs) and corticosteroids (glucocorticoids).

NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, fluorobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745,337 and NS398).

Corticosteroids, include, but are not limited to: betamethasone (Celestone), prednisone (Deltasone), alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

Corticosteroids do not directly inhibit leukotriene production, therefore co-dosing with steroids, in one embodiment, provide additional anti-inflammatory benefit.

Some commercially available anti-inflammatories include, but are not limited to: Arthrotec® (diclofenac and misoprostol), Asacol®, Salofalk® (5-aminosalicyclic acid), Auralgan® (antipyrine and benzocaine), Azulfidine® (sulfasalazine), Daypro® (oxaprozin), Lodine® (etodolac), Ponstan® (mefenamic acid), Solumedrol® (methylprednisolone), Bayer®, Bufferin® (aspirin), Indocin® (indomethacin), Vioxx® (rofecoxib), Celebrex® (celecoxib), Bextra® (valdecoxib), Arcoxia® (etoricoxib), Prexige® (lumiracoxib), Advil®, Motrin® (ibuprofen), Voltaren® (diclofenac), Orudis® (ketoprofen), Mobic® (meloxicam), Relafen® (nabumetone), Aleve®, Naprosyn® (naproxen), Feldene® (piroxicam).

In another embodiment described herein, methods for treatment of leukotriene-dependent or leukotriene mediated conditions or diseases include administering to a patient 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance in combination with an anti-inflammatory agent including, but not limited to polyunsaturated fatty acids (PUFAs) such as docosahexanoic acid (DHA), eicosapentanoic acid (EPA) and alpha-linolenic acid (ALA).

By way of example, asthma is a chronic inflammatory disease characterized by pulmonary eosinophilia and airway hyperresponsiveness. Zhao et al., *Proteomics*, Jul. 4, 2005. In patients with asthma, leukotrienes may be released from mast cells, eosinophils, and basophils. The leukotrienes are involved in contraction of airway smooth muscle, an increase in vascular permeability and mucus secretions, and have been reported to attract and activate inflammatory cells in the airways of asthmatics (Siegel et al., ed., Basic Neurochemistry, Molecular, Cellular and Medical Aspects, Sixth Ed., Lippincott Williams & Wilkins, 1999). Thus, in another embodiment described herein, the methods for treatment of respiratory diseases include administering to a patient compounds, pharmaceutical compositions, or medicaments described herein in combination with an anti-inflammatory agent.

In another embodiment described herein, methods for treatment of leukotriene-dependent or leukotriene mediated conditions or diseases include administering to a patient 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance in combination with NSAIDs and NO-donors or NSAIDs and proton-pump inhibitors.

UGT Inhibitors

In one embodiment, 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance is co-administered with one or more agents that are inhibitors of UDP-glucuronosyltransferase (UGT) (see, e.g. U.S. 2003/0215462; U.S. 2004/0014648). In such a case, co-administration of a UGT inhibitor allows for lower doses of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance to be administered.

Diagnostic Methods for Patient Identification

The screening of "leukotriene-responsive patients" which are selected for treatment with 3-[5-(pyridin-2-ylmethoxy)-3-(2-methyl-2-propylthio)-1-[4-(2-methoxypyridin-5-yl) benzyl]-indol-2-yl]-2,2-dimethyl-propionic acid drug substance, or pharmaceutical compositions or medicaments described herein, is accomplished using techniques and methods described herein. Such techniques and methods include, by way of example, evaluation of gene haplotypes (genotype analysis), monitoring/measurement of biomarkers (phenotype analysis), monitoring/measurement of functional markers (phenotype analysis), which indicate patient response to modulators of the leukotriene pathway, or any combination thereof.

Genotype Analysis: FLAP Polymorphisms

Human FLAP has been purified and cloned and is an 18 kilodalton membrane-bound protein which is most highly expressed in human neutrophils. The FLAP gene is located at 13q12 and the gene has been linked to increased risk for both myocardial infarction and stroke in several populations. A number of polymorphisms and haplotypes in the gene encoding FLAP have been identified in individuals (U.S. Patent Application 2005113408; Sayers, *Clin. Exp. Allergy*, 33(8): 1103-10, 2003; Kedda, et al., *Clin. Exp. Allergy*, 35(3):332-8, 2005). Previously, polymorphisms in certain genes have been demonstrated to correlate with responsiveness to given therapies, for example, the responsiveness of cancers to particular chemotherapeutic agents (Erichsen, et al., *Br. J. Cancer*, 90(4):747-51, 2004; Sullivan, et al., *Oncogene*, 23(19):3328-37, 2004). Therefore, in one embodiment, patients who are under consideration for treatment with the novel FLAP inhibitors described herein, or drug combinations that include such novel FLAP inhibitors, are screened for potential responsiveness to treatment based on their FLAP polymorphisms, or haplotypes (see also WO 99/052942, herein incorporated by reference).

Additionally, polymorphisms in any of the synthetic or signaling genes dedicated to the leukotriene pathway could result in a patient who is more responsive or less responsive to leukotriene modulator therapy (either FLAP or 5-LO inhibitor or leukotriene receptor antagonists). The genes dedicated to the leukotriene pathway are 5-lipoxygenase, 5-lipoxygenase-activating protein, $LTA_4$ hydrolase, $LTC_4$ synthase, $LTB_4$ receptor 1 ($BLT_1$), $LTB_4$ receptor 2 ($BLT_2$), cysteinyl leukotriene receptor 1 ($CysLT_1R$), cysteinyl leukotriene receptor 2 ($CysLT_2R$). For example, the 5-LO gene has been linked to aspirin intolerant asthma and airway hyperresponsiveness (Choi J H et al. *Hum Genet*. 114:337-344 (2004); Kim, S H et al. *Allergy* 60:760-765 (2005). Genetic variants in the promoter region of 5-LO have been shown to predict clinical responses to a 5-LO inhibitor in asthmatics (Drazen et al, *Nature Genetics*, 22, p 168-170, (1999). The $LTC_4$ synthase gene has been linked to atopy and asthma (Moissidis I et al. *Genet Med* 7:406-410 (2005). The $CysLT_2$ receptor has been linked to asthma and atopy (Thompson M D et al. *Pharmacogenetics* 13:641-649 (2003); Pillai S G et al. *Pharmacogenetics* 14:627-633 (2004); Park J S et al. *Pharmacogenet Genomics* 15:483-492 (2005); Fukai H et al. *Pharmacogenetics* 14:683-690 (2004). Any polymorphisms in any leukotriene pathway gene or combination of polymorphisms or haplotypes may result in altered sensitivity of the patient to therapy aimed at reducing the pathological effects of leukotrienes. In one embodiment, selection of patients who best respond to the leukotriene modulator therapies described herein is based, in part, on knowledge of polymorphisms in the leukotriene pathway genes and also knowledge of the expression of leukotriene-driven mediators. In one embodiment, patient selection is made on the basis of leukotriene pathway genotype alone, phenotype alone (biomarkers or functional markers) or any combination of genotype and phenotype.

A "haplotype," as described herein, refers to a combination of genetic markers ("alleles"). A haplotype can comprise one or more alleles (e.g., a haplotype containing a single SNP), two or more alleles, three or more alleles, four or more alleles, or five or more alleles. The genetic markers are particular "alleles" at "polymorphic sites" associated with FLAP. A nucleotide position at which more than one sequence is possible in a population is referred to herein as a "polymorphic site." Where a polymorphic site is a single nucleotide in length, the site is referred to as a single nucleotide polymorphism ("SNP"). For example, if at a particular chromosomal location, one member of a population has an adenine and another member of the population has a thymine at the same position, then this position is a polymorphic site, and, more specifically, the polymorphic site is a SNP. Polymorphic sites can allow for differences in sequences based on substitutions, insertions or deletions. Each version of the sequence with respect to the polymorphic site is referred to herein as an "allele" of the polymorphic site. Thus, in the previous example, the SNP allows for both an adenine allele and a thymine allele.

Typically, a reference sequence is referred to for a particular sequence. Alleles that differ from the reference are referred to as "variant" alleles. The term "variant FLAP" as used herein, refers to a sequence that differs from a reference FLAP sequence, but is otherwise substantially similar. The genetic markers that make up the haplotypes described herein are FLAP variants. In certain embodiments the FLAP variants are at least about 90% similar to a reference sequence. In other embodiments the FLAP variants are at least about 91% similar to a reference sequence. In other embodiments the FLAP variants are at least about 92% similar to a reference sequence. In other embodiments the FLAP variants are at least about 93% similar to a reference sequence. In other embodiments the FLAP variants are at least about 94% similar to a reference sequence. In other embodiments the FLAP variants are at least about 95% similar to a reference sequence. In other embodiments the FLAP variants are at least about 96% similar to a reference sequence. In other embodiments the FLAP variants are at least about 97% similar to a reference sequence. In other embodiments the FLAP variants are at least about 98% similar to a reference sequence. In other embodiments the FLAP variants are at least about 99% similar to a reference sequence.

Additionally, in certain embodiments the FLAP variants differ from the reference sequence by at least one base, while in other embodiments the FLAP variants differ from the reference sequence by at least two bases. In other embodiments the FLAP variants differ from the reference sequence by at least three bases, and in still other embodiments the FLAP variants differ from the reference sequence by at least four bases.

In one embodiment, additional variants include changes that affect a polypeptide, e.g., the FLAP polypeptide. The polypeptide encoded by a reference nucleotide sequence is the "reference" polypeptide with a particular reference amino acid sequence, and polypeptides encoded by variant alleles are referred to as "variant" polypeptides with variant amino acid sequences. In one embodiment, the FLAP nucleic acid sequence differences, when compared to a reference nucleotide sequence, includes the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence; duplication of all or a part of a sequence; transposition; or a rearrangement of a nucleotide sequence, as described in detail above. Such sequence changes alter the polypeptide encoded by a FLAP nucleic acid. For example, if the change in the nucleic acid sequence causes a frame shift, the frame shift can result in a change in the encoded amino acids, and/or can result in the generation of a premature stop codon, causing generation of a truncated polypeptide.

By way of example, a polymorphism associated with a susceptibility to myocardial infarction (MI), acute coronary syndrome (ACS), stroke or peripheral arterial occlusive disease (PAOD) is a synonymous change in one or more nucleotides (i.e., a change that does not result in a change in the amino acid sequence). Such a polymorphism, for example, alters splice sites, decrease or increase expression levels, affect the stability or transport of mRNA, or otherwise affect the transcription or translation of the polypeptide. The haplotypes described below are found more frequently in individuals with MI, ACS, stroke or PAOD than in individuals without MI, ACS, stroke or PAOD. Therefore, these haplotypes have predictive value for detecting a susceptibility to MI, ACS, stroke or PAOD in an individual.

Several variants of the FLAP gene have been reported to correlate with the incidence of myocardial infarction in patients (Hakonarson, *JAMA*, 293(18):2245-56, 2005), plus FLAP gene markers reportedly associated with the risk for developing asthma have been described in U.S. Pat. No. 6,531,279. Methods for identifying FLAP sequence variants are described, e.g., in U.S. Publication No. 2005/0113408, and in U.S. Pat. No. 6,531,279, incorporated herein by reference herein in their entirety.

In one embodiment, detecting haplotypes is accomplished by methods for detecting sequences at polymorphic sites, and therefore patients are selected using genotype selection of FLAP, 5-LO or other leukotriene pathway gene polymorphisms. In one embodiment, the presence or absence of a leukotriene pathway gene polymorphism or haplotype is determined by various methods, including, for example, using enzymatic amplification, restriction fragment length polymorphism analysis, nucleic acid sequencing, electrophoretic analysis of nucleic acid from the individual, or any combination thereof. In certain embodiments, determination of a SNP or haplotype identifies patients who will respond to, or gain benefit from, treatment with sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate. By way of example, methods of diagnosing a susceptibility to myocardial infarction or stroke in an individual, comprises determining the presence or absence of certain single nucleotide polymorphisms (SNPs) or of certain haplotypes, wherein the presence of the SNP or the haplotype is diagnostic of susceptibility to myocardial infarction or stroke.

Phenotype Analysis: Biomarkers

In one embodiment, patients who are under consideration for treatment with 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof, or drug combinations described herein that include 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof, are screened for potential responsiveness to treatment based on leukotriene-driven inflammatory biomarker phenotypes.

In one embodiment, patient screening based on leukotriene-driven inflammatory biomarker phenotypes is used as an alternative to, or it is complimentary with, patient screening by leukotriene pathway gene haplotype detection. The term "biomarker" as used herein refers to a characteristic which is measured and evaluated as an indicator of normal biological processes, pathological processes, or pharmacological responses to therapeutic intervention. Thus a biomarker is any substance, structure or process which is measured in the body, or its products, and which influences or predicts the incidence of outcome or disease. Biomarkers are classified into markers of exposure, effect, and susceptibility. Biomarkers are physiologic endpoints, by way of example blood pressure, or they are analytical endpoints, by way of example, blood glucose, or cholesterol concentrations. Techniques, used to monitor and/or measure biomarkers include, but are not limited to, NMR, LC-MS, LC-MS/MS, GC-MS, GC-MS/MS, HPLC-MS, HPLC-MS/MS, FT-MS, FT-MS/MS, ICP-MS, ICP-MS/MS, peptide/protein sequencing, nucleic acid sequencing, electrophoresis techniques, immuno-assays, immuno-blotting, in-situ hybridization, fluorescence in-situ hybridization, PCR, radio-immuno assays, and enzyme-immuno assays. Single nucleotide polymorphisms (SNPs) have also been useful for the identification of biomarkers for propensity to certain diseases and also susceptibility or responsiveness to drugs such as chemotherapeutic agents and antiviral agents. In one embodiment, these techniques, or any combination thereof, are used to screen patients for leukotriene-dependent or leukotriene mediated diseases or conditions, wherein such patients are beneficially treated with 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof, or drug combinations described herein that include 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid, including pharmaceutically acceptable salts, and pharmaceutically acceptable solvates thereof.

By way of example only, patients are selected for treatment with 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof, or drug combinations described herein that include 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof, by screening for enhanced inflammatory blood biomarkers such as, but not limited to, stimulated $LTB_4$, $LTC_4$, $LTE_4$, myeloperoxidase (MPO), eosinophil peroxidase (EPO), C-reactive protein (CRP), soluble intracellular adhesion molecule (sICAM), monocyte chemoattractant protein (MCP-1), monocyte inflammatory protein (MIP-1α), interleukin-6 (IL-6), the TH2 T cell activators interleukin 4 (IL-4), and 13 (IL-13) and other inflammatory cytokines. In certain embodiments, patients with inflammatory respiratory diseases, including but not limited to, asthma and COPD, are selected as those most likely to be responsive to leukotriene synthesis inhibition using 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof, by using a panel of leukotriene driven inflammatory biomarkers.

Phenotype Analysis: Functional Markers

In one embodiment, patients who are under consideration for treatment with 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof, or drug combinations described herein that include 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof, are screened for response to known modulators of the leukotriene pathway. In one embodiment, patient screening by evaluation of functional markers as indicators of a patient's response to known modulators of the leukotriene pathway are used as an alternative to, or it is complimentary with, patient screening by leukotriene pathway gene haplotype detection (genotype analysis) and/or monitoring/measurement of leukotriene-driven inflammatory biomarker phenotypes. Functional markers include, but are not limited to, any physical characteristics associated with a leukotriene dependent condition or disease, or knowledge of current or past drug treatment regimens.

By way of example only, the evaluation of lung volume and/or function are used as a functional marker for leukotriene-dependent or leukotriene mediated diseases or conditions, such as respiratory diseases. In one embodiment, lung function tests are used to screen patients, with such leukotriene-dependent or leukotriene mediated diseases or conditions, for treatment using 3-[5-(pyridin-2-ylmethoxy)-3-(2-methyl-2-propylthio)-1-[4-(2-methoxypyridin-5-yl)benzyl] indol-2-yl]-2,2-dimethyl-propionic acid, including pharmaceutically acceptable salts, and pharmaceutically acceptable solvates thereof, or pharmaceutical compositions or medicaments thereof. Such tests include, but are not limited to, evaluation of lung volumes and capacities, such as tidal volume, inspiratory reserve volume, expiratory reserve volume, residual volume, inspiratory capacity, functional residual capacity, vital capacity, total lung capacity, respiratory minute volume, alveolar ventilation, timed vital capacity, and ventilatory capacity. Method of measurement of lung volumes and capacities include, but are not limited to, maximum expiratory flow volume curve, forced expiratory volume in 1 sec. (FEV1), peak expiratory flow rate. In addition, other lung function tests used as functional markers for patient evaluation described herein include, but are not limited to, respiratory muscle power, maximum inspiratory pressure, maximum expiratory pressure, transdiaphragmatic pressure, distribution of ventilation, single breath nitrogen test, pulmonary nitrogen washout, and gas transfer.

Additionally, the knowledge of a patients past or current treatment regimen is used as a functional marker to assist in screening patients for treatment of leukotriene dependent conditions or diseases using 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof, or pharmaceutical compositions or medicaments thereof. By way of example only, such treatment regimens include past or current treatment using zileuton (Zyflo™), montelukast (Singulair™), pranlukast (Onon™), zafirlukast (Accolate™).

Also, in one embodiment, patients who are under consideration for treatment with 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof, or drug combinations described herein that include 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof, are screened for functional markers which include, but are not limited to, reduced eosinophil and/or basophil, and/or neutrophil, and/or monocyte and/or dendritic cell and/or lymphocyte recruitment, decreased mucosal secretion, decreased mucosal edema, and/or increased bronchodilation.

In certain embodiments, a patient sample is analyzed for leukotriene gene haplotypes, by way of example only, FLAP haplotypes, and the information obtained identifies a patient in need of treatment using various treatment methods. Such treatment methods include, but are not limited to, administering a therapeutic effective amount of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, including pharmaceutically acceptable salts, and pharmaceutically acceptable solvates thereof, or pharmaceutical composition or medicament thereof, alone or in combination with a therapeutic effective amount of a leukotriene receptor antagonist (by way of example, $CysLT_1$/$CysLT_2$ antagonist or $CysLT_1$ antagonist). In other embodiments a patient sample is analyzed for leukotriene gene haplotypes, by way of example only, FLAP haplotypes, and/or phenotype biomarkers, and/or phenotype functional marker responses to leukotriene modifying agents. In one embodiment, the patient is then treated using various treatment methods. Such treatment methods include, but are not limited to, administering a therapeutic effective amount of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid, including pharmaceutically acceptable salts, and pharmaceutically acceptable solvates thereof, or pharmaceutical composition or medicament thereof, alone or in combination with a therapeutic effective amount of a leukotriene receptor antagonist (by way of example, $CysLT_1$/$CysLT_2$ antagonist or $CysLT_1$ antagonist), or another anti-inflammatory agent. In still other embodiments a patient sample is analyzed for leukotriene gene haplotypes, by way of example only, FLAP haplotypes, and phenotype biomarkers, and phenotype functional marker responses to leukotriene modifying agents. In one embodiment, the patient is then treated using various treatment methods. Such treatment methods include, but are not limited to, administering a therapeutic effective amount of a FLAP inhibitor, or pharmaceutical composition or medicament which includes a FLAP inhibitor, administering a therapeutic effective amount of a FLAP inhibitor, or pharmaceutical composition or medicament which includes a FLAP inhibitor, in combination with a therapeutic effective amount of a leukotriene receptor antagonist (by way of example, $CysLT_1$/$CysLT_2$ antagonist or $CysLT_1$ antagonist), or administering a therapeutic effective amount of a FLAP inhibitor, or pharmaceutical composition or medicament which includes a FLAP inhibitor, in combination with a therapeutic effective amount of another anti-inflammatory agent.

Kits/Articles of Manufacture

For use in the therapeutic methods of use described herein, kits and articles of manufacture are also described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Packaging materials for use in packaging pharmaceutical products include, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by inhibition of FLAP, or in which FLAP is a mediator or contributor to the symptoms or cause.

For example, the container(s) include 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid, including pharmaceutically acceptable salts, and pharmaceutically acceptable solvates thereof, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

A kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contain one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

EXAMPLES

Abbreviations

| | |
|---|---|
| AUC | area under the curve |
| $CO_2$ | carbon dioxide |
| $Cs_2CO_3$ | cesium carbonate |
| DME | dimethoxyethane |
| DMF | dimethylformamide |
| DMSO | dimethylsulphoxide |
| DTT | dithiothreitol |
| $Et_3N$ | triethylamine |
| EDTA | ethylenediaminetetraacetic acid |
| eq | equivalent(s) |
| EtOAc | ethylacetate |
| EtOH | ethanol |
| HCl | hydrochloric acid |
| $H_2O$ | water |
| HPLC | high performance liquid chromatography |
| KOH | potassium hydroxide |
| LCMS | liquid chromatogrpahy mass spectrometry |
| MeOH | methanol |
| MTBE | methyl tert-butyl ether |
| $MgSO_4$ | magnesium sulfate |
| NaOH | sodium hydroxide |
| $NaNO_2$ | sodium nitrite |
| $Na_2S_2O_4$ | sodium hydrosulfite |
| $Na_2SO_4$ | sodium sulfate |
| $Na_2CO_3$ | sodium carbonate |
| NMR | nuclear magnetic resonance |
| ppm | parts per million |
| PD | pharmacodynamics |
| PK | pharmacokinetics |
| RH | Relative humidity |
| RRT | Relative retnetion time |
| SD | Standard deviation |
| THF | tetrahydrofuran |
| TLC | Thin layer chromatography |
| V/W | Volume/weight |

The following examples are illustrative and non-limiting to the scope of the compounds, compositions, formulations and methods described herein.

In one aspect, 3-[5-(pyrid-2-ylmethoxy)-3-(2-methyl-2-propylthio)-1-[4-(2-methoxypyrid-5-yl)benzyl]indol-2-yl]-2,2-dimethylpropionic acid was prepared as provided in US 2007/0105866 (see Example 1, Compound 2-19). In another aspect, 3-[5-(pyrid-2-ylmethoxy)-3-(2-methyl-2-propylthio)-1-[4-(2-methoxypyrid-5-yl)benzyl]indol-2-yl]-2,2-dimethylpropionic acid was prepared as described herein.

Example 1

Synthesis of 3-[5-(pyridin-2ylmethoxy)-3-(2-methyl-2-propylthio)-1-[4[(2-methoxypyridin-5-yl)benzyl]-indol-2-yl-2,2-dimethyl-propionic acid, and sodium salt thereof

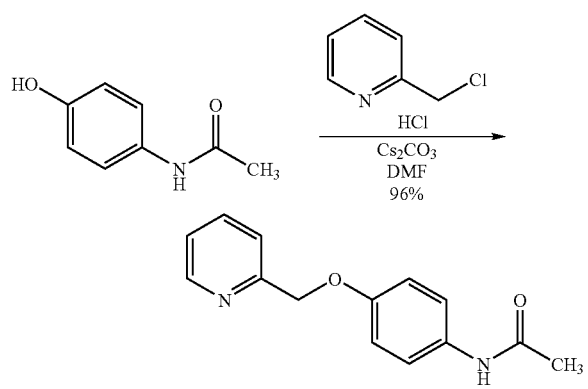

Step 1: N-[4-(Pyridin-2-ylmethoxy)-phenyl]-acetamide

A mixture of 4-acetamidophenol (Sigma-Aldrich; 73.6 g), 2-chloromethylpyridine hydrochloride (80 g) and cesium carbonate (320 g) in DMF (1 L) was stirred at 70° C. for 2 days. The mixture was cooled, poured into water (2 L) and extracted with EtOAC (×6). The organic layers were washed with brine, dried (MgSO$_4$) and filtered to give a tan solid (114 g) which was used as such in the next step.

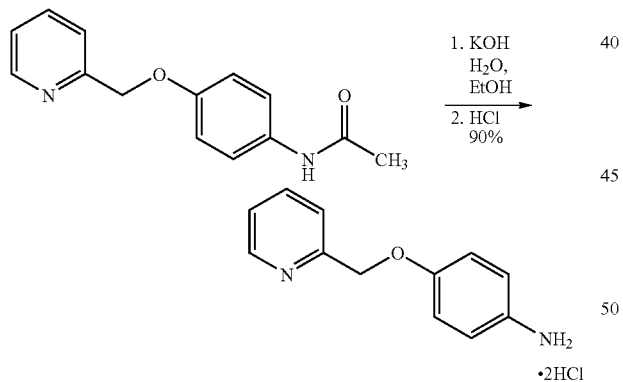

Step 2: 4-(Pyridin-2-ylmethoxy)-phenylamine hydrochloride

N-[4-(Pyridin-2-ylmethoxy)-phenyl]-acetamide (114 g) was dissolved in EtOH (1 L) and to this was added KOH (50 g) in water (200 mL). The solution was heated to 110° C. for 2 days, KOH (20 g in 100 mL water) was added and heating continued for a further 2 days. The solution was cooled, the EtOH was removed in vacuo and the residue partitioned between EtOAc and water. After extraction of the water with EtOAc (3×), the organic layers were washed with brine, dried (MgSO$_4$) and filtered. To this solution was added HCl in EtOAc and a precipitated formed immediately. Collection of the solids by filtration followed by drying under vacuum provided the title compound (95 g) as a pink solid.

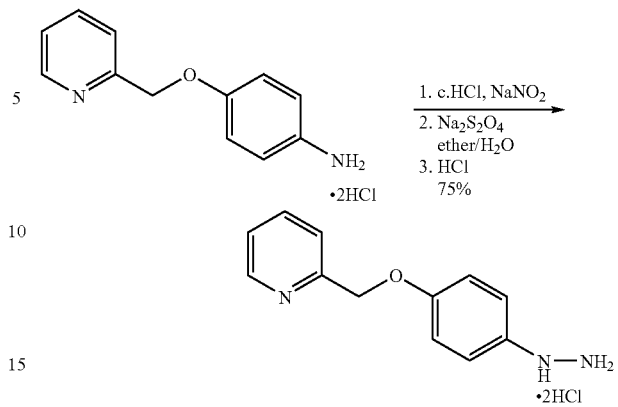

Step 3: [4-(Pyridin-2-ylmethoxy)-phenyl]-hydrazine dihydrochloride 4-(Pyridin-2-ylmethoxy)-phenylamine hydrochloride (95 g) was dissolved in water (1 L) at 0° C. and to this was added NaNO$_2$ (26 g) in water (100 mL). The diazonium salt was allowed to form over 45 minutes and then it was poured slowly over 15 minutes into a rapidly stirred mixture of Na$_2$S$_2$O$_4$ (350 g) in water (1 L) and ether (1 L) at 0° C. Stirring continued for 40 minutes then mixture was made basic using conc. KOH. After extraction using EtOAc (×2) the organic layers were washed with water, then brine, dried (MgSO$_4$) and filtered. To this solution was added saturated HCl in EtOAc and a precipitated formed immediately. Collection of the solids by filtration followed by drying under vacuum provided the title compound as a tan solid (75 g).

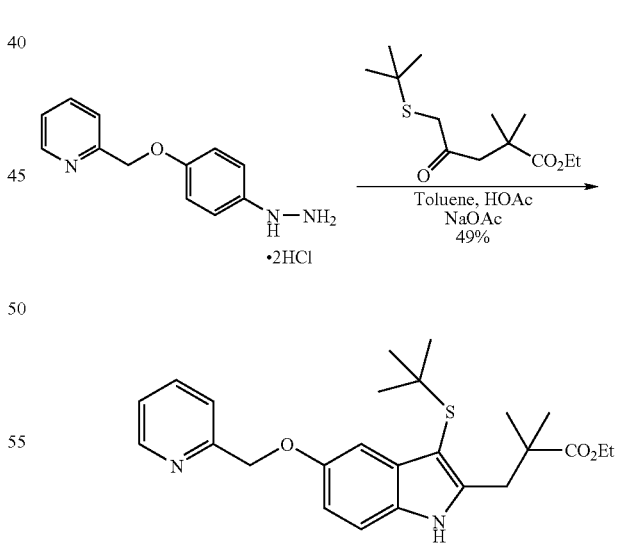

Step 4: 3-[5-(pyrid-2-ylmethoxy)-3-(2-methyl-2-propylthio)-1H-indol-2-yl]-2,2-dimethylpropionoic acid ethyl ester

[4-(Pyridin-2-ylmethoxy)-phenyl]-hydrazine dihydrochloride (75 g), 5-tert-butylsulfanyl-2,2-dimethyl-4-oxo-pentanoic acid ethyl ester (64 g), NaOAc (40 g) in toluene (800 mL) and HOAc (400 mL) was stirred at room temperature for 3 days. In one aspect, 5-tert-butylsulfanyl-2,2-dimethyl-4-oxo-pentanoic acid ethyl ester was prepared according to the procedures described in U.S. Pat. No. 5,288,743 issued Feb. 22, 1994. In another aspect, 5-tert-butylsulfanyl-2,2-dimethyl-4-oxo-pentanoic acid ethyl ester was prepared as outlined herein. The mixture was poured into water and made basic with solid $Na_2CO_3$. The mixture was extracted with EtOAc (×3), then washed with water (×2), brine, dried ($MgSO_4$), filtered and concentrated to give a dark red-black oil. Column chromatography of the mother liquor (silica gel packed in hexanes; eluting with hexane then hexane-EtOAc 9:1 rising to 4:1) afforded 68 g of the title compound, as a yellow solid.

mmol) in DMF dropwise. The reaction was then stirred at about −10° C. for about 1 hour and allowed to warm to room temperature slowly. After 16 hours, LCMS confirmed the formation of the product. The reaction was quenched with saturated $NH_4Cl$ and diluted with methyl tert-butyl ether (MTBE) and water. The aqueous phase was extracted twice with MTBE. The combined organic layers were dried over $MgSO_4$, filtered, and concentrated, and the crude product was purified by column chromatography to give the tittle compound.

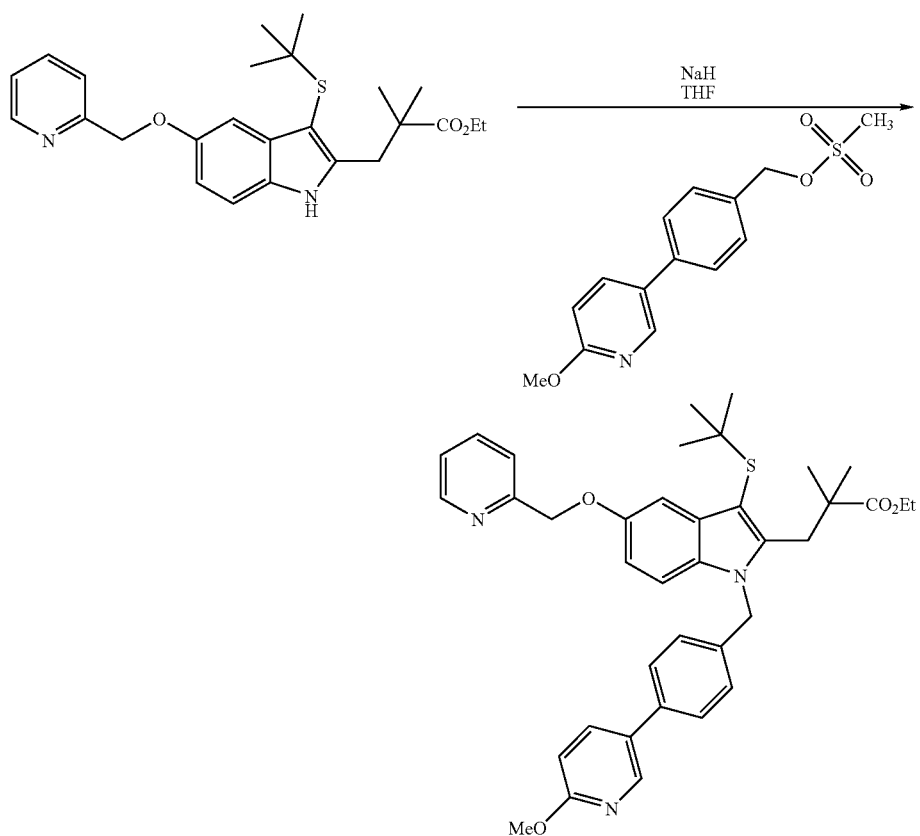

Step 5: 3-[5-(Pyrid-2-ylmethoxy)-3-(2-methyl-2-propylthio)-1-[4-(2-methoxypyrid-5-yl)benzyl]indol-2-yl]-2,2-dimethylpropionic acid ethyl ester 3-[5-(Pyrid-2-ylmethoxy)-3-(2-methyl-2-propylthio)-1-[4-(2-methoxypyrid-5-yl)benzyl]indol-2-yl]-2,2-dimethylpropionic acid ethyl ester (20.0 g, 45.4 mmol) was dissolved in DMF (150 mL) and cooled to −10° C. under $N_2$. Sodium hydride (60% dispersion in mineral oil; 2.0 g, 50.0 mmol) was added portionwise, and the reaction was stirred at −10° C. for 45 minutes until the foam had disappeared. To this dark brown-reddish solution was added methanesulfonic acid 4-(6-methoxy-pyridin-3-yl)-benzyl ester (Int-72; 16.0 g, 54.5

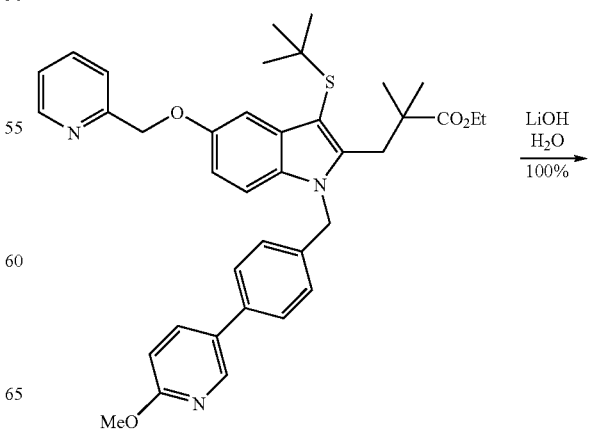

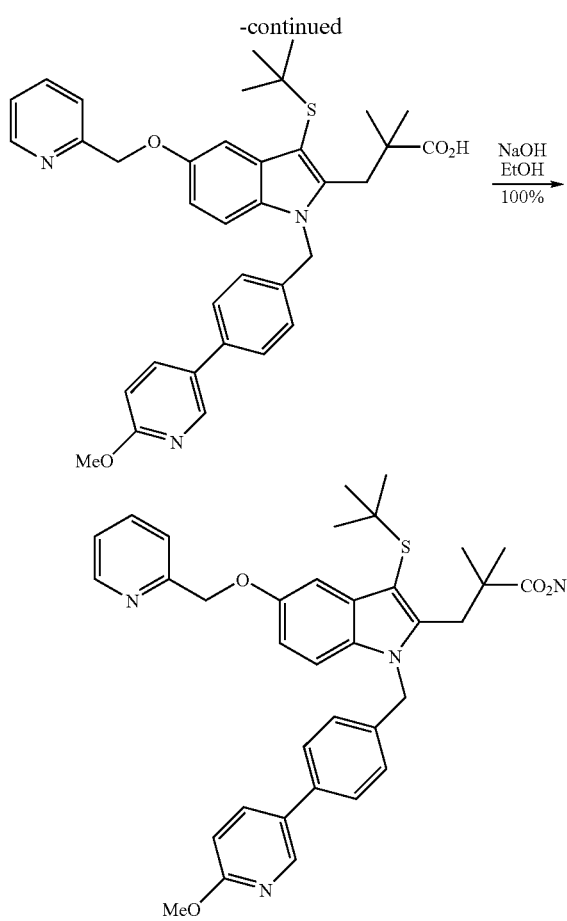

Step 6: 3-[5-(Pyrid-2-ylmethoxy)-3-(2-methyl-2-propylthio)-1-[4-(2-methoxypyrid-5-yl)benzyl]indol-2-yl]-2,2-dimethylpropionic acid 3-[5-(Pyrid-2-ylmethoxy)-3-(2-methyl-2-propylthio)-1-[4-(2-methoxypyrid-5-yl)benzyl]indol-2-yl]-2,2-dimethylpropionic acid ethyl ester (21.5 g, 33.7 mmol) was dissolved in THF (100 mL) and MeOH (100 mL) and stirred until it became a clear solution. 3N LiOH aqueous solution (56 mL, 168.5 mmol) was added and the reaction was refluxed at 80° C. for 2 hours. LCMS confirmed the formation of the product, so the reaction was cooled to room temperature and partitioned between EtOAc and water. The pH of the aqueous solution was adjusted to pH 1 with 10% HCl, and the aqueous phase was extracted three times with EtOAc. The combined organic layers were washed with water, dried over MgSO$_4$, filtered, and concentrated to 3-[5-(pyrid-2-ylmethoxy)-3-(2-methyl-2-propylthio)-1-[4-(2-methoxypyrid-5-yl)benzyl]indol-2-yl]-2,2-dimethylpropionic acid.

3-[5-(Pyrid-2-ylmethoxy)-3-(2-methyl-2-propylthio)-1-[4-(2-methoxypyrid-5-yl)benzyl]indol-2-yl]-2,2-dimethylpropionic acid (14.2 g) was dissolved in ethanol (233 ml) and 1N NaOH in water (23.75 ml) was added. After removal of the solvent, 15.7 g of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate was obtained.

In one aspect, sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate was crystallized as follows: Ethanol (32 ml) was added to 15.7 g of 3-[5-(pyrid-2-ylmethoxy)-3-(2-methyl-2-propylthio)-1-[4-(2-methoxypyrid-5-yl)benzyl]indol-2-yl]-2,2-dimethylpropionic acid, dissolving at about 36° C. Methyl tert-butyl ether (76 ml) was added slowly at about 36° C. The solution was stirred for about 15 minutes at 36° C. until the formation of solid material. To this was added methyl tert-butyl ether (100 ml) and after 20 minutes the solution was cooled to 0° C. After about 1 hour at 0° C., the solid material was filtered and washed with methyl tert-butyl ether and dried under vacuum for about 15 hours to provide 13.4 g of crystalline sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate.

Example 2

Synthesis of 5-tert-Butylsulfanyl-2,2-dimethyl-4-oxo-pentanoic acid ethyl ester

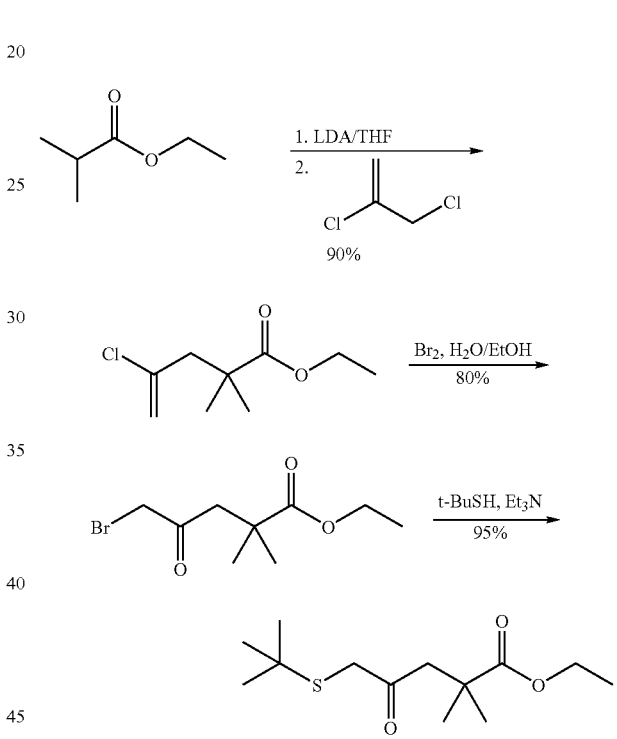

Step 1: Synthesis of 4-chloro-2,2-dimethyl-pent-4-enoic acid ethyl ester

Diisopropylamine (1.25 eq) was added to a reaction flask containing THF (tetrahydrofuran; 10.0-fold, V/W of ethyl isobutyrate) under N$_2$. The mixture was cooled to less than −70° C., and n-butyllithium (2.7M; 1.14 eq) was added to the reaction mixture while the temperature was maintained at less than −65° C. The reaction mixture was slowly warmed to room temperature and then stirred for 2 hours under N$_2$. The reaction mixture was then cooled to less than −70° C., and ethyl isobutyrate (1.0 eq) was added, followed by 2,3-dichloro-1-propene (1.09 eq), while the temperature was maintained at less than −70° C. The reaction was allowed to warm to room temperature and stirred overnight under N$_2$. The reaction was then quenched with ice water (10.0-fold, V/W of starting material), and the pH adjusted to pH 7 with aqueous 6M HCl. The organic layer was separated, washed twice with brine, and dried over Na$_2$SO$_4$. The solvent was removed in vacuo and the product was taken on to the next step without further purification.

Step 2: Synthesis of 5-Bromo-2,2-dimethyl-4-oxo-pentanoic acid ethyl ester

4-Chloro-2,2-dimethyl-pent-4-enoic acid ethyl ester (1.0 eq) was added to a reaction flask containing EtOH (ethanol; 4.4-fold, V/W of starting material) and water (3.2-fold, V/W of starting material) under N₂. The reaction mixture was cooled to less than 0° C., and bromine (1.02 eq) was added to the reaction mixture while the temperature was maintained at less than 0° C. After agitating for 2 hours, the reaction was checked for completion by NMR. Since no starting material was seen by NMR analysis, the reaction was diluted with cold water (10.0-fold, V/W of starting material) and stirred for 5-10 minutes. The organic layer (on the bottom) was separated, with the aqueous layer was extracted with CH₂Cl₂ until no product was seen in the aqueous layer. The combined organic layers were then washed with aqueous 5% Na₂CO₃ (6-fold, V/W of starting material) and brine (3.0-fold, V/W of starting material). The organic layer was dried over Na₂SO₄ and concentrated in vacuo to give the desired product.

Step 3: Synthesis of 5-tert-Butylsulfanyl-2,2-dimethyl-4-oxo-pentanoic acid ethyl ester To a reaction flask containing THF (5.0-fold, V/W of starting material) was added 5-bromo-2,2-dimethyl-4-oxo-pentanoic acid ethyl ester (1.0 eq) under N₂. The mixture was cooled to a temperature of −5-0° C., and a solution of 2-methyl-2-propanethiol (1.2 eq) and triethylamine (1.25 eq) was added while maintaining the temperature below 0° C. The reaction was stirred at room temperature for 25 hours, and then hexane (3.0-fold, V/W of starting material) was slowly added. After agitating for 30 minutes, the solid material was removed by filtration and washed with 50% EtOAc/hexane solution. The filtrate was concentrated under reduced pressure to give the desired product, which was taken on to the next step without further purification.

Example 3

Synthesis of Ethyl 3-(3-(tert-butylthio)-5-hydroxy-1-(4-(4,4,5,5-tetramethyl-1,3,2-dioxaborolan-2-yl) benzyl)-1H-indol-2-yl)-2,2-dimethylpropionate

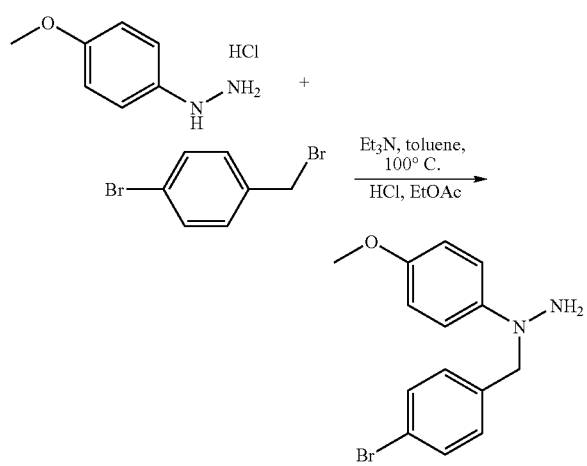

Step 1: Synthesis of N-(4-Bromo-benzyl)-N-(4-methoxy-phenyl)-hydrazine hydrochloride:

4-Methoxyphenyl hydrazine hydrochloride (1.0 eq) was added to a reaction flask containing of toluene (16 eq.; V/W of starting material) under nitrogen. To this reaction flask was added 4-bromo-benzylbromide (1.05 eq) and Et₃N (2.1 eq). The reaction mixture was heated to about 100-105° C. and stirred for about 3 hours after which the reaction flask was cooled to room temperature. Ethyl acetate (10.0-fold, V/W of starting material) was added to the reaction flask and agitated for about 1.5 hours. The reaction mixture was filtered to collect the solid which was subsequently washed with toluene and dried in vacuo. Ethyl acetate was then added and the solution was agitated. The pH of the mixture was adjusted to a pH of 2 with saturated HCl/Ethyl acetate solution and further agitated for 1 hour. The solid was then collected and washed with ethyl acetate and then air dried. The product was taken on to the next step without further purification.

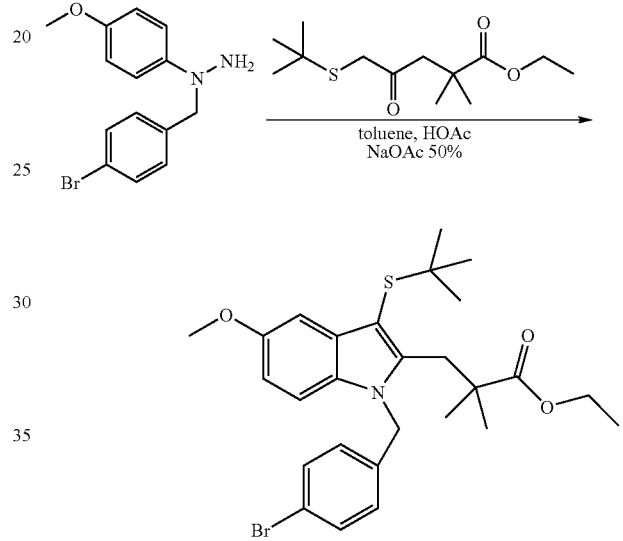

Step 2: Synthesis of 3-[1-(4-Bromo-benzyl)-3-tert-butylsulfanyl-5-methoxy-1H-indol-2-yl]-2,2-dimethyl-propionic acid ethyl ester:

N-(4-Bromo-benzyl)-N-(4-methoxy-phenyl)-hydrazine hydrochloride (1.0 eq) was added to a reaction flask containing toluene (10.0-fold, V/W of starting material). To this reaction mixture was added acetic acid (5.0-fold, V/W of starting material), followed by 5-tert-butylsulfanyl-2,2-dimethyl-4-oxo-pentanoic acid ethyl ester (1.05 eq) and NaOAc (2.3 eq). The reaction mixture was agitated at room temperature for about 4 days after which cold water (15.0-fold, V/W of starting material) was added to the reaction and stirred for about 30 minutes. The organic layer was collected and the aqueous layer washed with toluene to recover additional product. The organic portions were collected and washed with water and saturated brine solution. The organic layer was subsequently dried over Na₂SO₄ and concentrated under reduced pressure. A slurry of collected compound was made with methanol (5.0-fold, V/W of starting material) at 0-5° C. for about 4 hours. The solid was collected and washed with cold methanol. Any remaining solvent was removed by drying under reduced pressure.

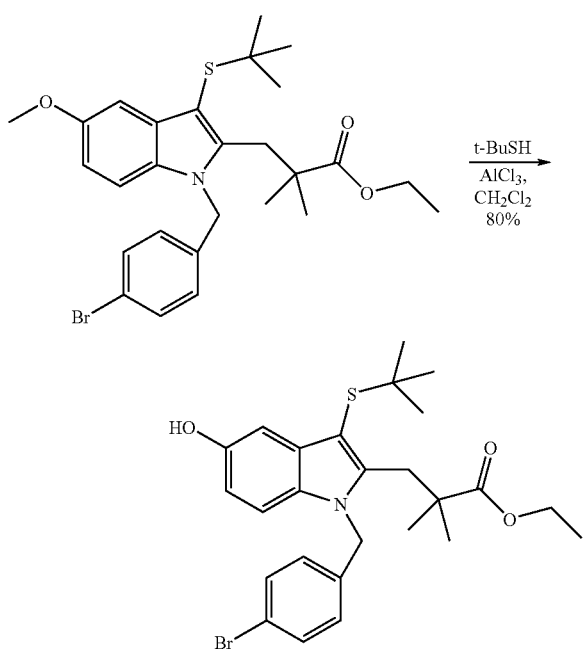

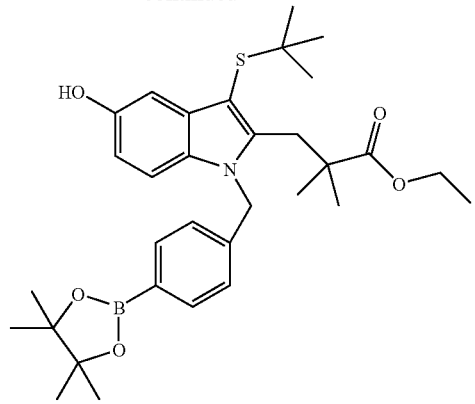

Step 4: Synthesis of Ethyl 3-(3-(tert-butylthio)-5-hydroxy-1-(4-(4,4,5,5-tetramethyl-1,3,2-dioxaborolan-2-yl)benzyl)-1H-indol-2-yl)-2,2-dimethylpropionate:

To a reaction vessel was charged DMF (9.0-fold V/W to starting material). The solvent was bubbled with nitrogen while agitating for 60 minutes. 3-[1-(4-Bromo-benzyl)-3-tert-butylsulfanyl-5-hydroxy-1H-indol-2-yl]-2,2-dimethyl-propionic acid ethyl ester (1500 g; 1 eq.) and bis(pinacolato)diboron (810 g; 1.1 eq.) were then added followed by potassium acetate (836 g, 2.94 eq.). The reaction mixture is bubbled with nitrogen while agitating for 20 minutes. Under nitrogen, Pd(dppf)Cl$_2$ (88 g; 0.0372 eq.) was added. The reaction mixture was again bubbled with nitrogen while agitating for 15 minutes. The reaction mixture was heated to about 75-85° C. under nitrogen. The reaction was agitated at about 80-85° C. for about 2 hours and then monitored by TLC (petroleum ethers/ethyl acetate=5/1) for completion under nitrogen. The reaction was cooled to room temperature (about 20-25° C.). The reaction vessel is charged with water (12.0-fold V/W of starting material). The reaction mixture is extracted with MTBE three times (about 50 L). The combined organic layer was filtered through a celite pad to remove any solids. The combined organic layers were washed with 10.0-fold of water twice and then 6.0-fold of brine. The filtrate was dried over Na$_2$SO$_4$ and the concentrated to give a dark oil.

Step 3: Synthesis of 3-[1-(4-Bromo-benzyl)-3-tert-butylsulfanyl-5-hydroxy-1H-indol-2-yl]-2,2-dimethyl-propionic acid ethyl ester:

To a reaction vessel containing CH$_2$Cl$_2$ (3.3-fold, V/W of starting material) was added 3-[1-(4-bromo-benzyl)-3-tert-butylsulfanyl-5-methoxy-1H-indol-2-yl]-2,2-dimethyl-propionic acid ethyl ester (1.0 eq). 2-Methyl-2-propanethiol (7.80 eq) was subsequently added to the reaction mixture and the reaction was cooled down to a temperature of −5 to 0° C. While maintaining the reaction mixture at this temperature, AlCl$_3$ (3.30 eq) was added portion-wise to the reaction. The reaction was stirred at a temperature of 0 to 5° C. for about 2 hours, then subsequently warmed to 20-25° C. The reaction was then quenched with water (6.5 fold; v/w of starting material) and the mixture acidified to a pH of 2 with 2.0M HCl. The organic layer was then collected and the aqueous layer washed with CH$_2$Cl$_2$ to recover remaining product. The organic layers were combined and washed with 1.0M HCl and water followed by a brine wash and concentrated in vacuo. Ethyl acetate (1.0 fold; v/w of starting material) was added to the solid and heated to dissolve the product. The flask was gradually cooled to 0-2° C. followed by the slow addition of hexanes. The mixture was agitated for a period of about 2 hours, followed by filtration to collect the solid. The solid was subsequently dried under vacuum.

Example 4

Synthesis of 3-[5-hydroxy-3-(2-methyl-2-propylthio)-1-[4[(2-methoxypyridin-5-yl)benzyl]-indol-2-yl-2,2-dimethyl-propionic acid ethyl ester (R=—CH$_2$CH$_3$; X=Br)

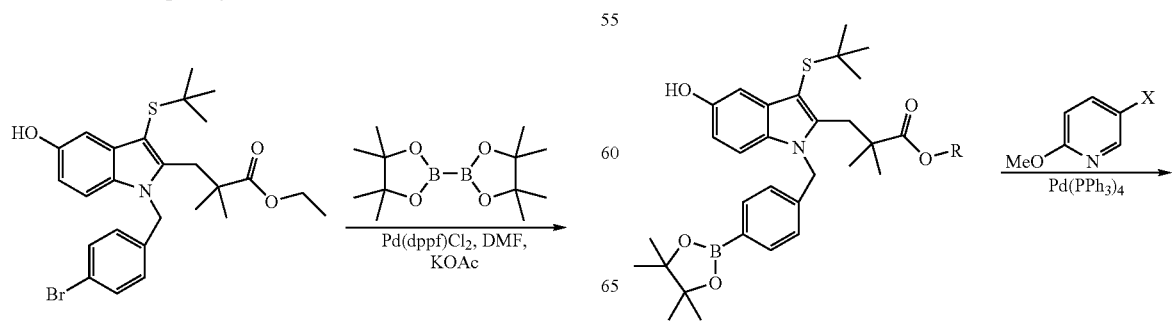

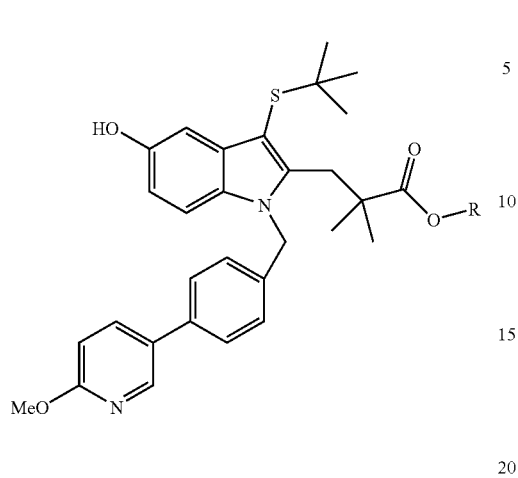

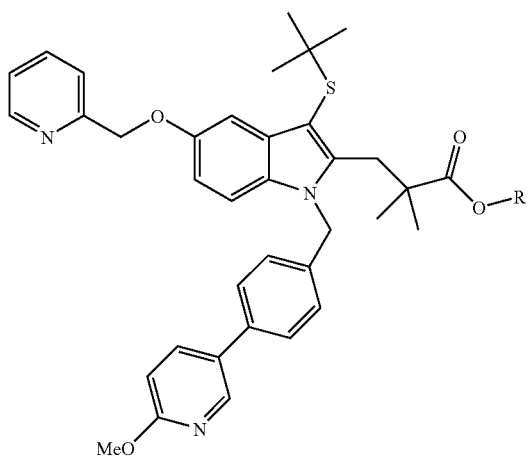

Ethyl 3-(3-(tert-butylthio)-5-hydroxy-1-(4-(4,4,5,5-tetramethyl-1,3,2-dioxaborolan-2-yl)benzyl)-1H-indol-2-yl)-2,2-dimethylpropionate (675 g, 1.2 mol), 5-bromo-2-methoxypyridine (280.5 g, 1.5 mol), Pd(PPh$_3$)$_4$ (23.63 g, 0.02 mol), and K$_2$CO$_3$ (412 g) were added to a reactor containing 6.75 L of DME and 3.38 L of water and stirred. Nitrogen gas was bubbled into the mixture for about 20 minutes. The mixture was then heated to between 80 to 85° C. and stirred overnight. TLC analysis (EtOAc/Petroleum ether=1/5) showed the reaction had reached completion. The mixture was subsequently cooled to ambient temperature. Following cooling, the compound was extracted three times with EtOAc. The organic layer was then washed with water, followed by a brine wash. The organic layer was then dried with sodium sulfate, the solid removed by filtration and the organic layer was then concentrated in vacuo, affording 653 g of product in near quantitative yield.

3-[5-Hydroxy-3-(2-methyl-2-propylthio)-1-[4[(2-methoxypyridin-5-yl)benzyl]-indol-2-yl-2,2-dimethyl-propionic acid ethyl ester (525 g, 0.96 mol) was added to a reactor containing 10.5 L of CH$_3$CN and stirred. 2-chloromethylpyridine HCl salt (204 g, 1.25 mol), and Cs$_2$CO$_3$ (840 g, 2.55 mol) were added and the mixture was heated to between 70 to 75° C. and stirred overnight. TLC analysis (EtOAc/Petroleum ether, 1:5) show the reaction had reached completion. Following cooling to ambient temperature, the solid was filtered off. The filtrate was concentrated and washed with water. The compound was extracted two times with EtOAc. The organic layer was then washed with water, followed by a brine wash. The organic layer was then dried with sodium sulfate, the solid removed by filtration and the organic layer was then concentrated in vacuo. The compound was loaded on a silica gel column (5 kg), and eluted with EtOAc/Petroleum ether (1/5) affording 540 g of the desired product in 88% yield.

Example 5

Synthesis of 3-[5-(Pyrid-2-ylmethoxy)-3-(2-methyl-2-propylthio)-1-[4-(2-methoxypyrid-5-yl)benzyl]indol-2-yl]-2,2-dimethylpropionic acid ethyl ester (R═—CH$_2$CH$_3$; X'═Cl)

Example 6

Synthesis of 3-[5-(Pyrid-2-ylmethoxy)-3-(2-methyl-2-propylthio)-1-[4-(2-methoxypyrid-5-yl)benzyl]indol-2-yl]-2,2-dimethylpropionic acid

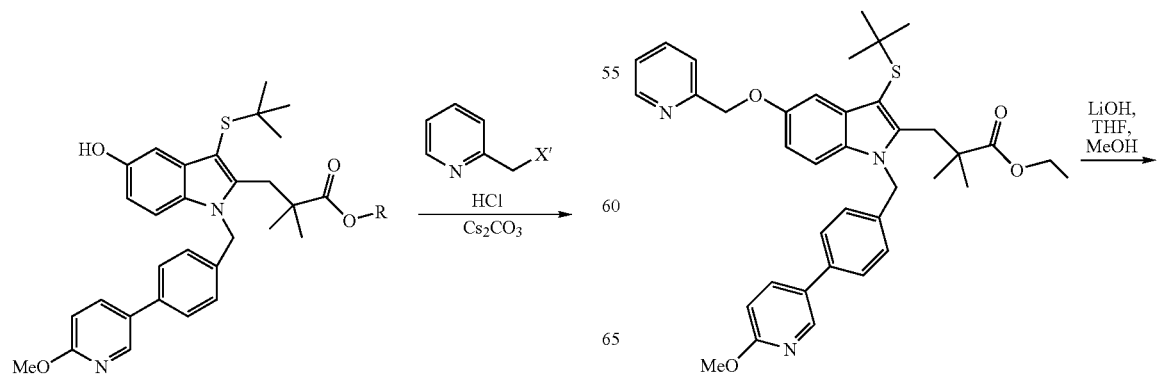

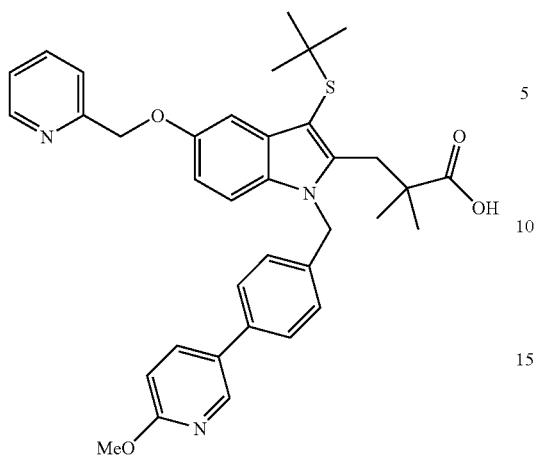

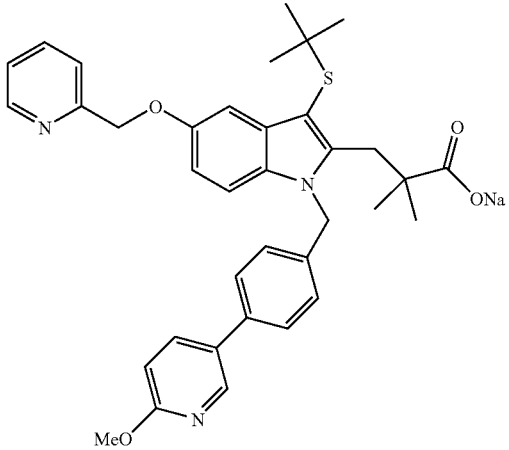

3-[5-(Pyrid-2-ylmethoxy)-3-(2-methyl-2-propylthio)-1-[4-(2-methoxypyrid-5-yl)benzyl]indol-2-yl]-2,2-dimethyl-propionic acid ethyl ester (693 g, 1.086 mol) was added to a reactor containing 6.91 L of THF/MeOH/water in a 2:1:1 ratio and stirred. LiOH.H$_2$O (54.75 g, 1.3 mol) was added to the reactor and the mixture was heated to between 50 to 60° C. and stirred overnight (about 12 hours). TLC analysis (EtOAc/Petroleum ether, 1/5) showed the reaction had reached completion. The THF/MeOH/water solvent mixture was removed in vacuo and about 6 liters of water was added. The organic impurities were removed with extraction using EtOAc in 1.5 liter batches. The pH of the aqueous layer was adjusted to a pH of between 2 and 3 using 3N HCl. The compound was extracted twice with dichloromethane in 6 liter batches. Following a water wash and a brine wash, the organic layer was dried over Na$_2$SO$_4$. The solid was filtered and the organic layer was concentrated in vacuo to afford 623 g of desired product in 94% yield.

Example 7

Synthesis of Sodium 3-[5-(Pyrid-2-ylmethoxy)-3-(2-methyl-2-propylthio)-1-[4-(2-methoxypyrid-5-yl)benzyl]indol-2-yl]-2,2-dimethylpropanate

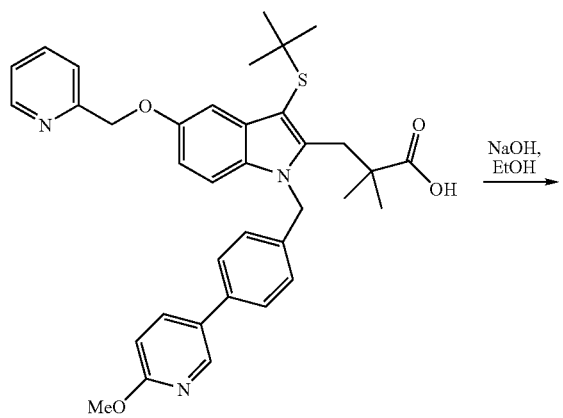

3-[5-(Pyrid-2-ylmethoxy)-3-(2-methyl-2-propylthio)-1-[4-(2-methoxypyrid-5-yl)benzyl]indol-2-yl]-2,2-dimethyl-propionic acid (444 g, 0.498 mol) was added to a reactor containing 2.1 L of EtOH and stirred. A NaOH solution (29 g in 218 mL of water) was added to the reactor and stirred at ambient temperature for about 30 mins. The reaction was concentrated under vacuum at a temperature of between 40 and 50° C. under a reduced pressure of between 10 to 30 mm Hg. The compound was subsequently dried under vacuum at a temperature of between 40 and 45° C. under a reduced pressure of between 5 and 10 mm Hg to afford 460 g of desired product in near quantitative yield.

Example 8

Kilo-Lab Synthesis of Sodium 3-[5-(Pyrid-2-yl-methoxy)-3-(2-methyl-2-propylthio)-1-[4-(2-methoxypyrid-5-yl)benzyl]indol-2-yl]-2,2-dimethylpropionate The cGMP starting material used for the process was ethyl 3-(3-(tert-butylthio)-5-hydroxy-1-(4-(4,4,5,5-tetramethyl-1,3,2-dioxaborolan-2-yl)benzyl)-1H-indol-2-yl)-2,2-dimethylpropionate from Example 3. Ethyl 3-(3-(tert-butylthio)-5-hydroxy-1-(4-(4,4,5,5-tetramethyl-1,3,2-dioxaborolan-2-yl)benzyl)-1H-indol-2-yl)-2,2-dimethylpropionate from Example 3, was scaled up to 2.0 kg. In order to ensure optimal Suzuki coupling conditions, the amount of time needed to deoxygenate the mixture was increased from about 5-10 minutes to about 30-45 minutes. Workup and isolation of the product proceeded as described above to yield 1.49 kg of 3-[5-hydroxy-3-(2-methyl-2-propylthio)-1-[4-(2-methoxypyrid-5-yl)benzyl]indol-2-yl]-2,2-dimethylpropionic acid ethyl ester in about 86% yield.

To address possible residual palladium concerns, two 20 g parallel runs (lot A and lot B) were implemented to control the amount of palladium exiting the synthesis in order to meet the ICH guidelines of <20 ppm palladium. Following workup of the reaction as described in Example 4, lot A solution in ethyl acetate was treated with Darco KB while lot B was not. Lot A had amounts of palladium in a lower range, while lot B was above 600 ppm. In one instance, Lot A had palladium in the 40 ppm range after treatment with Darco KB.

Coupling of 3-[5-hydroxy-3-(2-methyl-2-propylthio)-1-[4-(2-methoxypyrid-5-yl)benzyl]indol-2-yl]-2,2-dimethyl-propionic acid ethyl ester with chloromethylpyridine as exemplified in Example 5 gave 941 g of 3-[5-(pyrid-2-ylmethoxy)-3-(2-methyl-2-propylthio)-1-[4-(2-methoxypyrid-5-yl)benzyl]indol-2-yl]-2,2-dimethylpropionic acid ethyl ester in about 54% yield. Trituration of 3-[5-(Pyrid-2-ylmethoxy)-3-(2-methyl-2-propylthio)-1-[4-(2-methoxypyrid-5-yl)benzyl]indol-2-yl]-2,2-dimethylpropionic acid ethyl ester in a MeOH/Heptane mixture removed some dark colored impurities as observed by visualization and by thin layer chromatography.

Saponification of 3-[5-(pyrid-2-ylmethoxy)-3-(2-methyl-2-propylthio)-1-[4-(2-methoxypyrid-5-yl)benzyl]indol-2-yl]-2,2-dimethylpropionic acid ethyl ester with LiOH as described in Example 6 (at about 53° C. for about 18 hours) did not reach completion. An additional 5 mol % LiOH monohydrate was used to drive the reaction to completion. Following removal of the organic solvent, and adjustment of the pH in a range from about pH 2 to about pH 3, the product precipitated from the aqueous environment and was isolated by filtration. Sodium salt formation using NaOH proceeded as described in Example 7 to yield 1.05 kg of a tan oil with an estimated 10% residual ethanol. The palladium levels in this sample were above 20 ppm. A simple recrystallization from ethyl acetate did not reduce the amount of palladium in the sample.

Sodium 3-[5-(Pyrid-2-ylmethoxy)-3-(2-methyl-2-propylthio)-1-[4-(2-methoxypyrid-5-yl)benzyl]indol-2-yl]-2,2-dimethylpropionate (1.05 kg) was dissolved in about 10.4 L of ethanol and treated with 1.0 kg of Darco KB-G for at least 12 hours. The mixture was filtered and rinsed with 5 liters of ethanol. After concentration, the amount of palladium in the sample was below 20 ppm. In one instance, the amount of palladium in the sample was less than 10 ppm. In one instance, the amount of palladium was about 7.5 ppm.

Purification of sodium 3-[5-(Pyrid-2-ylmethoxy)-3-(2-methyl-2-propylthio)-1-[4-(2-methoxypyrid-5-yl)benzyl]indol-2-yl]-2,2-dimethylpropionate proceeded by trituration in hot ethyl acetate. The amount of residual ethanol plays a key role in how well the material crystallizes from ethyl acetate, with less residual ethanol aiding the process. Upon cooling, filtering and drying, sodium 3-[5-(Pyrid-2-ylmethoxy)-3-(2-methyl-2-propylthio)-1-[4-(2-methoxypyrid-5-yl)benzyl]indol-2-yl]-2,2-dimethylpropionate was obtained.

Example 9

Lithium 3-[5-(pyrid-2-ylmethoxy)-3-(2-methyl-2-propylthio)-1-[4-(2-methoxypyrid-5-yl)benzyl]indol-2-yl]-2,2-dimethylpropionate 3-[5-(Pyrid-2-ylmethoxy)-3-(2-methyl-2-propylthio)-1-[4-(2-methoxypyrid-5-yl)benzyl]indol-2-yl]-2,2-dimethylpropionic acid (1 eq.) is added to a reactor containing ethanol and stirred. A LiOH solution in water (1.05 eq.) is added to the reactor and stirred at ambient temperature. After removal of the solvent, lithium 3-[5-(pyrid-2-ylmethoxy)-3-(2-methyl-2-propylthio)-1-[4-(2-methoxypyrid-5-yl)benzyl]indol-2-yl]-2,2-dimethylpropionate is obtained.

Example 10

Potassium 3-[5-(pyrid-2-ylmethoxy)-3-(2-methyl-2-propylthio)-1-[4-(2-methoxypyrid-5-yl)benzyl]indol-2-yl]-2,2-dimethylpropionate 3-[5-(Pyrid-2-ylmethoxy)-3-(2-methyl-2-propylthio)-1-[4-(2-methoxypyrid-5-yl)benzyl]indol-2-yl]-2,2-dimethylpropionic acid (1 eq.) is added to a reactor containing ethanol and stirred. A KOH solution in water (1.05 eq.) is added to the reactor and stirred at ambient temperature. After removal of the solvent, potassium 3-[5-(pyrid-2-ylmethoxy)-3-(2-methyl-2-propylthio)-1-[4-(2-methoxypyrid-5-yl)benzyl]indol-2-yl]-2,2-dimethylpropionate is obtained.

Example 11

Crystalline 3-[5-(Pyrid-2-ylmethoxy)-3-(2-methyl-2-propylthio)-1-[4-(2-methoxypyrid-5-yl)benzyl]indol-2-yl]-2,2-dimethylpropionic acid 3-[5-(Pyrid-2-ylmethoxy)-3-(2-methyl-2-propylthio)-1-[4-(2-methoxypyrid-5-yl)benzyl]indol-2-yl]-2,2-dimethylpropionic acid (610 mg) was dissolved in 3 mL ethanol and the compound then allowed to slowly crystallize. Removal of the solvent gave a white crystalline powder.

Example 12

Amorphous 3-[5-(Pyrid-2-ylmethoxy)-3-(2-methyl-2-propylthio)-1-[4-(2-methoxypyrid-5-yl)benzyl]indol-2-yl]-2,2-dimethylpropionic acid In one aspect, amorphous compound is prepared by suspending or dissolving the free acid in a mixture of water and if necessary a small amount of a suitable organic solvent or co-solvents, such as methanol, ethanol, isopropanol, acetonitrile, and the like. The aqueous solvent is removed by lyophilization (freeze-drying) to leave the compound as an amorphous powder.

Example 13

Amorphous sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate 3-[5-(Pyrid-2-ylmethoxy)-3-(2-methyl-2-propylthio)-1-[4-(2-methoxypyrid-5-yl)benzyl]indol-2-yl]-2,2-dimethylpropionic acid (444 g, 0.729 mol) was added to a reactor containing 2.1 L of EtOH and stirred. A NaOH solution (29 g in 218 mL of water; 1.00 equivalents) was added to the reactor and stirred at ambient temperature for about 30 minutes. The reaction was concentrated under vacuum at a temperature of about 40 to about 50° C. under a reduced pressure of about 10 mm Hg to about 30 mm Hg. The compound was subsequently dried under vacuum at a temperature of between 40 and 45° C. under a reduced pressure of between 5 and 10 mm Hg to afford 460 g of desired product in near quantitative yield. The sodium salt had a detectable amount of palladium less than about 10 ppm.

Example 14

Crystalline sodium 3-[5-(Pyrid-2-ylmethoxy)-3-(2-methyl-2-propylthio)-1-[4-(2-methoxypyrid-5-yl)benzyl]indol-2-yl]-2,2-dimethylpropionate Sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate from Example 3 was heated in EtOAc to obtain dissolution and a white precipitate formed upon cooling. The amount of residual ethanol plays a key role in how well the material crystallizes from EtOAc with less residual ethanol aiding the process. The amount of residual ethanol plays a role in providing a certain polymorph of the compound. If too much ethanol is present in the recrystallization, Form B is obtained. If no or very little ethanol is present during the recrystallization, then Form C is obtained.

Polymorphs of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate Two polymorphs of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate (Form B and Form C) and an amorphous phase (Phase A) have been identified. Form B and Form C were obtained by crystallization from ethyl acetate.

Phase A is amorphous.

Form B is crystalline (irregular plates) and solvated. In one embodiment Form B is solvated with ethanol and water. Form B is physically and chemically stable. A variety of organic solvents lead to the "solvated" polymorph (Form B). The solvent becomes an integral part of the crystal lattice whereas water is adsorbed onto the surface. In one aspect, Form B is solvated with ethanol. Form B loses its crystallinity and the colour changes to yellow after 1 week storage at 40° C. & 75% RH.

Form C is crystalline (irregular plates) and desolvated. Form C is physically and chemically stable at 5° C., 25° C./60% RH and 40° C./75% RH for at least two months. No change is seen in the x-ray powder diffraction pattern of Form C before and after one week at 40° C. and 75% relative humidity.

Any water in the crystal form is surface water and is not an integral part of either polymorph, although small amounts of water may be present in the crystal lattice.

The melting range of crystalline sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate is 286° C. to 290° C. (Forms B and Form C, respectively).

Example 15

X-Ray Powder Diffraction XRPD Pattern Determination of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate X-Ray powder diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. The beam divergence, i.e., the effective size of the X-ray beam on a sample of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate was approximately 4 mm. A θ-θ continuous scan mode was employed with a sample-detector distance of 20 cm which gives an effective 2θ range of 3.2°-29.7°. Typically the sample would be exposed to the X-ray beam for 120 seconds.

Samples run under ambient conditions were prepared as flat plate specimens using powder as received without grinding. Approximately 1-2 mg of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate was lightly pressed on a glass slide to obtain a flat surface.

Samples run under non-ambient conditions were mounted on a silicon wafer with heat-conduction compound. The sample was then heated to the appropriate temperature at about 20° C. min$^{-1}$ and subsequently held isothermally for about 1 minute before data collection was initiated.

The X-Ray powder diffraction pattern for Form B is displayed in FIG. 2 and characteristic peaks are tabulated in Table 1.

TABLE 1

| XRPD pattern peak data for Form B: | |
|---|---|
| Peak Position (deg 2Θ) | Relative Intensity |
| 7.2 | 61 |
| 9.1 | 100 |
| 13.8 | 17 |
| 14.6 | 14 |
| 15.2 | 27 |
| 16.5 | 17 |
| 17.1 | 18 |
| 18.2 | 52 |
| 18.9 | 42 |
| 20.9 | 57 |
| 22.3 | 55 |
| 25.4 | 21 |
| 26.9 | 25 |
| 27.9 | 31 |
| 28.6 | 20 |
| 29.4 | 15 |
| 31.8 | 19 |

The X-Ray powder diffraction pattern for Form C is displayed in FIG. 1 and characteristic peaks are tabulated in Table 2.

TABLE 2

| XRPD pattern peak data for Form C: | |
|---|---|
| Peak Position (deg 2Θ) | Relative Intensity |
| 3.8 | 40 |
| 7.6 | 21 |
| 8.4 | 14 |
| 10.6 | 12 |
| 11.4 | 17 |
| 12.0 | 39 |
| 13.7 | 9 |
| 14.7 | 10 |
| 15.7 | 26 |
| 16.7 | 35 |
| 17.4 | 58 |
| 18.2 | 40 |
| 19.0 | 39 |
| 19.8 | 34 |
| 20.5 | 100 |
| 23.2 | 50 |
| 24.2 | 24 |
| 25.6 | 29 |
| 27.0 | 17 |
| 29.0 | 20 |
| 30.8 | 20 |
| 31.6 | 13 |
| 32.8 | 19 |
| 34.4 | 20 |
| 36.4 | 17 |

The values displayed in Table 1 and Table 2 may vary slightly depending on sample preparation and the instrument used.

Example 16

Aqueous Solubility

The aqueous solubility of Form B, Form C and a crystalline sample of 3-[5-(pyrid-2-ylmethoxy)-3-(2-methyl-2-propylthio)-1-[4-(2-methoxypyrid-5-yl)benzyl]indol-2-yl]-2,2-dimethylpropionic acid was determined as follows:

Aqueous solubility was determined by suspending sufficient compound in 0.25 mL of water to give a maximum final concentration of ≥10 mg·mL$^{-1}$ of the 3-[5-(pyridin-2yl-methoxy)-3-(2-methyl-2-propylthio)-1-[4[(2-methoxypyridin-5-yl)benzyl]indol-2-yl-2,2-dimethyl-propionic acid. The suspension was equilibrated at 25° C. for 24 hours then the pH was measured. The suspension was then filtered through a glass fibre C filter into a 96 well plate. The filtrate was then diluted by a factor of 101. Quantitation was by HPLC with reference to a standard solution of approximately 0.1 mg·mL$^{-1}$ in DMSO. Different volumes of the standard, diluted and undiluted sample solutions were injected. The solubility was calculated using the peak areas determined by integration of the peak found at the same retention time as the principal peak in the standard injection.

TABLE 3

HPLC protocol used to determine aqueous solubility:

| | |
|---|---|
| Type of method | Reverse phase with gradient elution |
| Column | Phenomenex Luna, C18 (2) 5 µm 50 × 4.6 mm |
| Column Temperature (° C.) | 25 |
| Injection (µl) | 5, 8 and 50 |
| Detection Wavelength, Bandwidth (nm) | 260.80 |
| Flow Rate (ml.min$^{-1}$) | 2 |
| Phase A: | 0.1% TFA in water |
| Phase B: | 0.085% TFA in acetonitrile |

| | Time (min) | % Phase A | % Phase B |
|---|---|---|---|
| Timetable: | 0.0 | 95 | 5 |
| | 1.0 | 80 | 20 |
| | 2.3 | 5 | 95 |
| | 3.3 | 5 | 95 |
| | 3.5 | 95 | 5 |
| | 4.4 | 95 | 5 |

The results of the determination of the thermodynamic solubility of the three samples are shown in Table 4.

TABLE 4

Results of aqueous solubility determination

| Sample | Crystalline Free Acid | Sodium Salt Form B | Sodium Salt Form C |
|---|---|---|---|
| Appearance of mixture after equilibration for 24 hours | Suspension | Fine Suspension | Fine Suspension |
| pH of saturated solution | 7.88 | 9.95 | 10.05 |
| Concentration of filtrate (as mg/ml of free base) | 0.0019 | 5.4 | >10 |

Form C of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate is more soluble than Form B and the crystalline free acid.

The solubility of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate was examined at various pH levels at about 25° C. The solubility profile is displayed in Table 5 for Form B.

TABLE 5 pH Solubility Profile at Room Temperature

| pH | Concentration (mg/mL) |
|---|---|
| about 1.1 | about 0.690 |
| about 4.9 | about 0.0594 |
| about 8.8 | about 0.00573 |
| about 9.2 | about 9.80 |
| about 9.8 | about 53.1 |
| about 10.4 | >70 |

The solubility of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate is pH dependent. The aqueous solubility is <5 µg/mL at about pH 7. The solubility increases in basic media (>70 mg/mL at pH 10).

Example 17

Solubility in Organic Solvents

The solubility of Form C of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate was also examined in a variety of common organic solvents. The solubility data in a variety of organic solvents is displayed in Table 6.

TABLE 6

Solubility Profile of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate in Common Organic Solvents

| Solvent | Solubility, mg/mL at 25° C. |
|---|---|
| Isopropanol | 1.1 |
| Acetonitrile | 0.2 |
| Ethanol | 17.1 |
| Propylene glycol | 13.43 |
| 0.5% Methylcellulose/water | 9.3 |
| Methanol | >50 |

Sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate is very soluble in methanol and sparingly soluble in acetonitrile and isopropanol.

Example 18

Batch Analysis of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate Batch analysis data are presented in Table X for Form B, Form C and Phase A.

TABLE 7

Summary of Analytical Data for sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate:

| | Sample No. | | |
|---|---|---|---|
| | 1 | 2 | 3 |
| Batch Size (g) | 670 | 460 | 142 |
| Appearance | White powder | Off-white powder | White powder |
| Identity | Corresponds to standard | Corresponds to standard | Corresponds to standard |
| X-Ray Diffraction Pattern | Consistent with Form B | Consistent with Phase A | Consistent with Form C |
| Heavy Metals (in ppm) | NA | NA | <20 |
| Water Content (in %) | 1.68 | 2.52 | 0.12 |
| Residual Solvents (%) | Total: 4.45% >1% EtOH | Total: 3.05% 1.15% EtOH | Total: <0.30% 0.275% EtOAc <0.026% THF |
| Purity by HPLC (in %) | 97.4[a] | 97.7[a] | 96.9[a] |
| Assay by HPLC (in %) | 91.1[b] | 98.5[b] | 97.7[b] |
| Sodium content (wt %) by ICP-AES | 3.99 | 3.3 | 3.5 |
| Pd content by ICP-AES | 5 ppm Pd | 5 ppm Pd | 8.7 ppm Pd |
| DSC (onset ° C.) | NA | NA | 293 |

[a]Purity was determined by HPLC-area normalization.
[b]Assay was determined by HPLC weight % "as is" (no correction for presence of water or solvents)
NA = not analyzed ambient temperature to 350° C. A nitrogen purge at 60 ml·min$^{-1}$ was maintained over the sample.

A summary table of the data is given in Table 8.

For crystalline 3-[5-(pyrid-2-ylmethoxy)-3-(2-methyl-2-propylthio)-1-[4-(2-methoxypyrid-5-yl)benzyl]indol-2-yl]-2,2-dimethylpropionoic acid, a small weight loss is seen at low temperature in the TGA, likely to be residual water (as seen in the Karl Fischer results). A large endothermic melt is seen at 206° C., which is accompanied by a 2.2% weight loss. The sample begins to decompose at 268° C., shown by the thermal events and the step in the baseline of the DSC and the beginning of a large weight loss in the TGA.

The thermal behavior of Form B is much more complex with the TGA and DSC traces showing multiple events. The first endotherm seen in the DSC matches with the 6% weight loss in the TGA and is likely to be due to the loss of adsorbed water on the surface of the amorphous sample. An endotherm begins at 193° C., after which the sample re-crystallizes to a solid which melts at 283° C. and then completely decomposes.

Form C shows an initial weight loss of 2.5%, which occurs at the same temperature as the first endotherm in the DSC. This is likely to be caused by the loss of residual water from the sample. A second endotherm is seen at 115° C., associated with a 0.7% weight loss. A broad endotherm is seen at 285° C., at the same temperature as a 1.6% weight loss. The width of the endotherm, the weight loss and the change in baseline of the DSC trace show that this event is the melting and decomposition of the sample. Gross decomposition occurs after 300° C., as shown by the large weight loss in the TGA plot.

TABLE 8

Summary of data from thermal experiments:

| Sample | | Thermic event | Onset Temperature (° C.) | Enthalpy (J/g) | Weight loss (%) |
|---|---|---|---|---|---|
| Crystalline 3-[5-(pyrid-2-ylmethoxy)-3-(2-methyl-2-propylthio)-1-[4-(2-methoxypyrid-5-yl)benzyl]indol-2-yl]-2,2-dimethylpropionoic acid | 1 | None | 25 | — | 0.2 |
| | 2 | Endotherm | 206 | 78.1 | 2.2 |
| | 3 | Decomposition | 268 | — | |
| Form B | 1 | Endotherm | 31 | 99.7 | 6.0 |
| | 2 | Endotherm | 116 | 1.1 | 0.5 |
| | 3 | Endotherm | 154 | 6.1 | 0.8 |
| | 4 | Enodtherm | 193 | — | |
| Form C | 1 | Endotherm | 31 | 28.2 | 2.5 |
| | 2 | Endotherm | 115 | 11.6 | 0.7 |
| | 3 | Endotherm | 285 | 70.0 | 1.6 |
| | 4 | Decomposition | 300 | — | |

Example 19 and 20

Differential Scanning Calorimetry (DSC) and Thermo-Gravimetric Analysis (TGA)

DSC data were collected on a TA Instruments Q1000 equipped with a 50 position auto-sampler. The instrument was calibrated for energy and temperature calibration using certified indium. Typically a 1 mg sample of sample, in a pin-holed aluminum pan, was heated at 10° C. min$^{-1}$ from 25° C. to 320° C. A nitrogen purge at 30 ml·min$^{-1}$ was maintained over the sample.

TGA data were collected on a TA Instruments Q500 TGA, equipped with a 16 position auto-sampler. The instrument was temperature calibrated using certified Alumel. Typically a 5 mg sample was loaded onto a pre-tared platinum crucible and aluminum DSC pan, and was heated at 10° C. min$^{-1}$ from Example 21

Polarized Light Microscopy (PLM) Study of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate Samples of crystalline 3-[5-(pyrid-2-ylmethoxy)-3-(2-methyl-2-propylthio)-1-[4-(2-methoxypyrid-5-yl)benzyl]indol-2-yl]-2,2-dimethylpropionoic acid, partially crystalline sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate and crystalline sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate were studied on a Leica LM/DM polarized light microscope with a digital video camera for image capture. A small amount of each sample was placed on a glass slide, mounted in immersion oil and covered with a glass slip, the individual particles being separated as well as possible. The sample was viewed with appropriate magnification and partially polarized light, coupled to a λ false-color filter. The free acid is made up of a mixture of laths and irregular particles.

The size distributions for both the sodium salts (Form B and Form C) was similar and ranged from about <5 μm to about 220 μm. Crystalline 3-[5-(pyrid-2-ylmethoxy)-3-(2-methyl-2-propylthio)-1-[4-(2-methoxypyrid-5-yl)benzyl]indol-2-yl]-2,2-dimethylpropionoic acid had a much wider size distribution with particles ranging from about <5 μm to about 500 μm.

Example 22

Hot Stage Microscopy (HSM) Study

Hot Stage Microscopy was carried out using a Leica LM/DM polarized light microscope combined with a Mettler-Toledo MTFP82HT hot-stage and a digital video camera for image capture. A small amount of sample material was placed onto a glass slide with individual particles separated as well as possible. The sample was viewed with appropriate magnification and partially polarized light, coupled to a λ false-color filter, whilst being heated from ambient temperature typically at 10-20° C. min$^{-1}$.

Microscopic examination of the samples whilst being heated from ambient temperature to 310° C. at 10° C. min$^{-1}$ was recorded as a video. Samples were not dispersed in oil for these experiments.

A sample of crystalline 3-[5-(pyrid-2-ylmethoxy)-3-(2-methyl-2-propylthio)-1-[4-(2-methoxypyrid-5-yl)benzyl]indol-2-yl]-2,2-dimethylpropionoic acid showed no change from room temperature until 198° C., when the particles started to soften. At 208° C. most of the particles are starting to melt and the melting of the sample is complete by 210° C. No further changes are seen until the droplets start to darken at 280° C., indicating that gross decomposition is occurring. After being cooled to room temperature the sample was composed of black oily droplets.

A sample of crystalline sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate showed no changes from room temperature until 292° C. While not being bound by theory, this means that the first two endotherms are not due to the loss of a bound solvent or a phase change that is visible. Therefore the first endotherm is likely to be the loss of the residual water, which fits with the 2.2% weight loss seen in the TGA. At 292° C. the sample is beginning to melt and by 297° C. the whole sample is molten. However the sample has darkened, indicating that some decomposition has occurred. This means that the sample melts and immediately starts to decompose, which agrees with the DSC data. Some recrystallization is seen at 302° C. and by 309° C. gross decomposition has occurred and the sample has blackened. After being cooled to room temperature the sample was composed of black oily droplets.

Example 23

Gravimetric Vapor Sorption (GVS)

Sorption isotherms were obtained using a Hiden IGASorp moisture sorption analyzer, controlled by CFRSorp software. The sample temperature was maintained at 25° C. by a Huber re-circulating water bath. The humidity was controlled by mixing streams of dry and wet nitrogen, with a total flow rate of 250 ml·min$^{-1}$. The relative humidity was measured by a calibrated Vaisala RH probe (dynamic range of 0-95% RH), located near the sample. The weight change, (mass relaxation) of the sample as a function of % RH was constantly monitored by the microbalance (accuracy±0.001 mg).

Typically 10-20 mg of a sample was placed in a tared mesh stainless steel basket under ambient conditions. The sample was loaded and unloaded at 40% RH and 25° C. (typical room conditions).

A moisture sorption isotherm was performed as outlined below (2 scans giving 1 complete cycle). The standard isotherm was performed at 25° C. at 10% RH intervals over a 0-90% RH range.

| Parameters | Values |
|---|---|
| Adsorption - Scan 1 | 40-90 |
| Desorption/Adsorption - Scan 2 | 85-Dry, Dry-40 |
| Intervals (% RH) | 10 |
| Number of Scans | 2 |
| Flow rate (ml.min$^{-1}$) | 250 |
| Temperature (° C.) | 25 |
| Stability (° C. · min$^{-1}$) | 0.05 |
| Minimum Sorption Time (hours) | 1 |
| Maximum Sorption Time (hours) | 4 |
| Mode | AF2 |
| Accuracy (%) | 98 |

The software uses a least squares minimization procedure together with a model of the mass relaxation, to predict an asymptotic value. The measured mass relaxation value must be within 5% of that predicted by the software, before the next % RH value is selected. The minimum equilibration time was set to 1 hour and the maximum to 4 hours.

The sample was recovered after completion of the isotherm and re-analyzed by XRPD.

Crystalline 3-[5-(pyrid-2-ylmethoxy)-3-(2-methyl-2-propylthio)-1-[4-(2-methoxypyrid-5-yl)benzyl]indol-2-yl]-2,2-dimethylpropionoic acid is not hygroscopic but it does adsorb and desorb a small amount of water reversibly. Examination of the sample by XRPD after the GVS experiment shows that no overall change in form has occurred during the GVS experiment and the free acid is stable to changes in humidity.

TABLE 9a

Summary of weight changes for crystalline 3-[5-(pyridin-2-ylmethoxy)-3-(2-methyl-2-propylthio)-1-[4-(2-methoxypyrid-5-yl)benzyl]indol-2-yl]-2,2-dimethylpropionoic acid during GVS experiment:

| Cycle | Scan | Sorption | % RH change | % weight change |
|---|---|---|---|---|
| 1 | 1 | Adsorption | load to 40 | 0.00 |
|   | 2 | Adsorption | 40 to 90 | 0.34 |
|   |   | Desorption | 90 to 0 | −0.42 |
|   |   | Adsorption | 0 to 40 | 0.07 |
| 2 | 3 | Adsorption | 40 to 90 | 0.29 |
|   | 4 | Desorption | 90 to 0 | −0.40 |
|   |   | Adsorption | 0 to 40 | 0.08 |

Form B is very hygroscopic with a total weight change of 26% between 0% RH and 90% RH. The majority of this weight change occurs between 65% RH and 90% RH. At lower humidities a 6% weight change is seen, which matches with the weight loss seen in the TGA trace. A kinetics plot shows that the sample does not reach equilibrium at many of the data points so there may still be some more water to be adsorbed or desorbed. When the sample was removed from the GVS experiment it had changed from a clean white powder to a yellow solid. This solid was examined by XRPD. No overall change in form is observed, implying that the sample is stable to changes in humidity. However the discoloration shows that there has been some change in the sample and so it was analyzed by HPLC for purity. The purity results show that the sample has not changed chemically during either the GVS experiment or the stability testing. Therefore this sample is stable to changes in humidity at 25° C. during the GVS experiment.

TABLE 9b

Summary of weight changes for Form B during GVS experiment:

| Cycle | Scan | Sorption | % RH change | % weight change |
|---|---|---|---|---|
| 1 | 1 | Adsorption | load to 40 | −1.54 |
|   | 2 | Adsorption | 40 to 90 | 20.92 |
|   |   | Desorption | 90 to 0 | −25.51 |
|   |   | Adsorption | 0 to 40 | 3.73 |
| 2 | 3 | Adsorption | 40 to 90 | 20.72 |
|   | 4 | Desorption | 90 to 0 | −24.45 |
|   |   | Adsorption | 0 to 40 | 3.66 |

Form C is also hygroscopic, although the total weight change of 16% is not as large as Form B. This sample reversibly adsorbs and desorbs water with little hysteresis and the majority of the weight change occurs between 75% RH and 90% RH. XRPD analysis after the experiment shows that there has been no overall change in form in this sample. Additionally the sample shows no color change during the GVS experiment. Therefore this sample is hygroscopic but is stable to changes in humidity.

TABLE 9c

Summary of weight changes for Form C during GVS experiment:

| Cycle | Scan | Sorption | % RH change | % weight change |
|---|---|---|---|---|
| 1 | 1 | Adsorption | load to 40 | −0.37 |
|   | 2 | Adsorption | 40 to 90 | 13.83 |
|   |   | Desorption | 90 to 0 | −16.23 |
|   |   | Adsorption | 0 to 40 | 1.98 |
| 2 | 3 | Adsorption | 40 to 90 | 14.52 |
|   | 4 | Desorption | 90 to 0 | −16.51 |
|   |   | Adsorption | 0 to 40 | 2.01 |

Example 24

Water Determination by Karl Fischer

The water content of each sample was measured on a Mettler Toledo DL39 Coulometer using Hydranal Coulomat AG reagent and an argon purge. Weighed solid samples were introduced into the vessel on a platinum TGA pan which was connected to a subaseal to avoid water ingress. Approx 10 mg of sample was used per titration and duplicate determinations were made.

The Karl Fischer results are summarized in Table 10 and show that both the sodium salts have a large amount of water associated with them.

TABLE 10

Summary of Karl Fischer results:

| Sample | KF results | Average KF result |
|---|---|---|
| Crystalline Free Acid | 0.07%, 0.13% | 0.1% water |
| Form B | 7.09%, 7.42% | 7.3% water |
| Form C | 3.75%, 3.65% | 3.7% water |

Example 25

Purity Analysis

Purity analysis was performed on an Agilent HP1100 series system equipped with a diode array detector and using ChemStation software v9.

| Type of method | Normal Phase | Reverse Phase | x |
|---|---|---|---|
|  | Isocratic | Gradient | x |
| Column: | Phenomenex Luna C18 (2), | | |
|  | 150 × 4.6 mm, 5 µm | | |
| Column Temperature (° C.): | 25 | | |
| Injection (µl): | 5 | | |
| Detection: | | | |
| Wavelength, Bandwidth (nm): | 255.90 | | |
| Flow Rate (ml · min − 1): | 1 | | |
| Phase A: | 0.1% TFA in water | | |
| Phase B: | 0.085% TFA in acetonitrile | | |
|  | Time (min) | % Phase A | % Phase B |
| Timetable: | 0 | 95 | 5 |
|  | 25 | 5 | 95 |
|  | 25.2 | 95 | 5 |
|  | 30 | 95 | 5 |

The results of the determination of the purity by HPLC of the three samples are shown below in Table 11.

TABLE 11

HPLC Purity Results of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate:

|  | Form B Na salt | Form C Na salt | Crystalline free acid free acid |
|---|---|---|---|
| Parent purity % | 89.4 | 96.4 | 97.2 |
| Sum impurities >=0.1% | 9.81 | 3.12 | 2.41 |
| Sum impurities <0.1% | 0.78 | 0.48 | 0.35 |
| RRT | Area % | Area % | Area % |
| 0.81 | 0.59 | 0.43 | 0.13 |
| 0.84 | 7.43 | 1.97 | 1.27 |
| 0.86 | 0.22 | 0.10 | 0.13 |
| 0.99 | 0.62 | 0.14 | 0.11 |
| 1.00 | 89.41 | 96.39 | 97.24 |
| 1.02 | 0.10 | 0.06 | 0.09 |
| 1.03 | 0.11 | 0.10 | 0.11 |
| 1.04 | 0.26 | 0.15 | 0.29 |
| 1.05 | 0.19 | 0.11 | 0.06 |
| 1.13 | 0.04 | 0.04 | 0.26 |
| 1.17 | 0.28 | 0.12 | 0.10 |

Example 26

FLAP Binding Assays

A non-limiting example of a FLAP binding assay is as follows:

Packed human polymorphonuclear cell pellets ($1.8 \times 10^9$ cells) (Biological Speciality Corporation) were resuspended, lysed and 100,000 g membranes prepared as described (Charleson et al. *Mol. Pharmacol*, 41, 873-879, 1992). 100,000×g pelleted membranes were resuspended in Tris assay buffer (50 mM Tris HCl pH 7.4, 1 mM EDTA, 1 mM DTT, 30% glycerol,) to yield a protein concentration of 1-5 mg/mL. 10 µL (2.5 µg) membrane suspension was added to 96 well deepwell plate, 78 µL Tris-Tween buffer, 10 µL $^3$H 3-[5-(pyrid-2-ylmethoxy)-3-tert-butylthio-1-benzyl-indol-2-yl]-2,2-dimethylpropionic acid to ~30,000 cpm, 2.5 µL inhibitor and incubated for 60 minutes at room temperature. 100 µL ice-cold washed buffer was added to the incubation mixture. Plates were then filtered and washed 3× with 200 µL ice cold Tris-Tween buffer, scintillation bottoms sealed, 50 µL scintillant added, shaken for 30 minutes then counted in a TopCount. Specific binding was determined as defined as total radioactive binding minus non-specific binding in the presence of 10 µM MK886. $IC_{50}$ values were determined using Graphpad prism analysis of drug titration curves.

Example 27

Human Blood LTB$_4$ Inhibition Assay

A non-limiting example of a human blood LTB$_4$ inhibition assay is as follows:
Blood was drawn from consenting human volunteers into heparinized tubes and 150 µL aliquots added to wells containing 1.5 µL 100% DMSO (vehicle) or 1.5 µL drug in 100% DMSO. Samples were incubated for 15 minutes at 37° C. 2 µL calcium ionophore A23817 (from a 50 mM DMSO stock diluted just prior to the assay in Hanks balanced salt solution (Invitrogen)) to 1.5 mM) was added, solutions mixed and incubated for 30 minutes at 37° C. Samples were centrifuged at 1,500 rpm (~200×g) for 10 minutes at 4° C., plasma removed and a 1:100 dilution assayed for LTB$_4$ concentration using ELISA (Assay Designs). Drug concentrations to achieve 50% inhibition ($IC_{50}$) of vehicle LTB$_4$ were determined by nonlinear regression (Graphpad Prism) of % inhibition versus log drug concentration.

Example 28

Rat Peritoneal Inflammation and Edema Assay

A non-limiting example of a rat peritoneal inflammation and edema assay is as follows:
The in vivo efficacy of leukotriene biosynthesis inhibitors was assessed using a rat model of peritoneal inflammation. Male Sprague-Dawley rats (weighing 200-300 grams) received a single intraperitoneal (i.p.) injection of 3 mL saline containing zymosan (5 mg/mL) followed immediately by an intravenous (i.v.) injection of Evans blue dye (2 mL of 1.5% solution). Compounds were administered orally (3 mL/kg in 0.5% methylcellulose vehicle) 2 to 4 hours prior to zymosan injection. One to two hours after zymosan injection, rats were euthanized, and the peritoneal cavity was flushed with 10 mL phosphate buffered saline solution (PBS). The resulting fluid was centrifuged at 1,200 rpm for 10 minutes. Vascular edema was assesses by quantifying the amount of Evans blue dye in the supernatant using a spectrophotometer (Absorbance 610 nm). LTB$_4$ and cysteinyl leukotriene concentrations in the supernatant were determined by ELISA. In one embodiment, drug concentrations to achieve 50% inhibition of plasma leakage (Evans blue dye) and inhibition of peritoneal LTB$_4$ and cysteinyl leukotrienes is calculated by nonlinear regression (Graphpad Prism) of % inhibition versus log drug concentration.

Example 29

Human Leukocyte Inhibition Assay

A non-limiting example of a human leukocyte inhibition assay is as follows:
Blood was drawn from consenting human volunteers into heparanized tubes and ⅓ volume of 3% dextran in 0.9% saline added. After sedimentation of red blood cells a hypotonic lysis of remaining red blood cells was performed and leukocytes sedimented at 1200 rpm. The pellet was resuspended at $1.25 \times 10^5$ cells/mL and 250 µL aliquoted into wells containing 1 µL 100% DMSO (vehicle) or 1 µL drug in 100% DMSO. Samples were incubated for 5 minutes at 37° C. and 5 µL calcium ionophore A23817 (from a 50 mM DMSO stock diluted just prior to the assay in Hanks balanced salt solution (Invitrogen) to 0.5 mM) was added, solutions mixed and incubated for 5 minutes at 37° C. Samples were centrifuged at 1,200 rpm (~200×g) for 10 minutes at 4° C., supernatant removed and a 1:4 dilution assayed for LTB$_4$ concentration using ELISA (Assay Designs). Drug concentrations to achieve 50% inhibition ($IC_{50}$) of vehicle LTB$_4$ were determined by nonlinear regression (Graphpad Prism) of % inhibition versus log drug concentration.

Example 30

Identification of Metabolic Pathways

The metabolic profile of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate was investigated using: (1) rat, dog, monkey, and human hepatic microsomes; (2) rat and human hepatocytes; and (3) bile collected from Sprague-Dawley rats after oral dosing.

In vitro microsomal incubations generated hydroxylated metabolites, which include:
a) hydroxylated 3-[3-tert-butylsulfanyl-1-[4-(6-methoxy-pyridin-3-yl)-benzyl]-5-(pyridin-2-ylmethoxy)-1H-indol-2-yl]-2,2-dimethyl-propionic acid; b) 3-[1-[4-(6-methoxy-pyridin-3-yl)-benzyl]-3-(2-methyl-propane-2-sulfinyl)-5-(pyridin-2-ylmethoxy)-1H-indol-2-yl]-2,2-dimethyl-propionic acid (M2); and c) 3-[3-tert-butylsulfanyl-1-[4-(6-methoxy-pyridin-3-yl)-benzyl]-5-(1-oxy-pyridin-2-ylmethoxy)-1H-indol-2-yl]-2,2-dimethyl-propionic acid (M3).

In vitro hepatocyte incubations formed metabolites, which include:
a) 3-[1-[4-(6-methoxy-pyridin-3-yl)-benzyl]-3-(2-methyl-propane-2-sulfinyl)-5-(pyridin-2-ylmethoxy)-1H-indol-2-yl]-2,2-dimethyl-propionic acid (M2); b) 3-[3-tert-butylsulfanyl-1-[4-(6-methoxy-pyridin-3-yl)-benzyl]-5-(1-oxy-pyridin-2-ylmethoxy)-1H-indol-2-yl]-2,2-dimethyl-propionic acid (M3); and c) the acyl gluconuride of 3-[3-tert-butylsulfanyl-1-[4-(6-methoxy-pyridin-3-yl)-benzyl]-5-(pyridin-2-ylmethoxy)-1H-indol-2-yl]-2,2-dimethyl-propionic acid (M4).

Minor metabolites identified in bile collected from Sprague-Dawley rats after oral dosing include:
a) 3-[3-tert-butylsulfanyl-1-[4-(6-hydroxy-pyridin-3-yl)-benzyl]-5-(pyridin-2-ylmethoxy)-1H-indol-2-yl]-2,2-dimethyl-propionic acid (M5); b) a hydroxylated metabolite where hydroxylation occurs at the phenyl-pyridine moiety; and c) glucuronidation metabolite that is also hydroxylated.

Rat, dog, monkey, and human microsomes or rat and human hepatocytes revealed similar profiles.

The following metabolites were unequivocally identified by chemical and/or enzymatic synthesis and nuclear magnetic resonance spectroscopy and mass spectrum analysis: 3-[1-[4-(6-methoxy-pyridin-3-yl)-benzyl]-3-(2-methyl-propane-2-sulfinyl)-5-(pyridin-2-ylmethoxy)-1H-indol-2-yl]-2,2-dimethyl-propionic acid (M2); 3-[3-tert-butylsulfanyl-1-[4-(6-methoxy-pyridin-3-yl)-benzyl]-5-(1-oxy-pyridin-2-ylmethoxy)-1H-indol-2-yl]-2,2-dimethyl-propionic acid (M3); the acyl gluconuride of 3-[3-tert-butylsulfanyl-1-[4-(6-methoxy-pyridin-3-yl)-benzyl]-5-(pyridin-2-ylmethoxy)-1H-indol-2-yl]-2,2-dimethyl-propionic acid (M4); and 3-[3-tert-butylsulfanyl-1-[4-(6-hydroxy-pyridin-3-yl)-benzyl]-5-(pyridin-2-ylmethoxy)-1H-indol-2-yl]-2,2-dimethyl-propionic acid (M5; which exists also as a pyridon-5-yl tautomer).

Example 31

Extracellular Cytochrome P450 Inhibition

To investigate whether sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate would likely cause any drug-drug interactions, microsomes were incubated test substrates, which are known to be metabolized by CYP enzymes, with or without sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate.

Specific aspects of the incubation conditions for each assay (e.g., protein concentration, incubation time, etc.) were similar to published by Walsky and Obach (Validated assays for human Cytochrome P450 activities. *Drug Met. Disp.* 32:647-660, 2004). In general, microsomes were mixed with buffer (100 mM $KH_2PO_4$, pH 7.4), $MgCl_2$ (3.3 mM) and substrate*, and were kept on ice. Aliquots of this mixture (89 µL) were delivered to each well of a 96-well polypropylene plate which contained an aliquot of inhibitor (1 µL). Final solvent concentrations were 1% (v/v) or less. Incubations were commenced with the addition of 10 µL β-NADPH (10 mM stock) to a final volume of 100 µL. Incubations were terminated by the addition of 1.5-2× acetonitrile containing internal standard (buspirone). Samples were centrifuged, and supernatant was transferred for LC-MS analysis.

The results are presented in Table 12.

metabolites with and without sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate in the incubation. No apparent inhibition was observed for CYP3A4, 1A2, 2C9, and 2D6 enzymes. Sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate weakly inhibited CYP2C19 but the $IC_{50}$ (22 µM) was higher than any likely human plasma concentration and, therefore, should not cause drug-drug interactions.

Example 32

Lack of Cellular Cytochrome P450 Induction

Sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate is not an inducer of P450 CYP3A4 or CYP2C9 in cryopreserved human hepatocytes, according to conversion of substrates to known metabolites with and without sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate in the incubation Cryopreserved human hepatocytes thawed and plated according to the manufacturer's instructions. The cells were warmed and then poured into pre-warmed InVitroGRO CP medium, gently resuspended, and then the cells were counted using Trypan Blue exclusion. Cells were then diluted to $0.7 \times 10^{-6}$ viable cells/ml with CP medium. Each well receive 0.2 ml of the viable cell mixture. The plate was gently shaken to disperse the cells evenly in the well, and the plate was incubated at 37° C., 5% $CO_2$. At 24 hrs, medium was replaced with fresh CP medium. After 48 hrs, CP medium is replaced with HI medium containing the compounds of interest. Sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate was tested at 10 µM, and the positive control, rifampicin was tested at 25 µM. Medium was replaced with fresh medium plus test article 24 hrs later. At 48 hrs, midazolam and diclofenac (50 µM each) were incubated in 0.15 mL of K—H buffer for 4 hrs. Reactions were terminated with addition of 0.15 mL of acetonitrile containing internal standard (buspirone), material centrifuged, and supernatants were transferred for LC-MS analysis. No apparent induction was observed for CYP3A4 and CYP2C9 when tested at 10 µM (U.S. FDA Guidance for Industry, "Drug Interaction Studies—Study Design, Data

TABLE 12

Lack of Extracellular Cytochrome P450 Inhibition

| Cytochrome P450 Enzyme | CYP Reaction | $IC_{50}$ (µM)* | Inhibitor Control ($IC_{50}$ (µM)) |
|---|---|---|---|
| 3A4 | testosterone 6β-hydroxylation | >50 | Ketoconazole (0.06) |
| 3A4 | midazolam 1-hydroxylation | >50 | Ketoconazole (0.01) |
| 2C9 | diclofenac 4'-hydroxylation | 50 | Sulfaphenazole (0.13) |
| 2C19 | mephenytoin 4'-hydroxylation | 22 | Ticlopidine (0.8) |
| 2D6 | dextromethorphan O-demethylation | >50 | Quinidine (0.01) |
| 1A2 | phenacetin O-deethylation | >50 | Furafylline (0.9) |

*of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate.

Sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate is not an inhibitor of P450 (CYP) enzymes, according to conversion of substrates to known Analysis, and Implications for Dosing and Labeling", September 2006). In contrast, rifampicin, a therapeutic agent known to induce CYP3A4 and CYP2C9, induced CYP3A4 11-fold and 2C9 2.5-fold (FIG. 8).

Example 33

Examination of Liver Weight Change in Mice

Significant liver weight increases were not evident in female CD-1 mice after oral administration of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate for 4 days at 250 mg/kg/day when compared with vehicle control (n=7/group, Table 13).

TABLE 13

Liver Weight after Repeat Dosing

| Substance | Liver Weight % body weight (SD) |
|---|---|
| Vehicle | 4.595 (0.3297) |
| sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate | 5.015 (0.9394) |
| Zileuton | 6.248 (0.6612)* |

Data are means (SD) liver weight as percentage of total body weight.
*P < 0.05 vs vehicle control Sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate was prepared as uniform suspension in 0.5% Methyl Cellulose vehicle and administered in a volume of 10 mL/kg of body weight. Mice (7/group) received either vehicle, sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate (250 mg/kg) or Zileuton (250 mg/kg) daily for 4 days. Twenty-four hours following the final administration mice were placed into an enclosed Plexiglas chamber and exposed to $CO_2$ for a period of 1-2 minutes or until breathing ceased. They were then removed and blood was taken via a cardiac puncture and cervical dislocation was performed. Subjects were next placed in a supine position and a midline incision made. All organs were inspected and the livers removed by careful dissection. Liver weights were recorded as well as any gross abnormalities.

Liver weight was not altered significantly (9.1%±7.7%) and necropsy revealed no gross abnormalities. In contrast, zileuton significantly increased liver weight (36.0%±5.4%; P<0.05).

Pharmaceutical Compositions

Pharmaceutical compositions that include 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid, including pharmaceutically acceptable salts and/or pharmaceutically acceptable solvates thereof include a variety of forms. In one aspect, pharmaceutical compositions are in the form of oral dosage forms. In one aspect, the oral dosage forms are formulated as: oral solutions, oral suspensions, tablets, pills, or capsules.

Example 34

Oral Solutions/Suspensions

The sodium salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid was formulated into solutions suitable for oral administration to a mammal. The pharmokinetic profile of various oral solutions was investigated in male Sprague-Dawley rats and the results are outlined in Table 14.

TABLE 14

Oral Absorption of Pharmaceutical solutions in male Sprague-Dawley rats.

| Formulation | Dose (mg/kg) | AUC (hr * µg/mL) | $C_{max}$ (µg/mL) | $T_{max}$ (hr) |
|---|---|---|---|---|
| 0.5% carboxymethylcellulose | 10 | 26.0 | 9.0 | 1.5 |
| 10 mM Sodium Carbonate:Syrpalta (3:7 ratio) | 5 | 6.18 | 2.41 | 2.00 |
| Water:Syrpalta (7:3 ratio) | 5 | 7.93 | 2.97 | 2.00 |
| 50 mM Sodium Carbonate:Syrpalta (7:3) | 5 | 8.66 | 2.75 | 2.00 |
| 10 mM Sodium Carbonate:Sorbitol (95:5 ratio) | 5 | 6.19 | 1.65 | 1.67 |
| 1 pk Equal ® in 10 mM Sodium Carbonate | 5 | 5.88 | 1.99 | 2.00 |
| 10 mM Sodium Carbonate:Simple syrup (95:5 ratio) | 5 | 6.33 | 2.40 | 1.67 |
| 3% Aspartame in 50 mM Sodium Carbonate | 5 | 14.29 | 4.43 | 2.67 |
| 50 mM Sodium Carbonate | 5 | 9.20 | 4.02 | 1.20 |
| 10 mM Sodium Carbonate | 5 | 9.33 | 3.39 | 1.67 |
| 10 mM Sodium Carbonate/EtOH (90:10) | 10 | 6.30 | 2.55 | 1.67 |
| 10 mM Sodium Carbonate/EtOH (80:20) | 5 | 7.92 | 2.61 | 2.67 |
| Olive oil | 2.8 | 9.14 | 2.76 | 2.00 |
| Water | 10 | 27.68 | 10.31 | 1.67 |

The sodium salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid is rapidly absorbed in the stomach and upper gastrointestinal tract as indicated by $T_{max}$ of ≥2 hrs. Different formulations appear to give a 2× range of AUC (6-13 hr*µg/mL) and $C_{max}$ values (2.5-5.0 µg/mL) (values were dose adjusted to 5 mg/kg).

Example 35

Oral Aqueous Solutions Suitable for Human Administration

In one embodiment, oral aqueous solutions suitable for human use are prepared for oral administration. In one embodiment, oral aqueous solutions are prepared prior to administration.

The sodium salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid is stored/packaged in any container that does not affect the chemical stability of the salt. In one embodiment, the sodium salt of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid is packaged in a high density polyethylene (HDPE) drum with an HDPE air and water-tight lid.

Aqueous solutions suitable for oral administration to human are prepared as follows:
A solution of 10% (w/w) ethanol (United States Pharmacopeia, USP), and 90% (w/w) aqueous sodium carbonate buffer (USP, NF—National Formulary) (0.010 M, pH 9-10), sweetened with aspartame (0.003% w/w; NF) is added to the sodium salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid. The oral solution of the sodium salt of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid, when constituted, will have a final concentration of 10 mg/mL.

The manufacturing process for the preparation of oral aqueous solutions involves weighing individual (1) gram samples of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate into amber glass jars or other suitable container(s). In one embodiment, the amber glass jars are fitted with child-proof polypropylene lined polypropylene caps. This is followed by constitution of the drug product oral solution at a concentration of 10 mg/mL sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate through the addition of 100 mL of 10 mM aqueous sodium carbonate buffer containing 10% w/w absolute ethanol sweetened with aspartame (0.003% w/w). After mixing with the sweetened buffer, the solution is visually inspected to verify that the drug substance is completely dissolved. The following is a description of the drug product manufacturing process:

1. In a manufacturing vessel, combine sodium carbonate, ethanol, aspartame, and purified water.
2. To each 1 g bottle of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate, add 100 mL of the solution prepared in Step 1.
3. Agitate the mixture until a clear solution is achieved (~0.25-0.5 hours).

The final concentration of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate drug substance aqueous solution is 10 mg/mL.

Solid Oral Dosage Forms

Crystalline sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate (Form C) was formulated into tablets that contain an immediate release matrix. Crystalline sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate (Form C) was also formulated into tablets that contain an extended release matrix. Crystalline sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate (Form C) was also formulated into gelatine filled capsules without excipients or with the excipient microcrystalline cellulose.

Example 36

Immediate Release (IR) Tablets

Tablets were prepared that exhibit an immediate release profile as referenced by FDA guidelines ("Dissolution Testing of Immediate Release Solid Oral Dosage Forms", issued August 1997, Section IV-A). In one aspect, immediate release tablets were prepared using the ingredients shown in Table 15. Drug loading was kept below 20% w/w % in the immediate release formulation.

TABLE 15

Formulation composition 50 mg IR tablets

| Ingredient (Vendor, lot number or catalog number) | % w/w | mg/tablet | g/200 g |
|---|---|---|---|
| Crystalline sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate (Form C) | 15.00 | 50.00 | 30.00 |
| Silicified microcrystalline cellulose (Prosolv SMCC 90 HD) (JRS Pharma, P9B3C21X) | 45.00 | 150.0 | 90.00 |
| Mannitol (Mannogem EZ spray Dried) (API Pharma, Inc., 2003A3) | 34.00 | 113.3 | 64.00 |
| Crospovidone (Polyplasdone XL) (ISP, 03300098228) | 5.0 | 16.7 | 10.00 |
| Magnesium Stearate (Hvual Veaetable Souce) CK WITCO, 377073 | 1.00 | 3.3 | 2.00 |
| Total | 100.00 | 333.3 | 200 |

The manufacturing processes for the IR tablets is as follows:
Weigh the appropriate amount of each ingredient. Prescreen each ingredient through a 70# sieve (use non-static bags). Charge all ingredients excluding magnesium stearate into a 1-pint V-blender and dry blend for 30 minutes. Charge the prescreened magnesium stearate into the blender and dry blend for 1 minute. Discharge the powder blend into a rotary press machine. The powder blend is tableted by compaction on a single station Colton tablet press equipped with 10 mm round-shaped tooling (IR). The summary of the chemical and physical properties of the IR tablets is described in Table 16.

TABLE 16

Summary of Chemical and Physical Results (T = 0) of the 50 mg Immediate release Tablets

| Hardness (n = 3, kP) | Friability (n = 20, % loss) | Average Weight (mg, n = 10) | Disintegration (n = 6) | Assay (n = 3, mg/tablet) | % Purity (AUC) |
|---|---|---|---|---|---|
| 9.6 ± 1.5 | 0.23 | 333.3 ± 5.6 | 82 ± 20 sec | 60.8 ± 1.5 | 98.1 |

Example 37

Dissolution Studies of the Immediate Release Tablets

The dissolution properties of immediate release tablets were analyzed using USP apparatus 1 (basket). Details for dissolution analysis using USP apparatus and methods of use are described in USP general Chapter 711, and USP Chapter 1092 "The Dissolution Procedure: Development and Validation, Pharmacopeial Forum", 31(5), 2005, p 1463.

Dissolution Testing Conditions:

Medium (1% sodium lauryl sulfate, pH 7.0); Volume (500 mL); Temperature (37° C.); USP method (Basket); Speed (100 rpm); Assay method (HPLC, UV detection). In vitro dissolution profiles were measured using the USP basket method rotating at 100 rpm in a medium consisting of 1 SLS and pH=7 at 37° C. (sink conditions for sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate). Levels of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate in the dissolution bath were measured by direct sampling and analysis by HPLC under the following conditions:

| Column: | Waters, SymmetryShield RP8, 4.6 × 75 mm, 3.5 μm |
|---|---|
| Mobile Phase A: | 0.1% TFA in deionized water |
| Mobile Phase B: | 0.1% TFA in acetonitrile |
| Column temp: | 25° C. |
| Injection volume: | 10 μL |
| Autosampler temp: | 25° C. |
| UV Detection: | 260 nm |
| Flow: | 1 mL/min |
| Run time: | 10 min |

Gradient conditions for the HPLC runs were:

| Time (minutes) | % of B |
|---|---|
| 0 | 45 |
| 10 | 45 |

The results of the dissolution studies of the immediate release tablets are shown in Table 17.

TABLE 17

Dissolution profile of IR table formulation, (n = 6)

| Time (minutes) | % of release | Standard deviation |
|---|---|---|
| 0 | 0 | 0 |
| 10 | 107.4 | 2.1 |
| 20 | 108.8 | 1.8 |
| 30 | 109.3 | 2.2 |
| 45 | 105.3 | 1.9 |
| 60 | 105.7 | 1.7 |
| 120 | 107.0 | 1.9 |

The results of the dissolution studies show that complete release of the active ingredient is achieved by the earliest time point measured (10 minutes). The results are consistent with a well-performing immediate release formulation (FDA guidelines, "Dissolution Testing of Immediate Release Solid Oral Dosage Forms", issued August 1997, Section IV-A).

Example 38

Extended Release (ER) Tablets

Tablets were prepared that exhibit an extended release profile as referenced by FDA Guidelines ("Extended Release Oral Dosage Forms: Development, Evaluation, and Application of In Vitro/In Vivo Correlations", Food and Drug Administration, CDER, September 1997, Page 17). In one aspect, extended release tablets were prepared using ingredients listed in Table 18. Drug loading was kept below 20% w/w % in the ER formulations.

TABLE 18

Formulation composition, 100 mg ER tablets

| Vendor, lot & grade | % w/w | mg/tablet | g/400 g |
|---|---|---|---|
| Crystalline sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate (Form C) | 15.0 | 100.00 | 60.00 |
| Silicified microcrystalline cellulose (Prosolv SMCC 90 HD)JRS, P9B3C21X | 20.0 | 133.3 | 80.00 |
| Mannitol (Mannogem EZ spray Dried) API Pharma, Inc., 2003A3 | 24.0 | 160.0 | 96.00 |

TABLE 18-continued

| Formulation composition, 100 mg ER tablets | | | |
|---|---|---|---|
| Vendor, lot & grade | % w/w | mg/tablet | g/400 g |
| Sodium carbonate monohydrate, NF ISP, 03300098228 | 20.0 | 133.3 | 80.00 |
| Hydroxypropyl methylcellulose K4M, NF DOW, SI01012N12 | 20.0 | 133.3 | 80.00 |
| Magnesium Stearate (Hyual Vegetable Souce) CKWITCO, 377073 | 1.00 | 6.7 | 4.00 |
| Total | 100.00 | 666.6 | 400 |

The manufacturing processes for the ER tablets was as follows:
Weigh the appropriate amount of each ingredient. Prescreen each ingredient through a 70# sieve (use non-static bags). Charge all ingredients excluding magnesium stearate into a 1-pint V-blender and dry blend for 30 minutes. Charge the prescreened magnesium stearate into the blender and dry blend for 1 minute. Discharge the powder blend into a rotary press machine. The powder blend is tableted by compaction on a single station Colton tablet press equipped with 15 mm bisected oval shaped tooling. The summary of the chemical and physical properties of the ER tablets is described in Table 19.

TABLE 19

Summary of Chemical and Physical Results (T = 0) of the 100 mg Extended Release Tablets.

| Hardness (n = 3, kP) | Friability (n = 20, % loss) | Average Weight (mg, n = 10) | Disintegration (n = 6) | Assay (n = 3, mg/tablet) | % Purity (AUC) |
|---|---|---|---|---|---|
| 15.7 ± 0.8 | 0.31 | 664.6 ± 8.3 | >9 minutes | 101.0 ± 8.2 | 98.2 |

Conditions used to evaluate the dissolution of the extended release tablets:
Medium (1% sodium lauryl sulfate, pH 7.0); Volume (1000 mL); Temperature (37° C.); USP method (Basket); Speed (100 rpm); Assay method (HPLC, UV detection). In vitro dissolution profiles were measured using the USP basket method rotating at 100 rpm in a medium consisting of 1 SLS and pH=7 at 37° C. (sink conditions for sodium 3-[5-(pyrid-2-ylmethoxy)-3-(2-methyl-2-propylthio)-1-[4-(2-methoxy-pyrid-5-yl)benzyl]indol-2-yl]-2,2-dimethylpropionate).
Levels of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate in the dissolution bath were measured by direct sampling and analysis by HPLC under the following conditions:

| Column: | Waters, SymmetryShield RP8, 4.6 × 75 mm, 3.5 µm |
|---|---|
| Mobile Phase A: | 0.1% TFA in deionized water |
| Mobile Phase B: | 0.1% TFA in acetonitrile |
| Column temp: | 25° C. |
| Injection volume: | 10 µL |
| Autosampler temp: | 25° C. |
| UV Detection: | 260 nm |
| Flow: | 1 mL/min |
| Run time: | 10 min |

Gradient conditions for the HPLC runs were:

| Time (minutes) | % of B |
|---|---|
| 0 | 45 |
| 10 | 45 |

The results of the dissolution studies of the immediate release tablets are shown in Table 20.

TABLE 20

| Dissolution profile of ER table formulation, (n = 6) | | |
|---|---|---|
| Time (hours) | % of release | Standard deviation |
| 0 | 0 | 0 |
| 0.25 | 2.0 | 0.7 |
| 0.5 | 3.8 | 1.3 |
| 0.75 | 6.0 | 2.0 |
| 1 | 8.1 | 2.6 |
| 2 | 19.5 | 5.3 |
| 3 | 32.7 | 7.9 |
| 6 | 78.8 | 14.4 |
| 12 | 93.8 | 5.2 |
| 18 | 98.8 | 3.6 |
| 24 | 101.4 | 3.4 |

The dissolution profile for the 100 mg ER tablet showed an apparent first order extended release profile for the active ingredient over the course of approximately 6 hours, with less than 20% of the dose released by the 2 hour time point and complete release achieved by 24 hours. These results are consistent with a well-performing extended release formulation (FDA Guidance for Industry, "Extended Release Oral Dosage Forms: Development, Evaluation, and Application of In Vitro/In Vivo Correlations", Food and Drug Administration, CDER, September 1997).

Example 39

Capsule Formulations for Use in Sprague-Dawley Rat

Two sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate (Form C) formulations were prepared using size 9 hard gelatine capsules for dosing in rats by gavage. Formulation 1 contained sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate in combination with the excipient microcrystalline cellulose; formulation 2 contained sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate without any added excipients. In general, when compared to values obtained in the rat for 0.5% methylcellulose oral solutions (Table 14), Tmax values for the capsules were delayed (2.7 and 3.3 hours versus 2 hours for the oral solution; Tables 21 and 14, respectively) and AUC and Cmax values for the capsules were lower compared to the oral solution (Tables 21 and 14, respectively).

TABLE 21

|  | Formulation 1 | Formulation 2 |
| --- | --- | --- |
| Dose (mg/kg) | 11 | 11 |
| AUC (hr * μg/mL) | 4.85 | 13.20 |
| Cmax (μg/mL) | 1.47 | 3.70 |
| Tmax (hr) | 2.67 | 3.33 |

Example 40

Regional Dosing Study

Male Sprague-Dawley rats (weighing from about 200 to about 300 grams) received a single injection of a solution of the sodium salt of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid (5% carboxymethylcellulose) either in the duodenum or ileuem. The results of the regional dosing study are displayed in Table 22.

TABLE 22

Regional Dosing Studies in Rat

| Formulation | Dose (mg/kg) | AUC (hr * μg/mL) | Cmax (μg/mL) | Tmax (hr) |
| --- | --- | --- | --- | --- |
| 0.5% carboxymethylcellulose in Duodenum | 10 | 55.32 | 17 | 1.33 |
| 0.5% carboxymethylcellulose in Ileum | 5 | 1.84 | 0.67 | 0.50 |

The results shown in Table 22 demonstrate that sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate is mainly absorbed in the upper gastrointestinal tract.

Example 41

Comparison of Pharmacokinetics Resulting from Oral Dosage Form

The oral absorption of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate was investigated in female Beagle dogs in the fasted state using an oral solution and two different solid oral dosage formulations (50 mg immediate release (IR) tablets and 100 mg extended release (ER) tablets). For comparison, an IV formulation was also tested. Table 18 summarizes the results of the experiments of administration of the various oral formulations to female beagle dogs.

Dosing of female Beagle dogs (weights 6.7-12.8 kg) was performed at LAB Pre-Clinical Research International, Inc. Sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate was dosed intravenously at 2 mg/kg (PEG400:Water 3:1) and orally at 5 mg/kg (0.5% methylcellulose).

TABLE 23

Single-Dose Pharmacokinetics in Beagle Dogs

| Route | IV | Oral Suspension (0.5% methylcellulose suspension) | Oral 100 mg IR | Oral 100 mg ER |
| --- | --- | --- | --- | --- |
| Dose | 2 mg/kg | 5 mg/kg | 10 mg/kg | 10 mg/kg |
| Sex | f | f | f | f |
| $T_{max}$ (hr) | 0.017 | 1.7 | 1.3 | 2 |
| $C_{max}$ (μg/mL) | 3.2 | 6 | 11.2 | 5.2 |
| $t_{1/2}$ (hr) | 7.7 | NC | NC | NC |
| $AUC_{0-\infty}$ (μg·h/mL) | 11.9 | 18.9 | 47.5 | 20 |
| $AUC_{dose-adjusted}$ | 6.0 | 3.8 | 4.8 | 2 |
| $CL_p$ (mL/min/kg) | 2.9 | NA | NA | NA |
| $Vd_{ss}$ (L/kg) | 0.4 | NA | NA | NA |
| F % | 100 | 63 | 80 | 33 |

Data are group means.
Half-life was calculated from 6 to 24 hours.
AUC = area under plasma concentration-time curve;
$C_{max}$ = peak plasma concentration;
$Cl_p$ = systemic plasma clearance;
F % = bioavailability calculated from $AUC_{0-\infty}$;
iv = intravenous;
NA = not applicable;
NC = not calculated;
$t_{1/2}$ = terminal half-life;
$T_{max}$ = time to peak plasma concentration;
$Vd_{ss}$ = volume of distribution at steady state.

The immediate release tablet showed similar pharmacokinetic parameters as that of the oral suspension, with an oral bioavailability of 63 vs 80% (suspension vs. immediate release tablet), respectively. Oral AUC values were dose proportional, with values of 3.8 and 4.8 μg*hr/mL, respectively. The extended release tablet showed a reduced oral bioavailability (33%) and AUC value (2 μg*hr/mL).

Sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate appears to be rapidly absorbed in the stomach and upper gastrointestinal tract ($T_{max}$=1.7 hrs). In one embodiment, sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate is formulated using an immediate release (IR) tablet, as the AUC and $C_{max}$ values were comparable to solution. The extended release (ER) tablet showed a 2-fold lower AUC and $C_{max}$ when compared to solution.

Example 42

A Phase 1, Single-Center, Double-Blind Study in Healthy Human Volunteers Study Objective Single and multiple doses of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate drug substance were orally administered to healthy male or female (male only for Multiple Dose Phase) volunteers and assessments of the following were made: i) safety of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate drug substance; ii) tolerability of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate drug substance; iii) pharmacokinetics (PK) of sodium 3-[5-(pyrid-2-ylmethoxy)-3-(2-methyl-2-propylthio)-1-[4-(2-methoxypyrid-5-yl)benzyl]indol-2-yl]-2,2-dimethylpropionate drug substance; iv) the effects of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance on pharmacodynamic (PD) markers: whole blood ionophore-stimulated leukotriene $LTB_4$ and urinary $LTE_4$ production.

In one embodiment, the therapeutic goal is the minimum dose that fully inhibits $LTE_4$ but only partially inhibits $LTB_4$ production at the end of the dosing interval—a profile that provides suppression of the key cysteinyl leukotrienes in asthma, and partial inhibition of $LTB_4$ which is important in the inflammation associated with cardiovascular disease.

Study Design

The following outlines a single-center, single and multi-dose, randomized, double-blind, placebo controlled study to determine the safety, tolerability, pharmacokinetics and pharmacodynamics of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance. The study is divided into two phases (Single and Multiple Dose Phases).

In the Single Dose Phase, either male or female subjects are given a starting dose of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance of 50 mg and the dose is escalated up to 1000 mg.

In the Multiple Dose Phase, male subjects are given 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance daily for 11 days. One cohort in the Multiple Dose Phase receives twice daily dosing. Each dose cohort comprises about six (6) subjects receiving 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance and two (2) subjects receiving placebo.

The doses are escalated between cohorts as each prior dose is shown to be well tolerated. The dosing progression is adapted as appropriate and it is feasible that lower doses are evaluated in later periods.

Dose Progression and Dosing Interval

The following dosing cohorts are evaluated in the study:

| Cohort | Phase of Study | |
| --- | --- | --- |
| | Single Dose | Multiple Dose |
| 1 | 50 mg | 150 mg |
| 2 | 150 mg | 450 mg |
| 3 | 300 mg | 1000 mg |
| 4 | 600 mg | 50 mg |
| 5 | 1000 mg | |

Study design: Single center, double-blind, randomized, placebo-controlled, single dose followed by multiple dose study.

Sample size: Single Dose Phase: Eight (8) subjects (6 active, 2 placebo) per dose level; up to 5 dose levels are planned (a total of 40 subjects if all 5 dose levels are completed).

Multiple Dose Phase: Eight (8) subjects (6 active, 2 placebo) per dose level; up to 4 dose levels planned (a total of about 32 subjects if all 4 dose levels completed).

Subject type: Healthy, ambulatory, non-smoking, male or female (for Multiple Dose Phase male only) volunteers aged 18 to 65 years. Preferably, at least three (3) of each gender per dose cohort will be enrolled in the Single Dose Phase (for Multiple Dose Phase male only).

Formulations: 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid drug substance is supplied as an oral powder for reconstitution (see Example 17). Placebo solution to match. The finished aqueous solution is prepared in the clinical study site pharmacy within 24 hours of dosing. The study drug is stored at room temperature between 15-30° C. (59-86° F.) and protected from light.

Route of Administration: All doses are administered orally with approximately 100 mL of water rinse. Subjects are fasted for at least 8 hours prior to dosing and for 2 hours after dosing.

Study Parameters: Assessment of:

Pharmacokinetics: Concentrations of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid in plasma samples are determined by validated LCMS methods.

Pharmacodynamics: Whole blood ionophore-stimulated leukotriene $LTB_4$ and urinary $LTE_4$ production are assayed by ELISA and mass spectrometry, respectively.

Duration of Individual Subject Participation

Single Dose Phase: 4 days (not including screening)

Multiple Dose Phase: 14 days (not including screening)

Total duration of study: Approximately 3.5 to 5 weeks

Screening Visit Procedures

The following examinations and assessments are performed within 21 days (3 weeks) prior to study drug administration to determine whether the subject satisfies inclusion and exclusion criteria. Those subjects not fulfilling all inclusion and exclusion criteria are not enrolled in the study. Screening visit procedures are as follows:

Subjects report to the investigational site in the morning, before breakfast, following at least an 8-hour overnight fast. Informed consent is obtained before performing any study-related procedures, including screening procedures. Collect medical history. Measure height and weight. Perform physical examination (including blood pressure, heart rate (pulse), respiratory rate, and body temperature). Record concomitant medications. Obtain fasting blood samples for hematology determinations. Obtain fasting blood samples for serum chemistry. Obtain fasting urine samples for urinalysis and urine drug screen.

Procedures for Evening Prior to Day 1

Subjects report to the investigational site at approximately 3:00 PM in the afternoon prior to Day 1 study drug administration. No food is permitted after 10:00 PM (may have a standardized snack prior to 10:00 PM). The visit procedures are as follows:

Obtain updated medical history. Conduct a targeted physical examination (including blood pressure, heart rate (pulse), respiratory rate, and body temperature) if ≥2 weeks since the screening physical examination. Collect urine for baseline (pre-dose) $LTE_4$.

Day 1 Procedures

Obtain pre-dose fasting blood samples for hematology determinations. Obtain pre-dose fasting blood samples for serum chemistry determinations. Obtain pre-dose blood samples (5 mL EDTA and 4 mL heparinized) for baseline PK and $LTB_4$. Collect 'spot' urine prior to study drug administration for baseline (pre-dose) $LTE_4$. Administer study drug. Collect blood samples (5 mL EDTA) for PK of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid at 0.25, 0.5, 1, 2, 3, 4, 6, 8, 12, and 16 hours. Collect blood samples (2 mL heparinized) for $LTB_4$ at 0.5, 1, 2, 3, 4, 6, 8, and 12 hours. Collect urine for $LTE_4$ for the following separate intervals: 0-3, 3-6, 6-9, and 9-12 hours. For twice daily dosing group (if conducted): administer study drug 12 hours±30 minutes after prior dose, preceded by ≥2 hours fast.

Day 2 Procedures (24→Up to 48 Hours Post Dosing)

For All Subjects (Note: No study drug is administered to Single Dose Phase subjects):

Obtain pre-dose fasting blood samples for hematology determinations. Obtain pre-dose fasting blood samples for serum chemistry determinations. Collect blood samples (5 mL EDTA) for PK of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid at 24 and 36 hours after the first study drug administration. Collect blood samples (2 mL heparinized) for $LTB_4$ at 24 hours after the first study drug administration; 4 mL blood will be collected at this time point in the Single Dose Phase. Collect 'spot' urine sample for $LTE_4$ at 24 and 36 hours after first study drug administration.

For Multiple Dose Phase Subjects:

Administer study drug. Record vitals signs 2 and 12 hours after study drug administration.

For twice daily dosing group (if conducted): administer study drug 12 hours±30 minutes after prior dose, preceded by ≥2 hours fast.

Day 3 Procedures (≥48 Hours Post Dosing)

For All Subjects (Note: No study drug is administered to Single Dose Phase subjects):

Collect blood samples (5 mL EDTA) for PK of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid at 48 and 60 hours after the first study drug administration. Collect 'spot' urine sample for $LTE_4$ at 48 hours after first study drug administration.

For Multiple Dose Phase Subjects:

Collect blood samples (5 mL EDTA) for PK of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid at 1, 2, 3, 4, and 6 hours. Administer study drug. For twice daily dosing group (if conducted): administer study drug 12 hours±30 minutes after prior dose, preceded by ≥2 hours fast.

Days 4-10 Procedures

For Multiple Dose Phase subjects: Collect 'spot' urine sample for $LTE_4$ at 72 hours after the first study drug administration. Collect daily pre-dose fasting blood samples (5 mL EDTA) for PK of 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid. Administer study drug daily. For twice daily dosing group: administer study drug 12 hours±30 minutes after prior dose, preceded by ≥2 hours fast.

Day 11 Procedures

Obtain pre-dose blood samples (5 mL EDTA and 2 mL heparinized) for PK and $LTB_4$. Collect pre-dose urine for $LTE_4$. Administer study drug (last dose of drug). Collect blood samples (5 mL EDTA) for PK of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid at 0.5, 1, 2, 3, 4, 6, 8, 12, and 16 hours. Collect blood samples (2 mL heparinized) for $LTB_4$ at 0.5, 1, 2, 3, 4, 6, 8, and 12 hours. Collect urine for $LTE_4$ for the following separate intervals: 0-3, 3-6, 6-9, and 9-12 hours after study drug administration.

Day 12 Procedures (24→Up to 48 Hours Post Last Dose)

Record vital signs 24 hours after Day 11 study drug administration. Collect blood sample (5 mL EDTA) for PK of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid at 24 and 36 hours after Day 11 study drug administration. Collect blood sample (4 mL heparinized) for $LTB_4$ at 24 hours after Day 11 study drug administration. Collect 'spot' urine sample for $LTE_4$ at 24 hours after Day 11 study drug administration.

Day 13 Procedures

Collect blood sample (5 mL EDTA) for PK of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid at 48, and 60 hours after Day 11 study drug administration. Collect 'spot' urine sample for $LTE_4$ at 36 and 48 hours after Day 11 study drug administration.

End-of-Study Procedures (≥72 Hours after Study Drug Administration)

Conduct a physical exam (including blood pressure, heart rate (pulse), respiratory rate, and body temperature). Obtain fasting blood samples for hematology determinations. Obtain fasting blood samples for serum chemistry determinations. Obtain 'spot' fasting urine samples for urinalysis and urine drug screen. Collect blood sample (5 mL EDTA) for PK of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid at 72 hours after study drug administration. Collect 'spot' urine sample for $LTE_4$ at 72 hours after study drug administration. Record concomitant medications.

Procedural Time Windows

The following time windows were utilized in this study. Unless stated otherwise, there is a window of ±15 minutes for study specified assessments. For safety laboratory assessments (fasting hematology and serum chemistry), the window is ±4 hours of the specified time points. For urine spot checks, the window is ±30 minutes of the specified time points.

Volume of Blood Collected

The following is the estimated volume of blood to be collected during the Single and the Multiple Dose Phases of the study. In BID dosing of the Multiple Dose Phase, the volume of blood collected for the PK and PD assessments is less than amount stated in the table below.

TABLE 24

| | Blood Volume Collected | | | | | |
|---|---|---|---|---|---|---|
| | Single Dose Phase | | | Multiple Dose Phase | | |
| | Labs | PK | PD | Labs | PK | PD |
| | 40 mL | 90 mL | 24 mL | 70 mL | 210 mL | 44 mL |
| Total | | 154 mL | | | 324 mL | |

Analytical Procedure

Plasma concentrations of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid were determined using validated LC/MS method(s). Whole blood ionophore-stimulated leukotriene $LTB_4$ and urinary $LTE_4$ production were assayed by ELISA and mass spectrometry, respectively.

Analysis of Samples

Concentrations of 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid were determined in plasma samples collected from subjects. Similarly, concentrations of $LTB_4$ in plasma and urinary $LTE_4$ were determined in blood and urine samples collected.

Figure 3:
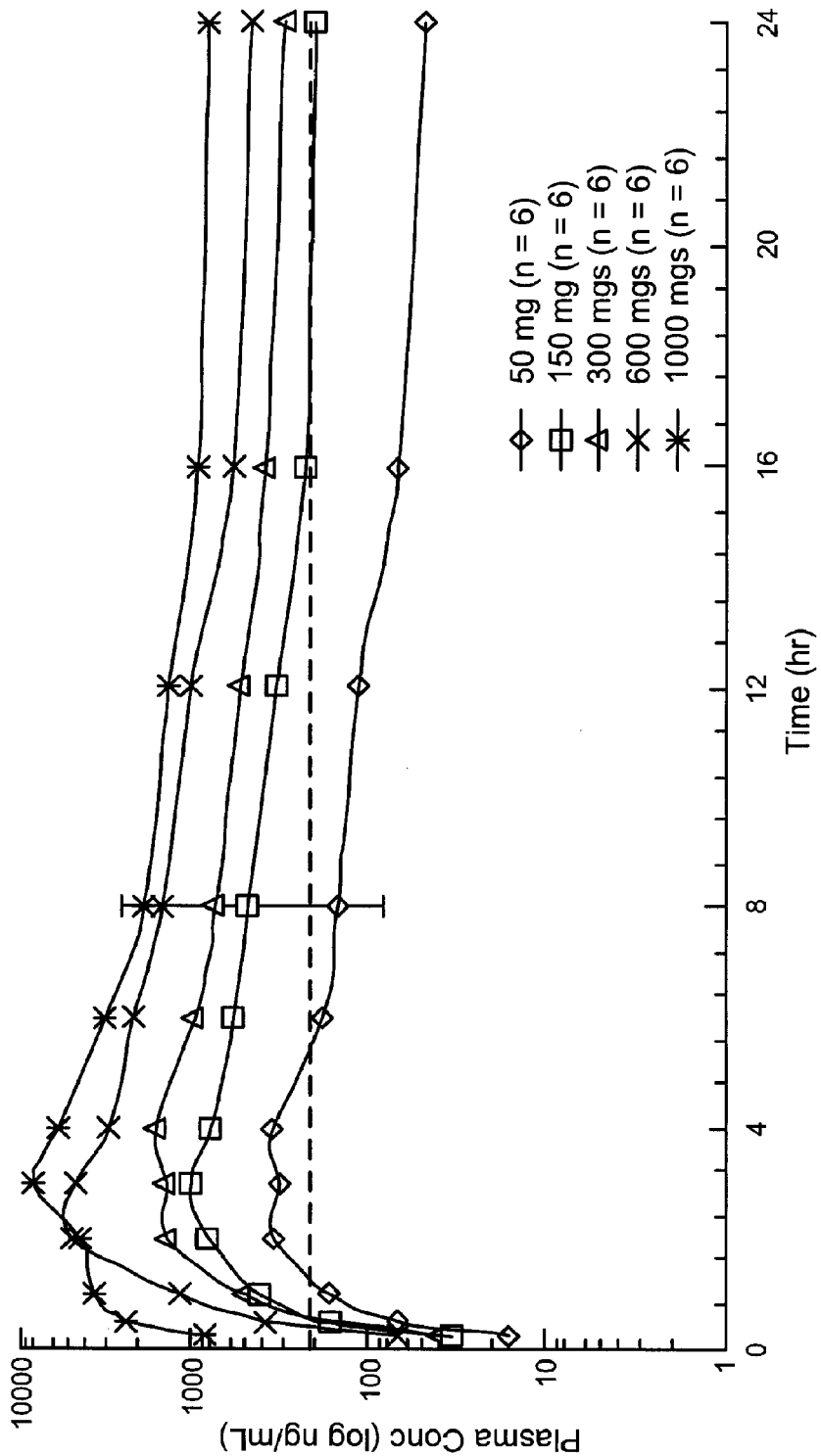
FIG. 3 presents pharmacokinetic properties of single dose administrations of an aqueous solution sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate to healthy adult human subjects in the fasted state.

The pK results from the single dose study are presented in Table 25 and FIG. 3.

TABLE 25

Single Dose Pharmacokinetic data using oral solutions.

| Dose of Active | $T_{max}$ (hr) AVE ± SD | $C_{max}$ (mM) AVE ± SD | $t_{1/2}$ (hr) AVE ± SD | $AUC_{0-24}$ (hr * mM) AVE ± SD |
|---|---|---|---|---|
| 50 mg | 3 ± 0.8 | 0.65 ± 0.32 | 7.7 ± 0.3 | 5.4 ± 2.5 |
| 150 mg | 2.5 ± 0.5 | 1.8 ± 1.1 | 10 ± 2 | 15.9 ± 8.7 |
| 300 mg | 3.2 ± 1 | 3.1 ± 1.4 | 12.3 ± 3.1 | 25.8 ± 7.4 |
| 600 mg | 2 ± 0.6 | 8.1 ± 5.3 | 8.8 ± 1.3 | 54 ± 35.3 |
| 1000 mg | 3 ± 0.8 | 13 ± 5 | 7.6 ± 4.6 | 85 ± 44 |

Figure 4:
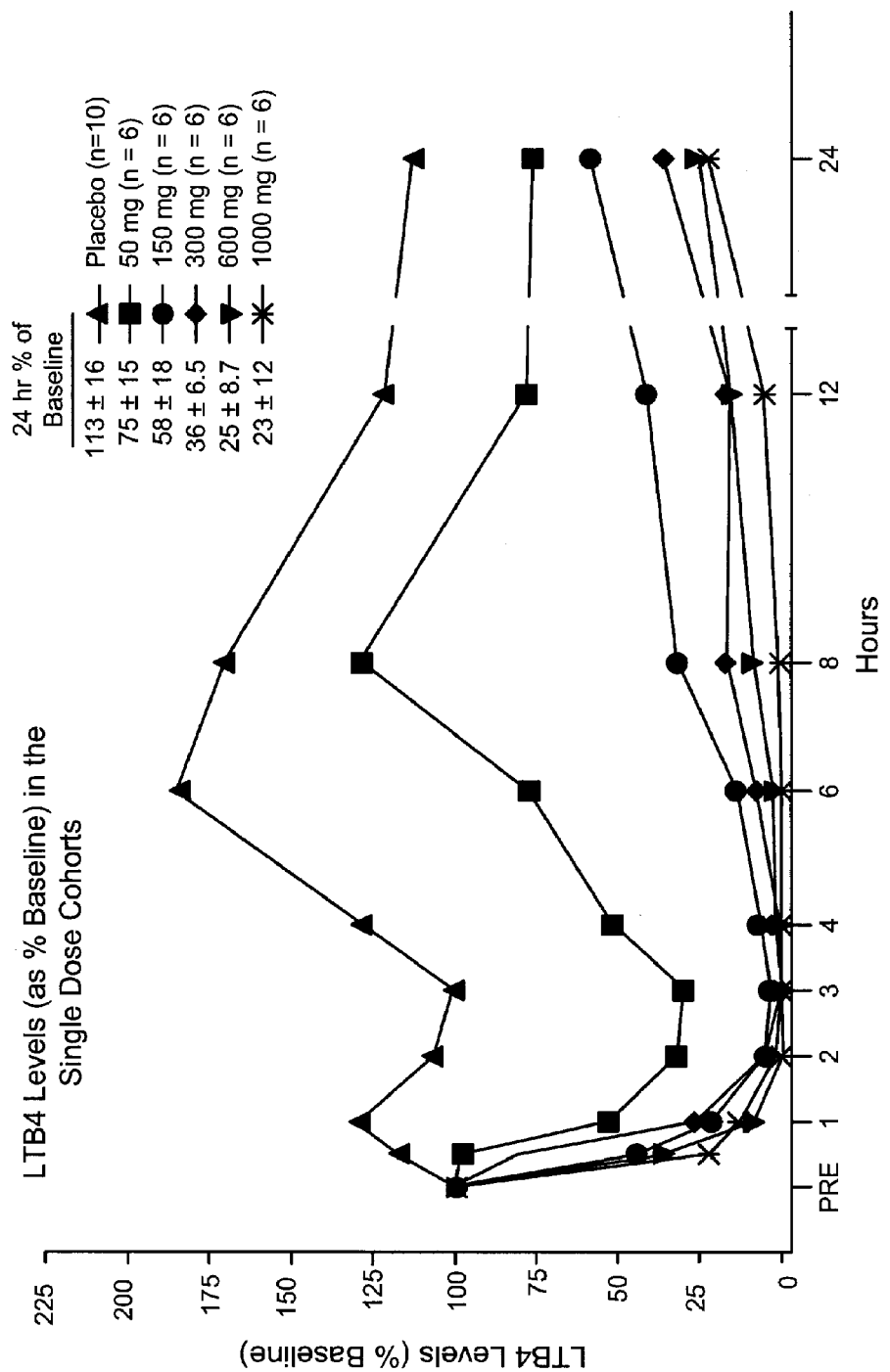
FIG. 4 presents pharmacodynamic properties (blood $LTB_4$ levels) of single dose administrations of aqueous solutions of sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate to healthy adult human subjects in the fasted state.
Figure 5:
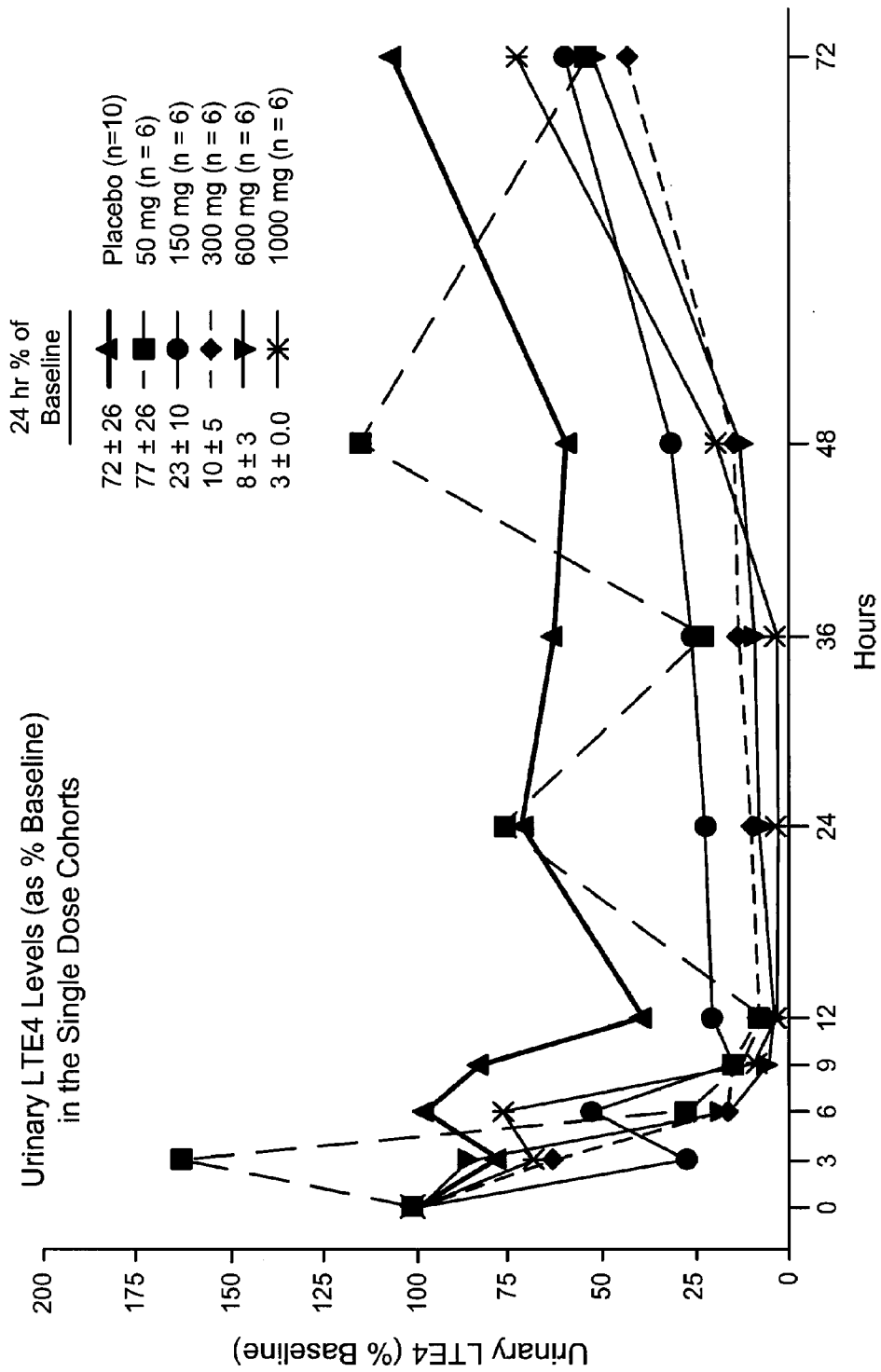
FIG. 5 presents pharmacodynamic properties (urinary $LTE_4$ levels) of single dose administration of aqueous solutions of sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate to healthy adult human subjects in the fasted state.

The pharmacodynamic properties after the single doses were administered (blood $LTB_4$ levels; urinary $LTE_4$ levels) are presented in FIGS. 4 and 5 and Table 26.

TABLE 26

Single Dose $LTB_4$ data using oral solutions.

| Dose of Active | $LTB_4$ level at t = 24 hrs. (% of baseline) | $LTE_4$ level at t = 24 hrs. (% of baseline) |
|---|---|---|
| Placebo | 113 ± 16 | 72 ± 26 |
| 50 mg | 75 ± 15 | 77 ± 26 |
| 150 mg | 58 ± 18 | 23 ± 10 |
| 300 mg | 36 ± 6.5 | 10 ± 5 |
| 600 mg | 25 ± 8.7 | 8 ± 3 |
| 1000 mg | 23 ± 12 | 3 ± 0 |

From the single dose studies, the following pK and pharmacodynamic properties may be obtained from a single dose administration to a human:

$C_{max} \leq 5$ μMol; ≥80% inhibition of urinary $LTE_4$ levels at 24 hours; ≥80% inhibition of blood $LTB_4$ levels at 8 hours (Ionophore Challenge); ≥30% inhibition of blood $LTB_4$ levels at 24 hours (Ionophore Challenge).

The pK results from multiple dose administration are presented in Table 27.

TABLE 27

Multiple Dose Pharmacokinetic data using oral solutions (Day 1).

| Dose of Active | $T_{max}$ (hr) AVE ± SD | $C_{max}$ (mM) AVE ± SD | $t_{1/2}$ (hr) AVE ± SD | $AUC_{0-24}$ (hr * mM) AVE ± SD |
|---|---|---|---|---|
| 150 mg | 2.5 ± 0.5 | 1.9 ± 1.1 | 9.2 ± 2 | 11.3 ± 5 |
| 450 mg | 2.7 ± 0.5 | 4.7 ± 2.2 | 13.2 ± 3.9 | 34.2 ± 7.9 |
| 1000 mg | 2.3 ± 0.5 | 14.4 ± 5.1 | 11.2 ± 5.1 | 127 ± 50 |

Figure 6:
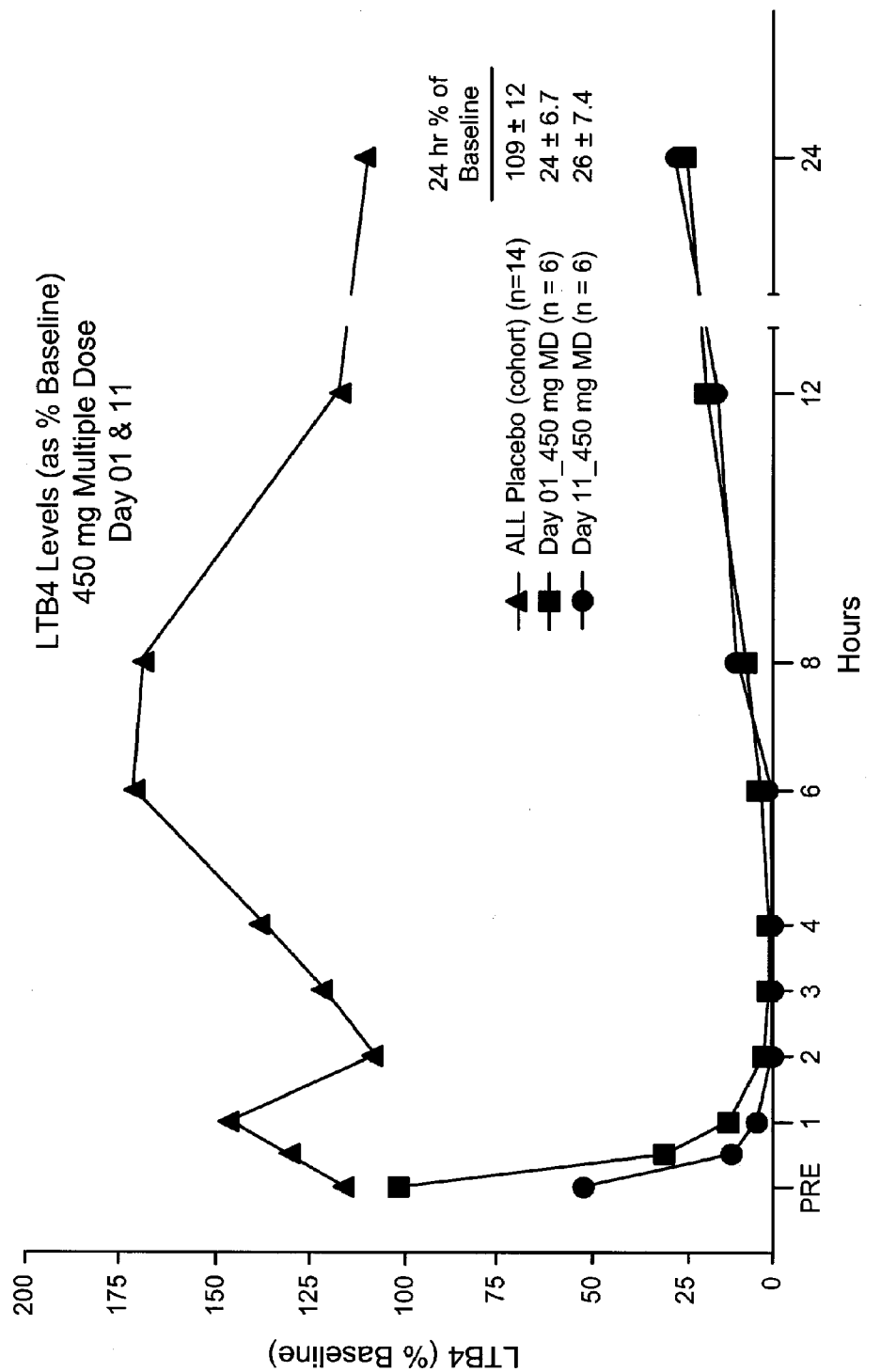
FIG. 6 presents pharmacodynamic properties of multiple dose administrations of an aqueous solution comprising sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate to healthy adult human subjects in the fasted state.
Figure 7:
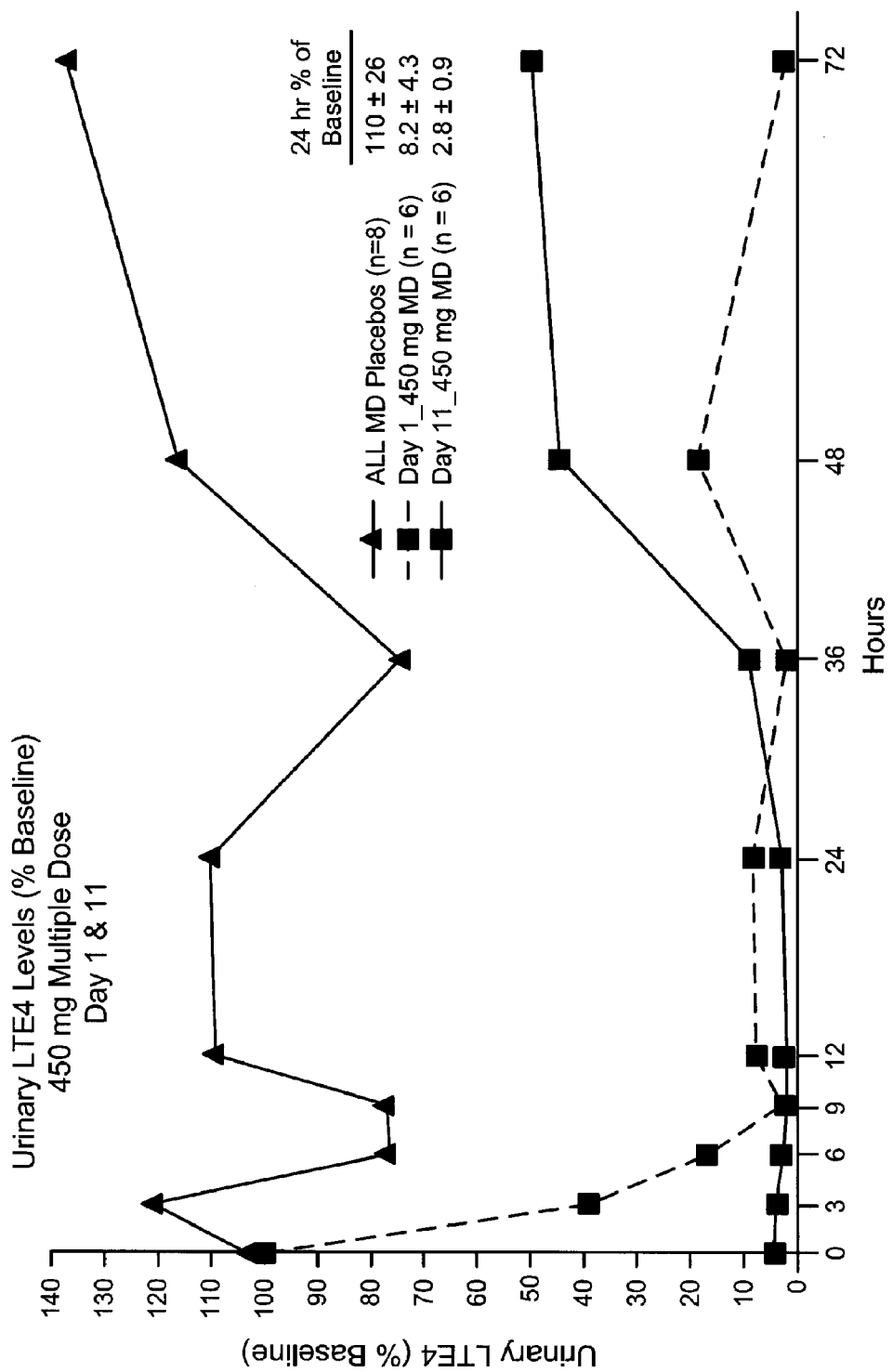
FIG. 7 presents pharmacodynamic properties (urinary $LTE_4$ levels) of multiple dose administration of aqueous solutions of sodium 3-[5-(pyridin-2-ylmethoxy)-3-(2-methyl-2-propylthio)-1-[4-(2-methoxypyridin-5-yl)benzyl]-indol-2-yl]-2,2-dimethyl-propionate to healthy adult human subjects in the fasted state.

The pharmacodynamic data after the multiple doses were administered (blood $LTB_4$ levels and urinary $LTE_4$ levels) is presented in Table 28 and FIG. 6 and FIG. 7.

TABLE 28

Multiple Dose $LTB_4$ levels and $LTE_4$ levels using oral solutions.

| | $LTB_4$ level at t = 24 hrs. (% of baseline) | | $LTE_4$ level at t = 24 hrs. (% of baseline) | |
|---|---|---|---|---|
| Dose of Active | Day 1 | Day 11 | Day 1 | Day 11 |
| Placebo | 109 ± 12 | 109 ± 12 | 110 ± 26 | 110 ± 26 |
| 450 mg | 24 ± 6.7 | 26 ± 7.4 | 8.2 ± 4.3 | 2.8 ± 0.9 |
| 1000 mg | 2.7 ± 1.1 | 1.0 ± 0.6 | 2.5 ± 0.6 | 2.3 ± 0.6 |

The foregoing clinical trial has shown that 3-[5-(pyridin-2-ylmethoxy)-3-(2-methyl-2-propylthio)-1-[4-(2-methoxypyridin-5-yl)benzyl]indol-2-yl]-2,2-dimethyl-propionic acid drug substance lowers $LTB_4$ and $LTE_4$ levels in humans, two leukotrienes that are elevated in humans with leukotriene-dependent or leukotriene mediated conditions or diseases. Lowering leukotriene levels in humans with leukotriene-dependent or leukotriene mediated conditions or diseases provides benefit in the condition or disease. The foregoing clinical trial has shown that 3-[5-(pyridin-2-ylmethoxy)-3-(2-methyl-2-propylthio)-1-[4-(2-methoxypyridin-5-yl)benzyl]-indol-2-yl]-2,2-dimethyl-propionic acid is useful in the treatment or prevention of leukotriene-dependent or leukotriene mediated conditions or diseases.

The examples and embodiments described herein are for illustrative purposes only and various modifications or changes suggested to persons skilled in the art are to be included within the spirit and purview of this application and scope of the appended claims.

What is claimed is:

1. A crystalline form of sodium 3-[(5-pyridin-2yl-methoxy)-3-(2-methyl-2-propylthio)-1-[4-(2-methoxypyridin-5-yl)benzyl]-indol-2-yl]-2,2-dimethyl-propionate or pharmaceutically acceptable solvate thereof, having:
   an X-ray powder diffraction pattern with characteristic deg 2θ values of 7.2, 9.1, 18.2, 18.9, 20.9, and 22.3; or
   an X-ray powder diffraction pattern with characteristic deg 2θ values of 12.0, 17.4, 18.2, 19.0, 20.5, and 23.2; or
   an X-ray powder diffraction (XRPD) pattern comprising the peaks set forth in FIG. 1; or
   an X-ray powder diffraction (XRPD) pattern comprising the peaks set forth in FIG. 2.

2. A crystalline form of sodium 3-[(5-pyridin-2yl-methoxy)-3-(2-methyl-2-propylthio)-1-[4-(2-methoxypyridin-5-yl)benzyl]-indol-2-yl]-2,2-dimethyl-propionate having an X-ray powder diffraction pattern with characteristic deg 2θ values of 7.2, 9.1, 18.2, 18.9, 20.9, and 22.3, present in solvated form.

3. A crystalline form of sodium 3-[(5-pyridin-2yl-methoxy)-3-(2-methyl-2-propylthio)-1-[4-(2-methoxypyridin-5-yl)benzyl]-indol-2-yl]-2,2-dimethyl-propionate having an X-ray powder diffraction pattern with characteristic deg 2θ values of 12.0, 17.4, 18.2, 19.0, 20.5, and 23.2, present in desolvated form.

4. A crystalline form of sodium 3-[(5-pyridin-2yl-methoxy)-3-(2-methyl-2-propylthio)-1-[4-(2-methoxypyridin-5-yl)benzyl]-indol-2-yl]-2,2-dimethyl-propionate having an X-ray powder diffraction (XRPD) pattern comprising the peaks set forth in FIG. 1.

5. A crystalline form of sodium 3-[(5-pyridin-2yl-methoxy)-3-(2-methyl-2-propylthio)-1-[4-(2-methoxypyridin-5-yl)benzyl]-indol-2-yl]-2,2-dimethyl-propionate having an X-ray powder diffraction (XRPD) pattern comprising the peaks set forth in FIG. 2.

6. A pharmaceutical composition comprising:
a crystalline form of sodium 3-[(5-pyridin-2ylmethoxy)-3-(2-methyl-2-propylthio)-1-[4-(2-methoxypyridin-5-yl)benzyl]-indol-2-yl]-2,2-dimethyl-propionate as set forth in claim 1; and
at least one pharmaceutically acceptable inactive ingredient selected from among excipients, diluents, and carriers.

7. The pharmaceutical composition according to claim 6, wherein the pharmaceutical composition is in the form of a pill, capsule, or tablet.

8. A pharmaceutical composition comprising:
a crystalline form of sodium 3-[(5-pyridin-2ylmethoxy)-3-(2-methyl-2-propylthio)-1-[4-(2-methoxypyridin-5-yl)benzyl]-indol-2-yl]-2,2-dimethyl-propionate as set forth in claim 2; and
at least one pharmaceutically acceptable inactive ingredient selected from among excipients, diluents, and carriers.

9. The pharmaceutical composition according to claim 8, wherein the pharmaceutical composition is in the form of a pill, capsule, or tablet.

10. A pharmaceutical composition comprising:
a crystalline form of sodium 3-[(5-pyridin-2ylmethoxy)-3-(2-methyl-2-propylthio)-1-[4-(2-methoxypyridin-5-yl)benzyl]-indol-2-yl]-2,2-dimethyl-propionate as set forth in claim 3; and
at least one pharmaceutically acceptable inactive ingredient selected from among excipients, diluents, and carriers.

11. The pharmaceutical composition according to claim 10, wherein the pharmaceutical composition is in the form of a pill, capsule, or tablet.

12. A pharmaceutical composition comprising:
a crystalline form of sodium 3-[(5-pyridin-2ylmethoxy)-3-(2-methyl-2-propylthio)-1-[4-(2-methoxypyridin-5-yl)benzyl]-indol-2-yl]-2,2-dimethyl-propionate as set forth in claim 4; and
at least one pharmaceutically acceptable inactive ingredient selected from among excipients, diluents, and carriers.

13. The pharmaceutical composition according to claim 12, wherein the pharmaceutical composition is in the form of a pill, capsule, or tablet.

14. A pharmaceutical composition comprising:
a crystalline form of sodium 3-[(5-pyridin-2ylmethoxy)-3-(2-methyl-2-propylthio)-1-[4-(2-methoxypyridin-5-yl)benzyl]-indol-2-yl]-2,2-dimethyl-propionate as set forth in claim 5; and
at least one pharmaceutically acceptable inactive ingredient selected from among excipients, diluents, and carriers.

15. The pharmaceutical composition according to claim 14, wherein the pharmaceutical composition is in the form of a pill, capsule, or tablet.

* * * * *